(12) United States Patent
Carmona Orozco et al.

(10) Patent No.: US 9,938,525 B2
(45) Date of Patent: Apr. 10, 2018

(54) COMPOSITIONS AND METHODS FOR SELECTIVE DELIVERY OF OLIGONUCLEOTIDE MOLECULES TO CELL TYPES

(71) Applicant: nLife Therapeutics, S.L., Armilla, Granada (ES)

(72) Inventors: Maria del Carmen Carmona Orozco, Terrassa (ES); Andrés Pablo Montefeltro, Barcelona (ES); Gabriel G. Alvarado, Ontario (CA); Analia Bortolozzi, Barcelona (ES); Raquel Revilla-Sanchez, Granada (ES)

(73) Assignee: NLIFE THERAPEUTICS, S.L., Armilla, Granada (ES)

( * ) Notice: Subject to any disclaimer, the term of this patent is extended or adjusted under 35 U.S.C. 154(b) by 0 days.

(21) Appl. No.: 14/438,869

(22) PCT Filed: Oct. 25, 2013

(86) PCT No.: PCT/EP2013/072411
§ 371 (c)(1),
(2) Date: Apr. 27, 2015

(87) PCT Pub. No.: WO2014/064258
PCT Pub. Date: May 1, 2014

(65) Prior Publication Data
US 2015/0315575 A1 Nov. 5, 2015

(30) Foreign Application Priority Data
Oct. 26, 2012 (EP) .................................... 12382413

(51) Int. Cl.
| | | |
|---|---|---|
| *C12N 15/113* | (2010.01) | |
| *A61K 31/711* | (2006.01) | |
| *A61K 31/7088* | (2006.01) | |
| *A61K 31/713* | (2006.01) | |
| *C07K 5/065* | (2006.01) | |
| *A61K 31/165* | (2006.01) | |
| *A61K 47/54* | (2017.01) | |
| *A61K 47/55* | (2017.01) | |
| *A61K 47/64* | (2017.01) | |

(52) U.S. Cl.
CPC .......... *C12N 15/113* (2013.01); *A61K 31/165* (2013.01); *A61K 31/7088* (2013.01); *A61K 31/711* (2013.01); *A61K 31/713* (2013.01); *A61K 47/54* (2017.08); *A61K 47/55* (2017.08); *A61K 47/64* (2017.08); *C07K 5/06078* (2013.01); *C12N 15/1137* (2013.01); *C12N 2310/11* (2013.01); *C12N 2310/14* (2013.01); *C12N 2310/315* (2013.01); *C12N 2310/321* (2013.01); *C12N 2310/346* (2013.01); *C12N 2310/3513* (2013.01)

(58) Field of Classification Search
None
See application file for complete search history.

(56) References Cited

U.S. PATENT DOCUMENTS

| | | |
|---|---|---|
| 8,106,022 B2 | 1/2012 | Manoharan et al. |
| 2004/0087530 A1 | 5/2004 | Flier et al. |
| 2005/0261266 A1 | 11/2005 | Filer |
| 2007/0105803 A1 | 5/2007 | Manoharan et al. |
| 2009/0176705 A1 | 7/2009 | McDunn et al. |
| 2009/0239814 A1* | 9/2009 | Manoharan ...... A61K 47/48092 514/26 |
| 2010/0135952 A1 | 6/2010 | Axelrod et al. |
| 2010/0267802 A1* | 10/2010 | Sullenger ............... C12N 15/111 514/44 A |
| 2011/0124706 A1* | 5/2011 | He ..................... A61K 31/7105 514/44 A |
| 2011/0160135 A1* | 6/2011 | Johnstone ............... C12P 21/06 514/10.8 |

FOREIGN PATENT DOCUMENTS

| | | |
|---|---|---|
| WO | WO 96/22997 A1 | 8/1996 |
| WO | WO 97/26270 A2 | 7/1997 |
| WO | WO 03/007088 A2 | 1/2003 |
| WO | WO 2005/114180 A2 | 12/2005 |
| WO | WO 2007/106944 A1 | 9/2007 |

(Continued)

OTHER PUBLICATIONS

Alberico, R.A., et al., "Imaging in head and neck oncology," *Surg. Oncol. Clin. N. Am.* 13:13-35, Elsevier Inc., Netherlands (2004) (Abstract only).
Altschul, S.F., et al., "Basic Local Alignment Search Tool," *J. Mol. Biol.* 215:403-410, Academic Press Limited, United States (1990).
Beaucage, S.L. and Iyer, R.P., "The Functionalization of Oligonucleotides via Phosphoramidite Derivatives," *Tetrahedron* 49(10):1925-1963, Pergamon Press Ltd., United Kingdom (1993).
Borroni, E., et al., "Pre-clinical characterization of [$^{11}$C]R05013853 as a novel radiotracer for imaging of the glycine transporter type 1 by positron emission tomography," *NeuroImage* 75:291-300, Elsevier Inc., Netherlands (2011).
Carpino, P.A. and Ho, G., "Modulators of the ghrelin system as potential treatments for obesity and diabetes," *Expert Opin. Ther. Patents* 18(11):1253-1263, Informa UK Ltd., United Kingdom (2008).

(Continued)

*Primary Examiner* — Tracy Vivlemore
(74) *Attorney, Agent, or Firm* — Sterne, Kessler, Goldstein & Fox P.L.L.C.

(57) ABSTRACT

The invention provides a conjugate comprising (i) a nucleic acid which is complementary to a target nucleic acid sequence and which expression prevents or reduces expression of the target nucleic acid and (ii) a selectivity agent which is capable of binding with high affinity to a receptor which can be internalized by the cell in response to the binding of said selectivity agent. The conjugates of the present invention are useful for the delivery of the nucleic acid to cell of interests and thus, for the treatment of diseases which require a down-regulation of the protein encoded by the target nucleic acid as well as for the delivery of contrast agents to the cells for diagnostic purposes.

45 Claims, 6 Drawing Sheets

(56) References Cited

FOREIGN PATENT DOCUMENTS

| WO | WO 2011/131693 A2 | 10/2011 |
|----|-------------------|---------|
| WO | WO 2012/082765 A2 | 6/2012  |

OTHER PUBLICATIONS

Crooke, S.T., et al., "Pharmacokinetic Properties of Several Novel Oligonucleotide Analogs in mice," *J. Pharmacol. Exp. Ther.* 277:923-937, The American Society for Pharmacology and Experimental Therapeutics, United States (1996).
Fox, S.W., et al., "The Possible Role of TGF-β-Induced Suppressors of Cytokine Signaling Expression in Osteoclast/Macrophage Lineage Commitment in Vitro," *J. Immunol.* 170:3679-3687, American Association of Immunologists, United States (2003).
Henson, J.W., et al., "Gadolinium-Enhanced CT Angiography of the Circle of Willis and Neck," *Am. J. Neuroradiol.* 25:969-972, American Society of Neuroradiology, United States (2004).
Houle, S., et al., "Imaging the serotonin transporter with positron emission tomography: initial human studies with [$^{11}$C]DAPP and [$^{11}$C]DASB," *Eur. J. Nucl. Med.* 27:1719-1722, Springer-Verlag, Germany (2000).
Kabanov, A.V., et al., "A new class of antivirals: antisense oligonucleotides combined with a hydrophobic substituent effectively inhibit influenza virus reproduction and synthesis of virus-specific proteins in MDCK cells," *FEBS Lett.* 259(2):327-330, Elsevier Science Publishers B.V., Netherlands (1990).
Kroemer, N.B., et al., "Fasting levels of ghrelin covary with the brain response to food pictures," *Addiction Biology* 18:855-862, Society for the Study of Addiction, United Kingdom (2012).
Lammers, R., et al., "Differential Activities of Protein Tyrosine Phosphatases in Intact Cells," *J. Biol. Chem.* 268(30):22456-22462, The American Society for Biochemistry and Molecular Biology, Inc. United States (1993).
Lee, N.S., et al., "Expression of small interfering RNAs targeted against HIV-1 rev transcripts in human cells," *Nature Biotechnology* 19:500-505, Nature Publishing Group, United Kingdom (2002).
Letsinger, R.L., et al., "Cholesteryl-conjugated oligonucleotides: Synthesis, properties, and activity as inhibitors of replication of human immunodeficiency virus in cell culture," *Proc. Natl. Acad. Sci. USA* 86:6553-6556, United States (1989).
Liu, G., "Protein Tyrosine Phosphatase 1B Inhibition: Opportunities and Challenges," *Current Medicinal Chemistry* 10:1407-1421, Bentham Science Publishers Ltd., United Arab Emirates (2003).
Logan, J., et al., "Imaging the norepinephrine transporter in humans with (S,S)-[$^{11}$C]O-methyl reboxetine and PET: problems and progress," *Nuclear Medicine and Biology* 34:667-679, Elsevier Inc., Netherlands (2007).
Manoharan, M., et al., "Chemical Modifications to Improve Uptake and Bioavailability of Antisense Oligonucleotides," *Ann. N.Y. Acad. Sci.* 660:306-309, The New York Academy of Science, United States (1992).
Manoharan, M., et al., "Introduction of a Lipophilic Thioether Tether in the Minor Groove of Nucleic Acids for Antisense Applications," *Bioorganic & Medicinal Chemistry Letters* 3(12):2765-2770, Pergamon Press Ltd., United Kingdom (1993).
Manoharan, M., et al., "Cholic Acid-Oligonucleotide Conjugates for Antisense Applications," *Bioorganic & Medicinal Chemistry Letters* 4(8):1053-1060, Elsevier Science Ltd., Netherlands (1994).
Manoharan, M., et al., "Lipidic Nucleic Acids," *Tetrahedron Letters* 36(21):3651-3654, Elsevier Science Ltd., Netherlands (1995).
Manoharan, M., et al., "Oligonucleotide Conjugates: Alteration of the Pharmacokinetic Properties of Antisense Agents," *Nucleosides & Nucleotides* 14(3-5):969-973, Marcel Dekker, Inc. United States (1995).
Mishra, R.K., et al., "Improved leishmanicidal effect of phosphorotioate antisense oligonucleotides by LDL-mediated delivery," *Biochimica et Biophysica Acta* 1264:229-237, Elsevier Science B.V., Netherlands (1995).

Oberhauser, B. and Wagner, E., "Effective incorporation of 2'-O-methyl-oligoribonucleotides into liposomes and enhanced cell association through modification with thiocholesterol," *Nucleic Acids Research* 20(3):533-538, Oxford University Press, United Kingdom (1992).
Oney, S., et al., "Antidote-Controlled Platelet Inhibition Targeting von Willebrand Factor with Aptamers," *Oligonucleotides* 17:265-274, Mary Ann Liebert, Inc., United States (2007).
Que-Gewirth, N.S. and Sullenger, B.A., "Gene therapy progress and prospects: RNA aptamers," *Gene Therapy* 14:283-291, Nature Publishing Group, United Kingdom (2007).
Raghavendra Rao, V.L., et al., "Gene expression analysis of spontaneously hypertensive rat cerebral cortex following transient focal cerebral ischemia," *Journal of Neurochemistry* 83:1072-1086, International Society for Neurochemistry, United States (2002).
Ramachandran, C., et al., "Sequential Dephosphorylation of a Multiply Phosphorylated Insulin Receptor Peptide by Protein Tyrosine Phosphatases," *Biochemistry* 31:4232-4238, American Chemical Society, United States (1992).
Saison-Behmoaras, T., et al., "Short modified antisense oligonucleotides directed against Ha-ras point mutation induce selective cleavage of the mRNA and inhibit T24 cells proliferation," *The EMBO Journal* 10(5):1111-1118, Oxford University Press, United Kingdom (1991).
Seim, I., et al., "Ghrelin and the Brain-gut Axis as a Pharmacological Target for Appetite Control," *Current Pharmaceutical Design* 18:768-775, Bentham Science Publishers, United Arab Emirates (2012).
Shamah, S.M., et al., "Complex Target SELEX," *Accounts of Chemical Research* 41(1):130-138, American Chemical Society, United States (2008).
Shea, R.G., et al., "Synthesis, hybridization properties and antiviral activity of lipid-oligodeoxynucleotide conjugates," *Nucleic Acids Research* 18(13):3777-3783, Oxford University Press, United Kingdom (1990).
Spilsberg, B., et al., "Reconstitution of active diphtheria toxin based on a hexahistidine tagged version of the B-fragment produced to high yields in bacteria," *Toxicon* 46:900-906, Elsevier Ltd., Netherlands (2005).
Stein, C.A. and Cohen, J.S., "Oligodeoxynucleotides as Inhibitors of Gene Expression: A Review," *Cancer Res.* 48:2659-2668, American Association for Cancer Research, United States (1988).
Stoica, G., et al., "Potential role of α-synuclein in neurodegeneration: studies in a rat animal model," *J. Neurochem.* 122:812-822, International Society for Neurochemistry, United States (2012).
Strunk, H.M. and Schild, H., "Actual clinical use of gadolinium-chelates for non-MRI applications," *Eur. Radiol.* 14:1055-1062, Springer-Verlag, Germany (2004).
Subbarao, N.K., et al., "pH-Dependent Bilayer Destabilization by an Amphipathic Peptide," *Biochemisty* 26:2964-2972, American Chemical Society, United States (1987).
Sui, G., et al., "A DNA vector-based RNAi technology to suppress gene expression in mammalian cells," *PNAS* 99(8):5515-5520, National Academy of Sciences, United States.
Svinarchuk, F.P., et al., "Inhibition of HIV proliferation in MT-4 cells by antisense oligonucleotide conjugated to lipophilic groups," *Biochimie* 75:49-54, Elsevier, France (1993).
Thompson, J.D., et al., "CLUSTAL W: improving the sensitivity of progressive multiple sequence alignment through sequence weighting, position-specific gap penalties and weight matrix choice," *Nucleic Acids Research* 22(22):4673-4680, Oxford University Press, United Kingdom (1994).
Tonks, N.K., et al., "Characterization of the Major Protein-tyrosine-phosphatases of Human Placenta," *The Journal of Biological Chemistry* 263(14):6731-6737, The American Society for Biochemistry and Molecular Biology, Inc., United States (1988).
Turk, M.J., et al., "Characterization of a novel pH-sensitive peptide that enhances drug release from folate-targeted liposomes at endosomal pHs," *Biochimica et Biophysica Acta* 1559:56-68, Elsevier Science B.V., Netherlands (2002).

(56) References Cited

OTHER PUBLICATIONS

Ueno, S., et al., "In vitro selection of a peptide antagonist of growth hormone secretagogue receptor using cDNA display," *PNAS* 109(28):11121-11126, National Academy of Sciences, United States (2012).
Van Der Krol, A.R., et al., "Modulation of Eukaryotic Gene Expression by Complementary RNA or DNA Sequences," *BioTechniques* 6(10):958-976, Eaton Publishing Co., United States (1988).
Varrone, A. and Halldin, C., "Molecular Imaging of the Dopamine Transporter," *J. Nucl. Med.* 51:1331-1334, The Society of Nuclear Medicine, Inc., United States (2010).
Vogel, K., et al., "Peptide-Mediated Release of Folate-Targeted Liposome Contents from Endosomal Compartments," *J. Am. Chem. Soc.* 118(7): 1581-1586, American Chemical Society, United States (1996).
Zhao, H. and Liu, G., "Growth hormone secretagogue receptor antagonists as anti-obesity therapies? Still an open question," *Current Opinion in Drug Discovery & Development* 9(4):509-515, The Thomson Corporation, United States (2006).
International Search Report for International Application No. PCT/EP2013/072411, European Patent Office, Rijswijk, Netherlands, dated Mar. 7, 2014.

\* cited by examiner ic acid to a cell of interest which expresses a receptor by covalently coupling said nucleic acid to a molecule which is capable of specifically binding to said receptor. Moreover,

COMPOSITIONS AND METHODS FOR SELECTIVE DELIVERY OF OLIGONUCLEOTIDE MOLECULES TO CELL TYPES

REFERENCE TO SEQUENCE LISTING SUBMITTED ELECTRONICALLY

The content of the electronically submitted sequence listing (Name 32460050001_sequencelisting.txt; Size: 8 kilobytes; and Date of Creation: Apr. 27, 2015) filed with the application is incorporated herein by reference in its entirety.

FIELD OF THE INVENTION

The present invention relates to conjugates comprising a nucleic acid specific for a target of interest and a group which allows the delivery of the nucleic acids to specific cells by means of their affinity towards G-protein coupled receptors on the surface of said cells.

BACKGROUND ART

The use of nucleic acids has proved effective for altering the state of a cell. The introduction of deoxyribonucleic acid (DNA) or ribonucleic acid (RNA) into a cell can be used to up- or down-regulate the expression of particular genes in the cell, thereby, impacting one or more biochemical pathways. Of the nucleic acid-based technologies used to alter cell physiology, RNA interference (RNAi) is the general term given for regulating the expression of genes at the post-transcriptional level in diversified organisms. RNAi gene silencing can be accomplished using homologous short (21-23 bp) dsRNA fragments known as short interfering or "siRNA." When a long dsRNA is introduced into a cell line, the cellular enzyme Dicer will cleave it into short interfering RNA (siRNA) molecules. This short interfering RNA molecule is now called the guided RNA. The guided RNA will guide the RNA-Induced-Silencing-Complex (RISC) to the homologous target mRNA. Once it forms a hybrid structure to the homologous mRNA sequence, the RISC will cleave the mRNA. As a result, protein that is encoded by the mRNA will no longer be produced, thereby causing the silencing of the gene. RNA interference refers to the process of sequence-specific post-transcriptional gene silencing in animals mediated by short interfering RNAs (siRNAs).

SUMMARY OF THE INVENTION

The inventors have developed nucleic acid constructs which contain a nucleic acid specific for given target molecule and a selective ligand of a receptor which can be endocytosed in response to the binding of the selective ligand. These constructs are shown to be particularly useful for the delivery of the nucleic acid of interest to the interior of a cell expressing the receptor. Without wishing to be bound by any theory, it is believed that the ligand will bind to the corresponding receptor in the surface of the cell wherein the receptor is expressed. This will in turn result in the translocation of the complex nucleic acid-inhibitor to the interior of the cell by means of receptor-mediated endocytosis.

The skilled person will appreciate that the invention is not limited to conjugate for delivery to cells expressing GSH-R. On the contrary, the results provided in the present invention illustrate that the mechanism used by the cells to signal via surface receptor are adequate means for promoting delivery to cells of small molecules attached to molecules showing affinity for said receptors.

DETAILED DESCRIPTION OF THE INVENTION

Figure 1:
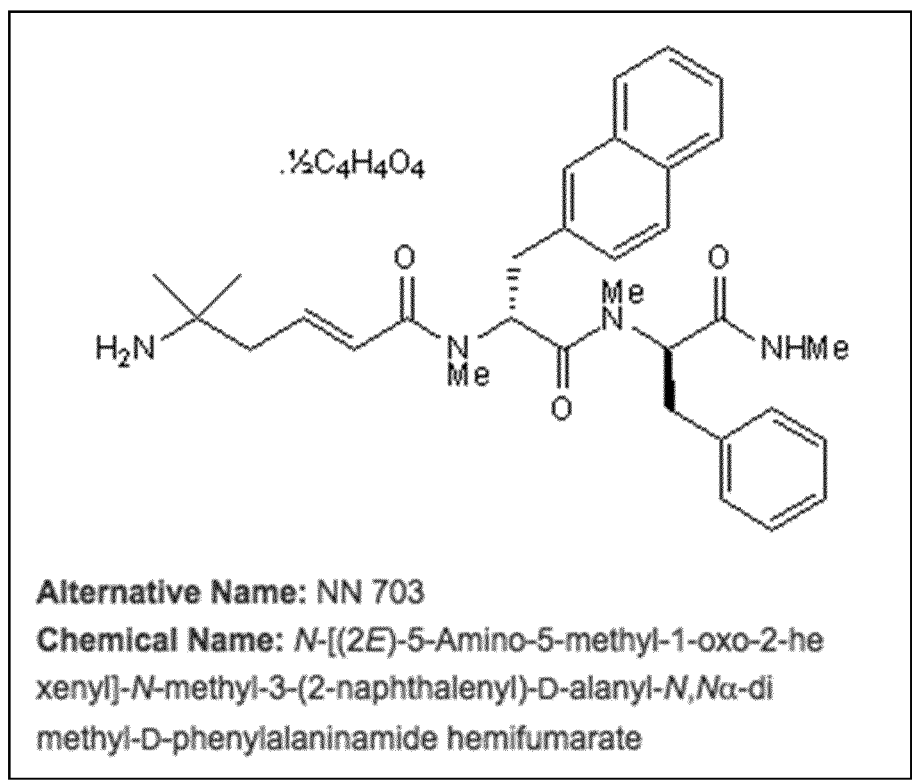
FIG. 1. Tabimorelin structure. Potent, orally active ghrelin receptor (GHS-R1a) agonist ($K_i$=50 nM at human recombinant GHS-R1a). Stimulates GH release from rat pituitary cells with an $EC_{50}$ value of 2.7 nM.

The authors of the present invention have observed that, unexpectedly, it is possible to specifically target a nucleic acid to a cell of interest which expresses a receptor by covalently coupling said nucleic acid to a molecule which is capable of specifically binding to said receptor. Moreover, the authors of the present invention have also observed that the nucleic acid can be internalized by the cells, thereby exerting its effects. Without wishing to be bound by any theory, it is believed that the conjugates are internalized by the receptor as the receptor is internalized in response to the binding of the selectivity agent. For instance, as shown in the examples of the present invention, animals treated with a conjugate containing a ligand for the growth hormone secretagogue receptor (tabimorelin) and a nucleic acid capable of specifically silencing either SOCS4 or PTP1B gain significantly less weight and show reduced food intake than control animals (VH and NS), thereby showing that the nucleic acids were effective in reaching the targeted hypothalamic areas A. Conjugates of the Invention In a first aspect, the invention relates to a conjugate comprising:
i) at least one selectivity agent which binds specifically to a receptor which undergoes endocytosis upon binding of said selectivity agent and
ii) at least one nucleic acid which is capable of specifically inhibiting a target molecule which is expressed in the same cell as the receptor.

The term "conjugate", as used herein, refers to any compound resulting from the covalent attachment of two or more individual compounds. In the present invention, conjugate refers to a molecule comprising a nucleic acid a selectivity agent which are covalently coupled, being said coupling direct or via a linking compound.

The terms "covalent coupling" or "covalent attachment" mean that the nucleic acid and the selectivity agent are either directly covalently joined to one another, or else are indirectly covalently joined to one another through an intervening moiety or moieties, such as a linker, or a bridge, or a spacer, moiety or moieties.

A.1. The Selectivity Agent

The terms "selectivity agent which binds specifically to one or more of a receptor", as used herein, refers to any substance which binds to a receptor, wherein the receptor undergoes endocytosis in response to the binding of said selectivity agent. This binding specificity allows the delivery of a molecule which is attached to said selectivity agent to the cell, tissue or organ which expresses said receptor. In this way, a conjugate carrying said selectivity agent will be directed specifically to said cells when administered to an animal or contacted in vitro with a population of cells of different types.

The term "receptor" denotes a cell-associated protein that binds to a bioactive molecule termed a "ligand.

As used herein, specific binding of a first molecule to a second molecule refers to the ability of the first molecule to bind said second molecule in a way that is measurably different from a non-specific interaction. A selectivity agent according to the present invention may show a Kd for the target (the receptor) of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M or greater.

Receptors which may be targeted by the selectivity agents of the invention also include, without limitation, a 5-hydroxytryptamine receptor, an adenosine receptor, an adrenoceptor receptor, an angiotensin receptors, a bombesin receptors, a bradykinin receptors, a calcitonin receptor, a chemokine receptor, a cholecystokinin receptor, a corticotropin-releasing factor receptor, a dopamine receptor, an endothelin receptor, en ephrin receptor, a formylpeptide receptor, a Frizzled receptor, a galanin receptor, a the growth hormone secretagogue receptor (Ghrelin) receptor, a Kisspeptin receptor, a melanocortin receptor, a melatonin receptors, Neuropeptide FF/neuropeptide AF receptor, a neuropeptide S receptor, a neuropeptide W/neuropeptide B receptor, a neuropeptide Y receptor, a neurotensin receptor, an opiod receptor, an orexin receptors, a peptide P518 receptor, a prostanoid receptor, a SLC6 neurotransmitter transporter family, a somatostatin receptor, a tachykinin receptor, a Toll-like receptor, a vasopressin and oxytocin receptor and a VEGF receptor.

In another preferred embodiment, the receptors that can be targeted by the selectivity agent of the conjugates according to the invention are as defined in Table 1.

TABLE 1

Receptor families and specific receptors

| FAMILY NAME, IUPHAR DATABASE | OFFICIAL IUPHAR SUBTYPE NAME |
|---|---|
| 5-Hydroxytryptamine receptors | 5-HT1A |
| | 5-HT1B |
| | 5-HT2A |
| | 5-HT3 |
| | 5-HT1D |
| | 5-HT6 |
| Adenosine receptors | A1 |
| | A2 |
| | A2A |
| Adrenoceptors receptors | alpha1A-adrenoceptor |
| | alpha1B-adrenoceptor |
| | alpha1D-adrenoceptor |
| Angiotensin receptors | AT2 |
| Bombesin receptors receptors | BB1 |
| | BB2 |
| | BB3 |
| Bradykinin receptors | B1 |
| | B2 |
| Calcitonin receptors | CT receptor-like CRL |
| | AM1 |
| | AMY1 |
| | CGRP |
| | CT-R |
| | AM2 |
| | AMY3 |
| Chemokien receptor | CXCR4 |
| Cholecystokinin receptors | CCK2 |
| Corticotropin-releasing factor receptors | CRF1 |
| | CRF2 |
| Dopamine receptors | D1 |
| | D2 |
| Eprhin receptors | EphA1 |
| | EphA2 |
| | EphA3 |
| | EphA4 |
| | EphB1 |
| | EphB2 |
| | EphB3 |
| Endothelin receptors | ETa |
| | ETb |
| Formylpeptide receptors | FPR1 |
| | FPR2/ALX |
| | FPR3 |
| Frizzled receptors | FZD2 |
| | FZD3 |
| | FZD4 |
| | FZD5 |
| | FZD6 |
| | FZD7 |
| | FZD8 |
| | FZD9 |
| | FZD10 |
| Galanin receptors | GAL1 |
| | GAL2 |
| | GAL3 |

TABLE 1-continued

Receptor families and specific receptors

| FAMILY NAME, IUPHAR DATABASE | OFFICIAL IUPHAR SUBTYPE NAME |
|---|---|
| Ghrelin receptor | Ghrelin receptor |
| Kisspeptin receptor | Kisspeptin receptor |
| Melanocortin receptors | MC1 |
|  | MC2 |
|  | MC3 |
|  | MC4 |
| Melatonin receptors | MT2 |
|  | MT1 |
| Neuropeptide FF/neuropeptide AF receptors | NPFF2 |
|  | NPFF1 |
| Neuropeptide S receptors | NPS receptor |
| Neuropeptide W/neuropeptide B receptors | NPBW2 |
| Neuropeptide Y receptors | Y1 |
|  | Y2 |
|  | Y5 |
|  | Y4 |
| Neurotensin receptors | NTS2 |
|  | NTS1 |
| Opiod receptors | delta |
|  | kappa |
|  | mu |
| Orexin receptors | OX1 |
|  | OX2 |
| Peptide P518 receptor | QRFP |
| SLC6 neurotransmitter transporter family | DAT |
|  | NET |
|  | SERT |
|  | GlyT1 |
| Somatostatin receptors | sst2 |
|  | sst3 |
|  | sst4 |
|  | sst1 |
|  | sst5 |
| Tachykinin receptors | NK1 |
|  | NK2 |
|  | NK3 |
| Toll-like receptors | TLR7 |
| Vasopressin and oxytocin receptors | OT |
|  | V1A |
|  | V1B |
|  | V2 |
| VEGF receptors | VEGFR1 |
|  | VEGFR2 |
|  | VEGFR3 |

In a preferred embodiment, the receptor is a G-protein coupled receptor.

As used herein, the term "G-protein coupled receptor" (or "GPCR") refers to a target receptor that, when expressed by a cell, associates with a G-protein (e.g., a protein which hydrolyzes GTP). Preferably, the GPCR is a "seven transmembrane segment receptor" (or "7 TMS receptor"), which refers to a protein that structurally comprises seven hydrophobic transmembrane spanning regions.

In another embodiment, the receptor is expressed at one or more locations of the central nervous system. In yet another embodiment, said location of the central nervous system is selected from the group consisting of the hypothalamus, the brainstem, the cortex, the cerebellum, the striatum, the mesencephalon, the hippocampus, the glia and the spinal cord.

In a preferred embodiment, the selectivity ligand within the conjugate binds to a receptor which is expressed in the hypothalamus. In a still more preferred embodiment, the receptor which is expressed in the hypothalamus is selected from the group consisting of the growth hormone secretagogue receptor, the galanin GAL1 receptor, the calcitonin receptor-like, the neuropeptide FF/B NPBW2 receptor, the neuropeptide FF/B NPFF2 receptor, the neuropeptide Y Y2 receptor, the bombesin BB2 receptor, the bombesin BB3 receptor, the calcitonin AM1 receptor, the calcitonin AMY1 receptor, the calcitonin CGRP receptor the calcitonin receptor, the frizzled FZD2 receptor, the frizzled FZD5 receptor, the melanocortin MC2 receptor, the melanocortin MC3 receptor, the melanocortin MC4 receptor, the neuropeptide S receptor, the neuropeptide FF/B NPFF1 receptor, the neuropeptide Y Y4 receptor, the neurotensin NTSR1 receptor, the orexin OX1 receptor, the orexin OX2 receptor, the somatostatin sst1 receptor, the somatostatin sst5 receptor, the oxytocin receptor, the vassopressin VIA receptor, the vasopressin V1B receptor, the vassopresin V2 receptor, the kisspeptin receptor, the neuropeptide FF/B NPBW1 receptor, the peptide P518 receptor, the tachykinin NK1 receptor, the tachykinin NK2 receptor and the tachykinin NK3 receptor.

In a preferred embodiment, the ligand which binds to the receptor is selected from the group of the ligands shown in Table 2. In another preferred embodiment, the selectivity agent is a GHS-R agonist.

In a still more preferred embodiment, the GHS-R agonist is tabimorelin or a structural analog thereof having the structure (I):

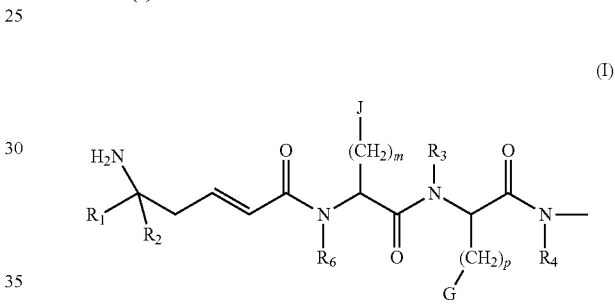

wherein $R_1$ and $R_2$ independently of each other are hydrogen or C1-C6 alkyl or R1 and $R_2$ taken together form a C2-C5 alkylene group;

J is a group

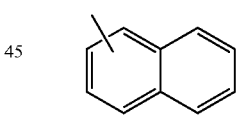

optionally substituted with one or more C1-C6 alkyl or halogen, m is 1, 2 or 3, $R_3$ is C1-C6 alkyl, p is 1, 2 or 3, G is a group

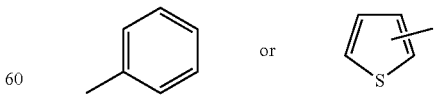

optionally substituted with one or more $C_1$-$C_6$ alkyl or halogen, $R_4$ and $R_5$ independently of each other are hydrogen or $C_1$-$C_6$ alkyl and $R_6$ is hydrogen or $C_1$-$C_6$ alkyl, preferably hydrogen.

Compounds of Formula I can have one or more asymmetric centres, and any and all optical isomers in the form of separated, pure or partially purified optical isomers or racemic mixtures thereof are included within the scope of Formula I. Both E and Z geometric isomers (with respect to the olefinic double bond to the left in the structure of Formula I as depicted above) are likewise included within the scope of Formula I.

In one aspect, the invention provides conjugates comprising compound according to Formula I wherein $R_1$ and $R_2$ are both alkyl, preferably methyl. In one aspect, the invention provides conjugates comprising compound according to Formula I wherein J is also or alternatively 2-naphthyl. In one aspect, m also or alternatively is one. In one aspect, R3 is methyl. In another aspect, p is one. In another aspect, G is phenyl.

In another aspect, R4 is methyl. In another aspect, R5 is hydrogen or methyl. In yet another aspect, R6 is hydrogen or methyl.

The term "C1-6 alkyl", as used in the present invention, is intended to include straight-chain (linear), branched and cyclic alkyl groups of from 1 to 6 carbon atoms. Relevant linear C1-6 alkyl groups are methyl, ethyl, propyl, butyl, pentyl and hexyl. Examples of branched C1-6alkyl groups are isopropyl, sec-butyl, tert-butyl, isopentyl and isohexyl. Examples of cyclic groups (C3-6cycloalkyl groups) are cyclopropyl, cyclobutyl, cyclopentyl and cyclohexyl. The term "C1-6 alkyl" in the present context likewise includes, for example, cycloalkyl-substituted alkyl groups having from 1 to 6 carbon atoms, examples of which include groups such as (cyclopropyl)methyl, (cyclopropyl)ethyl, (cyclopropyl)propyl, (cyclobutyl)methyl, (cyclobutyl)ethyl and (cyclopentyl) methyl. Particularly suitable C1-6alkyl groups are often chosen among C1-3alkyl groups, i.e. methyl, ethyl, propyl, isopropyl and cyclopropyl.

The term "$C_{2-5}$ alkylene group" (i.e. $C_{2-5}$ alkandiyl group), as used in the present invention, is intended to include both straight-chain (linear) and branched alkandiyl groups of from 2 to 5 carbon atoms. Relevant linear groups are: —CH$_2$—CH$_2$—; —CH$_2$—CH$_2$—CH$_2$—; —CH$_2$—(CH$_2$)$_2$—CH$_2$—; and —CH$_2$—(CH$_2$)$_3$—CH$_2$—. Examples of suitable branched groups include: —CH$_2$—CH(CH$_3$)—; —CH$_2$—CH(CH$_3$)—CH$_2$—; —CH$_2$— CH$_2$—CH(CH$_3$)—; —CH$_2$—(CH$_2$)$_2$—CH(CH$_3$)—; and —CH$_2$—CH$_2$—CH (CH$_3$)—CH$_2$—.

The term "halogen" includes Cl, F, Br and I. Particularly suitable halogens in the context of Formula I are Cl and F.

In a preferred embodiment, the GSH-R agonist is N-[(2E)-5-amino-5-methylhex-enoyl]-N-methyl-3-(2-naphthyl)alanyl-N,Nα-dimethyl-D-phenylalaninamide (tabimorelin)

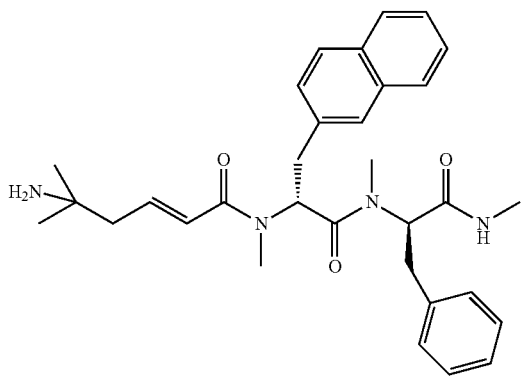 [SMILES: CNC(=O)[C@@H](Cc1ccccc1)N(C)C(=O)[C@@H](Cc1ccc2ccccc2c1)N(C)C(=O)/C=C/CC(C)(C)N]

In another embodiment, the selectivity agent specifically binds to a receptor which is expressed in the mesencephalon. In a preferred embodiment, the receptor which is expressed in the mesencephalon is selected from the group consisting of the growth hormone secretagogue receptor, the bombesin BB1 receptor, the bradykinin B2 receptor, the galanin GAL2 receptor, neuropeptide FF/B NPBW2 receptor, the neuropeptide FF/B NPFF2 receptor, the neuropeptide Y Y1 receptor, the neurotensin NTSR1 receptor, the neurotensin NTSR2 receptor, the neuropeptide S receptor, the orexin OX2 receptor, the 5-HT1D receptor, the angiotensin AT2a receptor, the angiotensin AT2b receptor, the calcitonin AM2 receptor, the calcitonin AMY3 receptor, the frizzled FZD6 receptor, the kisspeptin receptor, the melatonin MT1 receptor, the neuropeptide FF/B NPBW1 receptor and the opioid mu receptor.

In another embodiment, the selectivity agent specifically binds to a receptor which is expressed in the brainstem. In a preferred embodiment, the receptor which is expressed in the brainstem is selected from the group consisting of the 5-HT$_3$ receptor, the galanin receptor 1, the melanocortin MC1 receptor, the melanocortin MC2 receptor, the melanocortin MC3 receptor, the melanocortin MC4 receptor, the calcitonin receptor-like, the CRF2 receptor, the neuropeptide FF/B NPBW2 receptor, the 5-HT$_{1A}$ receptor, the neuropeptide Y Y2 receptor, the neurotensin NTSR1 receptor, the opioid mu receptor, the orexin OX1 receptor, the orexin OX2 receptor and the dopamine D2 receptor. In a more preferred embodiment, the receptor which is expressed in the brainstem is the 5-HT$_3$ receptor.

In a preferred embodiment, the ligand which binds to the 5-HT$_3$ receptor is selected from the group of the ligands shown in Table 2. In another preferred embodiment, the selectivity agent is Lerisetron (1-benzyl-2-piperazin-1-yl-1H-benzimidazole) or lerisetron —C6-acyl. In another embodiment, the selectivity agent specifically binds to a receptor which is expressed in the cortex. In a preferred embodiment, the receptor which is expressed in the cortex is selected from the group consisting of the 5-HT$_3$ receptor, the melanocortin MC1 receptor, the CRF1 receptor, the 5-HT2$_A$ receptor, the alpha1 adrenergic receptor, the bombesin BB1 receptor, the frizzled FZD3 receptor, the bombesin BB3 receptor, the bradykinin B2 receptor, the calcitonin receptor-like receptor, the cholecystokinin CCK2 receptor, the CRF1 receptor, the CRF2 receptor, the galanin GAL2 receptor, the galanin GAL3 receptor, the neuropeptide FF/B NPBW2 receptor, the neuropeptide FF/B NPFF2 receptor, the neuropeptide Y Y1 receptor, the neuropeptide Y Y5 receptor, the neuropeptide Y Y2 receptor, the neurotensin NTSR2 receptor, the opioid kappa receptor, the opioid delta receptor, the somatostatin sst2 receptor, the somatostatin sst3 receptor, the somatostatin sst4 receptor, the 5-HT1A receptor, the endothelin ETa receptor, the endothelin ETb receptor, the melanocortin MC3 receptor, the neuropeptide S NPS receptor, the neurotensin NTSR1 receptor, the orexin OX1 receptor, the orexin OX2 receptor, the vasopressin V1B receptor, the kisspeptin receptor, the melatonin MT1 receptor, the tachykinin NK1 receptor, the tachykinin NK2 receptor and the tachykinin NK3 receptor.

In another embodiment, the selectivity agent specifically binds to a receptor which is expressed in the cerebellum. In a preferred embodiment, the receptor which is expressed in the cerebellum is selected from the group consisting of the CRF1 receptor, the 5-HT$_{1B}$ receptor, the frizzled FZD4 receptor, the frizzled FZD10 receptor, the frizzled FZD7 receptor, the bradikinin B2 receptor, the galanin GAL3 receptor, the neurotensin NTSR2 receptor, the endothelin ETb receptor, the formylpeptide FPR1 receptor, the formylpeptide FPR2 receptor, the melatonin MT2 receptor, the vasopressin V1A receptor, the angiotensin AT2a receptor, the angiotensin AT2b receptor, the kisspeptin receptor and the melatonin MT1 receptor. In a preferred embodiment, the receptor which is expressed in the cerebellum is the 5-HT$_{1B}$ receptor.

In a preferred embodiment, the ligand which binds to the 5-HT$_{1B}$ receptor is selected from the group of the ligands shown in Table 2. In another preferred embodiment, the selectivity agent is a 5-nonyloxytryptamine oxalate or a structural analog thereof having the structure

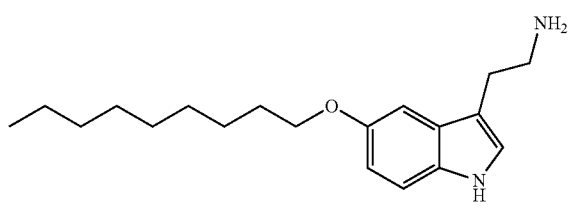 [SMILES: CCCCCCCCCOc1ccc2[nH]cc(CCN)c2c1]

In another embodiment, the selectivity agent specifically binds to a receptor which is expressed in the striatum. In a preferred embodiment, the receptor which is expressed in the striatum is selected from the group consisting of the 5-HT2A receptor, the cholecystokinin CCK2 receptor, the CRF1 receptor, the neuropeptide FF/B NPBW2 receptor, the neuropeptide FF/B NPFF2 receptor, the somatostatin sst5 receptor, the vasopressin V1B receptor, the 5-HT6 receptor, the adenosine A2 receptor, the adenosine A2A receptor, the dopamine D1 receptor, the dopamine D2 receptor, the peptide P518 receptor, the tachykinin NK1 receptor, the tachykinin NK2 receptor and the tachykinin NK3 receptor.

In another embodiment, the selectivity agent specifically binds to a receptor which is expressed in the hippocampus. In a preferred embodiment, the receptor which is expressed in the hippocampus is selected from the group consisting of the 5-HT$_3$ receptor, the bradykinin B2 receptor, the CRF2 receptor, the frizzled FZD3 receptor, the galanin GAL3 receptor, the neuropeptide FF/B NPBW2 receptor, the neuropeptide Y Y1 receptor, the neuropeptide Y Y5 receptor, the neurotensin NTSR2 receptor, the opioid delta receptor, the somatostatin sst3 receptor, the somatostatin sst5 receptor, the 5-HT1A receptor, the adenosine A1 receptor, the endothelin ETa receptor, the endothelin ETb receptor, the formylpeptide FPR1 receptor, the formylpeptide FPR3 receptor, the frizzled FZD8 receptor, the frizzled FZD9 receptor, the melatonin MT2 receptor, the neuropeptide FF/B NPBW2 receptor, the neuropeptide Y Y2 receptor, the neuropeptide FF/B NPFF1 receptor, the neuropeptide Y Y4 receptor, the neurotensin NTSR1 receptor, the orexin OX1 receptor, the orexin OX2 receptor, the somatostatin sst1 receptor, the somatostatin sst5 receptor, the vasopressin V1A receptor and the vasopressin V1B receptor. In a preferred embodiment, the receptor which is expressed in the hippocampus is the 5-HT1A receptor.

In a preferred embodiment, the ligand which binds to the 5-HT1A receptor is selected from the group of the ligands shown in Table 2. In another preferred embodiment, the selectivity agent is LY-165, LY-165,163 C6-acyl, or 8-OH-DPAT.

In another embodiment, the selectivity agent specifically binds to a receptor which is expressed in the medulla. In a preferred embodiment, the receptor which is expressed in the medulla is selected from the group consisting of the EphA1 receptor, the EphA2 receptor, the EphA3 receptor, the EphA4 receptor, the EphB1 receptor, the EphB2 receptor, the EphB3 receptor, the opiuoid mu receptor, the GlyT1 transporter, the DP1 prostanoid receptor, the tachykinin NK1, NK2 or NK3 receptors, the CXCR4 chemokine receptor and the VEGFR1, VEGFR2 or VEGFR3 receptor.

In another embodiment, the selectivity agent specifically binds to a receptor which is expressed in the glia. In a preferred embodiment, the receptor which is expressed in the glia is selected from the group consisting of the formylpeptide FPR1 receptor, the formylpeptide FPR2 receptor, the formylpeptide FPR3 receptor and TLR7.

In a preferred embodiment, the selectivity agent which binds to the receptor is as shown in Table 2.

TABLE 2

Receptors and selectivity ligands specific for each receptor

| Target receptor | Selectivity agent |
| --- | --- |
| 5-HT1A | 5-carboxamidotryptamine maleate, indorenate hydrochloride, pindolol, Ro 60-0175 fumarate, S-(−)-Pindolol, F-15,599, flesinoxan, yohimbine, 1-(methylamino)-3-(1,2,3,4-tetrahydrocarbazol-9-yl)propan-2-ol, 4-[bis(4-ethoxyphenyl)methyl]piperidine, 6-tert-butyl-2-(piperazin-1-yl)-1,3-benzothiazole, 1-[2-(2-ethoxyphenyl)cyclopropyl]ethylamine, N-[[2-[(2-fluorophenyl)methoxy]phenyl]methyl]cyclopropanamine, (5,6-dimethoxy-2,3-dihydro-1H-inden-1-yl)methanamine, 4-(4-chloronaphthalen-1-yl)oxypiperidine, 2-methoxy-N-methyl-2-[3-(trifluoromethyl)phenyl]ethanamine, 1-(3,6-dichlorocarbazol-9-yl)-3-(propan-2-ylamino)propan-2-ol, N',N'-dimethyl-N-(2-methylquinolin-4-yl)ethane-1,2-diamine, 2-(2-methylphenyl)-4-piperazin-1-ylpyrazolo[1,5-a]pyrazine, 4-(1,4-diazepan-1-yl)-7-methylpyrrolo[1,2-a]quinoxaline, N-[2-[2-(4-bromophenyl)imidazo[1,2-a]benzimidazol-3-yl]ethyl]-2-methylpropan-2-amine, N-[3-(2-methoxy-4-methylphenoxy)propyl]butan-2-amine, 4-(2,4-dimethoxyphenyl)-N-(1-methylpiperidin-4-yl)-1,3-thiazol-2-amine, 2-(1-ethyl-5-methylindol-3-yl)ethanamine, [2-(3-fluorophenoxy)phenyl]methanamine, 3-(4-fluorophenyl)-3-(4-methoxyphenyl)propan-1-amine, anilopam hydrochloride, LY-165,163 ((1-[2-(4-aminophenyl)ethyl]-4-(3-trifluoromethylphenyl)-piperazine)) LY-165,163 C6-acyl, 8-OH-DPAT (8-Hydroxy-2-(di-n-propylamino)tetralin) |
| 5-HT1B | 5-carboxamidotryptamine maleate, 5-Nonyloxytryptamine oxalate, donitriptan hydrochloride, indorenate hydrochloride, pindolol, S-(−)-pindolol, triptans preferably Zolmitriptan, Eletriptan Sumatriptan, CP-93,129, CP-94,253, Dihydroergotamine, Eltoprazine, Ergotamine, Methysergide, RU 24969, Zolmitriptan, Eletriptan, Sumatriptan, 2-piperazin-1-ylquinoline, 1-(methylamino)-3-(1,2,3,4-tetrahydrocarbazol-9-yl)propan-2-ol, N',N'-dimethyl-N-(2-methylquinolin-4-yl)ethane-1,2-diamine, 4-(1,4-diazepan-1-yl)-7-methylpyrrolo[1,2-a]quinoxaline, 4-(2,4-dimethoxyphenyl)-N-(1-methylpiperidin-4-yl)-1,3-thiazol-2-amine |

TABLE 2-continued

Receptors and selectivity ligands specific for each receptor

| Target receptor | Selectivity agent |
|---|---|
| 5-HT1D | 5-carboxamidotryptamine maleate, CP-135,807, dihydroergotamine, ergotamine, methysergide, yohimbine donitriptan hydrochloride, triptans preferably almotriptan, eletriptan, frovatriptan, naratriptan, rizatriptan, sumatriptan or zolmitriptan |
| 5-HT1E | BRL-54443 |
| 5-HT1F | BRL-54443, lasmiditan, LY-334,370, naratriptan |
| 5-HT2A | DOI hydrochloride, Ro 60-0175 fumarate, TCB-2, α-Methyl-5-hydroxytryptamine maleate, Lisuride, yohimbine, 2-piperazin-1-ylquinoline, [2-(4-chlorophenyl)ethyl][(1-methyl-1H-indol-3-yl)methyl]amine, N-[[2-[(2-fluorophenyl)methoxy]phenyl]methyl]cyclopropanamine, (5,6-dimethoxy-2,3-dihydro-1H-inden-1-yl)methanamine, 4-(4-chloronaphthalen-1-yl)oxypiperidine, 1'-ethyl-6-methoxyspiro[2,3,4,9-tetrahydropyrido[3,4-b]indole-1,4'-piperidine], 4-(1,4-diazepan-1-yl)-7-methylpyrrolo[1,2-a]quinoxaline, N-[(2,5-difluorophenyl)methyl]-2-(3,4-dimethoxyphenyl)ethanamine, N-[(2,3-dimethoxyphenyl)methyl]-2,3-dihydro-1H-inden-2-amine, 1-(cyclopentylamino)-3-(3-methylphenoxy)propan-2-ol, 2-(1-ethyl-5-methylindol-3-yl)ethanamine, [2-(3-fluorophenoxy)phenyl]methanamine, 3-(1,3-benzodioxol-5-yloxymethyl)-4-(4-fluorophenyl)piperidine, 3-(4-fluorophenyl)-3-(4-methoxyphenyl)propan-1-amine |
| 5-HT2B | BW-723C86, Fenfluramine, Ro60-0175 fumarate |
| 5-HT2C | A-372,159, AL-38022A, Aripiprazole, Lorcaserin, Ro60-0175 fumarate and YM-348. |
| 5-HT3 | 1-Phenylbiguanide hydrochloride, B-HT 920, m-Chlorophenylbiguanide, SR 57227 hydrochloride, 2-Methyl-5-Hydroxytryptamine, Quipazine, RS-56812, Lerisetron (F-0930-RS), lerisetron-C6-acyl, |
| 5-HT4 | 5-Methoxytryptamine, BIMU-8, Cinitapride, Cisapride, Dazopride, Metoclopramide, Mosapride, Prucalopride, RS-67333, Renzapride, Tegaserod and Zacopride |
| 5-HT5a | 5-carboxamidotryptamine maleate, ergotamine |
| 5-HT6 | Ro 60-0175 fumarate, EMD-386,088, 4-(1,4-diazepan-1-yl)-7-methylpyrrolo[1,2-a]quinoxaline, 3-(4-fluorophenyl)-3-(4-methoxyphenyl)propan-1-amine |
| 5-HT7 | 5-carboxamidotryptamine maleate, AS-19, E-55888 and RA-7 |
| GAL1 | galanin, galanin-like peptide and M617 |
| GAL2 | AR-M 1896, galanin, galanin-like peptide, M1145 and M617 |
| GAL3 | galanin and galanin-like peptide |
| MC1 | adenocorticotropic hormone (ACTH), alpha-melanocyte-stimulating hormone, beta-melanocyte-stimulating hormone, gamma-melanocyte-stimulating hormone, melanotan-II and MS05 |
| MC2 | adenocorticotropic hormone (ACTH) |
| MC3 | adenocorticotropic hormone (ACTH), α-melanocyte-stimulating hormone (α-MSH), alpha-NDP-MSH, beta-melanocyte-stimulating hormone (β-MSH), gamma-melanocyte-stimulating hormone (γ-MSH) and melanotan-II |
| MC4 | adenocorticotropic hormone (ACTH), α-melanocyte-stimulating hormone (α-MSH), alpha-NDP-MSH, beta-melanocyte-stimulating hormone (β-MSH), gamma-melanocyte-stimulating hormone (γ-MSH) and melanotan-II |
| CRF1 | Corticotropin-releasing factor (CRF), sauvagine, stressin I, urocortin 1,, N-cyclohexyl-7-(4-methylphenyl)-5-phenylpyrrolo[2,3-d]pyrimidin-4-amine |
| CRF2 | Corticotropin-releasing factor (CRF), sauvagine, urocortin 1, urocortin 2 and urocortin 3 |
| FZD2 | Wnt-5a and Wnt |
| FZD3 | Wnt-3 and Wnt-5a |
| FZD4 | Wnt and norrin |
| FZD6 | Wnt-3a, wnt-4 and Wnt-5a |
| FZD8 | Wnt |
| FZD9 | Wnt |
| FZD10 | Wnt |
| alpha1A-adrenoceptor | Phenylephrine,, 2,3,3a,4,5,6-Hexahydro-1H-pyrazino[3,2,1-jk]carbazole, 2-piperazin-1-ylquinoline, 6-tert-butyl-2-(piperazin-1-yl)-1,3-benzothiazole, 2-(2-methylphenyl)-4-piperazin-1-ylpyrazolo[1,5-a]pyrazine, 4-(1,4-diazepan-1-yl)-7-methylpyrrolo[1,2-a]quinoxaline, N-(1,2-diphenylethyl)-4-methyl-4-(5-methylfuran-2-yl)pentan-2-amine, 3-(1,3-benzodioxol-5-yloxymethyl)-4-(4-fluorophenyl)piperidine, 3-(4-fluorophenyl)-3-(4-methoxyphenyl)propan-1-amine |
| alpha2-adrenoceptor | B-HT 933 dihydrochloride, Guanfacine hydrochloride |
| BB1 | gastrin-releasing peptide, GRP-27, GRP-14, GRP-10 and neuromedin B |
| BB2 | gastrin-releasing peptide, GRP-27, GRP-14, GRP-10, neuromedin B and bombesin |
| BB3 | bombesin |
| B2 | bradykinin, Phe$^8$Ψ(CH—NH)-Arg$^9$]-Bradykinin, kallidin and kinin |
| CT receptor-like CRL | adrenomedulin and CGRP |
| CCK2 | CCK-33, CCK-4. CCK-8, gastrin 17 and gastrin I |
| Y1 | BWX-46, neuropeptide Y, pancreatic polypeptide and peptide YY, 1,4-dimethyl-7,8,9,10-tetrahydro-6H-cyclohepta[b]quinolin-11-amine, 3-(4-fluorophenyl)-3-(4-methoxyphenyl)propan-1-amine |
| Y2 | neuropeptide Y, the pancreatic polypeptide and peptide YY (3-36) and peptide YY (PYY), 1,4-dimethyl-7,8,9,10-tetrahydro-6H-cyclohepta[b]quinolin-11-amine |
| Y4 | neuropeptide Y, the pancreatic polypeptide and the peptide YY |
| Y5 | BWX-46, neuropeptide Y, pancreatic polypeptide and peptide YY |
| NPFF1 | neuropeptide B-23, neuropeptide B-29, neuropeptide W-23 and the neuropeptide W-30 |
| NPFF2 | neuropeptide SF, the neuropeptide B-23, the neuropeptide B-29, the neuropeptide W-23 and the neuropeptide W-30 |
| NPFF1 | neuropeptide AF, the neuropeptide FF, the neuropeptide RFRP-1, the neuropeptide RFRP-3 and the neuropeptide SF |
| NPFF2 | neuropeptide AF, the neuropeptide FF, the neuropeptide RFRP-1 and the neuropeptide RFRP-3 |
| neurotensin NTSR1 receptor | ABS-201, contulakin-G, EISAI-2, JMV431, KH28, large neuromedin N, large neurotensin, neuromedin N and neurotensin |
| NTS2 | contulakin-G, JMV458, neuromedin N, neurotensin, xenin |
| opioid delta | beta-endorphin, deltorphin I, dynorphin 1-13, dynorphin A, dynorphin B, endorphin-1, Leu-enkephalin and Met-enkephalin,, 4-[3-[2-(4-methoxyphenyl)ethylamino]butyl]phenol |

TABLE 2-continued

Receptors and selectivity ligands specific for each receptor

| Target receptor | Selectivity agent |
|---|---|
| opioid kappa | alpha-neoendorphin, beta-endorphin, big dynorphin, dynorphin 1-13, dynorphin A, dynorphin B, Leu-enkephalin and Met-enkephalin,, 1,2,3,4,7,8,9,10-octahydro-[1]benzothiolo[2,3-b]quinolin-11-amine, 4-[3-[2-(4-methoxyphenyl)ethylamino]butyl]phenol |
| opioid mu | beta-endorphin, dynorphin 1-13, dynorphin A, dynorphin B, endomorphin-1, endomorphin-2, Leu-enkephalin, Met-enkephalin and PL-017 |
| sst1 | BIM 23053, CST-14, CST-17, L871,881, somatostatin-14 and SS-28 |
| sst2 | (1R,1'S,3'R/1R,1'R,3'S)-1-054,264, BIM 23053, CST-14, CST-17, L871,881, SRIF-14 and SRIF-28. |
| sst3 | CST-14, CST-17, L871881, SRIF-14 and SRIF-28 |
| sst4 | BIM 23053, CST-14, CST-17, L803,087 trifluoroacetate, L871,881, SRIF-14 and SRIF-28 |
| sst5 | BIM 23053, CST-14, CST-17, L871,881, SRIF-14 and SRIF-28 |
| FPR1 | cathepsin G, fMet-Ile-Phe-Leu, fMet-Leu-Phe, fMtet-Met-Tyr-Ala-Leu-Phe, WKYMVm and annexin I |
| FPR2 | amyloidogenic peptide, annexin I, Host-derived peptide, Microbe-derived peptide, Mitochondria-derived formyl-peptide, MMK1 and WKYMVm |
| FPR3 | amyloidogenic peptide, annexin I, Host-derived peptide, Microbe-derived peptide, Mitochondria-derived formyl-peptide, and WKYMVm |
| TLR7 | imiquimod |
| A1 | PD81723, 3-(4-fluorophenyl)-3-(4-methoxyphenyl)propan-1-amine |
| A2 | CV1808 |
| A2A | CGS21680, 3-(4-fluorophenyl)-3-(4-methoxyphenyl)propan-1-amine |
| ETa | endothelin-1, endothelin-2 and endothelin-3 |
| ETb | [Ala$^{1, 3, 11, 15}$]-endothelin, BQ-3020, endothelin-1, endothelin-2, endothelin-3 and IRL-1620 |
| MT1 | agomelatine and melatonin |
| MT2 | agomelatine and melatonin |
| AM1 | adrenomedullin, adrenomedullin 2/intermedin, alpha-CGRP, AM (11-50) and beta-CGRP |
| AM2 | adrenomedullin, adrenomedullin 2/intermedin, alpha-CGRP and beta-CGRP |
| AMY1 | adrenomedullin, adrenomedullin 2/intermedin, alpha-CGRP, amylin, beta-CGRP and calcitonin |
| AMY3 | adrenomedullin, adrenomedullin 2/intermedin, alpha-CGRP, amylin and calcitonin |
| CGRP | adrenomedullin, adrenomedullin 2/intermedin, alpha-CGRP and beta-CGRP |
| CT-R | adrenomedullin, adrenomedullin 2/intermedin, alpha-CGRP, amylin, beta-CGRP and calcitonin |
| Ghrelin receptor | tabimorelin hemifumarate, ghrelin, acyl ghrelin, Capromorelin, GHRP-2, GHRP-6, Hexarelin, Ipamorelin, MK-677, SM-130,686. |
| NPS receptor | neuropeptide S |
| OX1 | orexin A and orexin B |
| OX2 | orexin A and orexin B |
| OT | oxytocin and vasopressin |
| V1A | oxytocin and vasopressin |
| V1B | d[Cha$^4$]-AVP, desmopressin, oxytocin and vasopressin |
| V2 | desmopressin, oxytocin and vasopressin |
| AT2 | angiotensin I, antiotensin II, angiotensin III, CGP42112 and novokin |
| kisspeptin receptor | kisspeptin, kisspeptin-10, kisspeptin-13, kisspeptin-14, kisspeptin-15, kisspeptin-52, kisspeptin-54 and kisspeptin-9 |
| D1 | 6,7-ADTN, A68930 hydrochloride and pramipexole dihydrochloride |
| D2 | A68930 hydrochloride, B-HT 920, 4-[bis(4-ethoxyphenyl)methyl]piperidine, N-[[2-[(2-fluorophenyl)methoxy]phenyl]methyl]cyclopropanamine, (5,6-dimethoxy-2,3-dihydro-1H-inden-1-yl)methanamine, 4-(4-chloronaphthalen-1-yl)oxypiperidine, 4-[[[3-(4-methoxyphenyl)-3-phenylpropyl]amino]methyl]-N,N-dimethylaniline, N-[2-[2-(4-bromophenyl)imidazo[1,2-a]benzimidazol-3-yl]ethyl]-2-methylpropan-2-amine, 4-[3-[2-(4-methoxyphenyl)ethylamino]butyl]phenol, 1-(4-methoxyphenyl)-N-[[4-(trifluoromethyl)phenyl]methyl]propan-2-amine, {[1-(3,4-difluorophenyl)pyrrolidin-3-yl]methyl}[(2-methyl-1-phenyl-1H-imidazol-5-yl)methyl]amine, 2-(1-ethyl-5-methylindol-3-yl)ethanamine, [2-(3-fluorophenoxy)phenyl]methanamine, 3-(4-fluorophenyl)-3-(4-methoxyphenyl)propan-1-amine |
| QRFP | 26RGa and QFRP (P518). |
| NK1 | C14TKL-1, GR73632, hemokinin 1, eledoisin, kassinin, nerukinin A, neurokinin B, neuropeptide K, neuropeptide-alpha, phyllomedusin, septide, spantide I, sepantide II and substance P, 3-(4-fluorophenyl)-3-(4-methoxyphenyl)propan-1-amine, substance P sulfone, physalaemin, substance P 4-11, kassinin, substante P 6-11 |
| NK2 | [Lys$^5$, MeLeu$^9$, Nle$^{10}$]-NKA(4-10), GR64349, eledoisin, kassinin, nerukinin A, neurokinin B, neuropeptide K, neuropeptide-alpha, phyllomedusin, septide, spantide I, sepantide II and substance P, 3-(4-fluorophenyl)-3-(4-methoxyphenyl)propan-1-amine, hemokinin 1 |
| NK3 | senktide, eledoisin, kassinin, nerukinin A, neurokinin B, neuropeptide K, neuropeptide-alpha, phyllomedusin, septide, spantide I, sepantide II and substance P, 3-(4-fluorophenyl)-3-(4-methoxyphenyl)propan-1-amine, hemokinin 1, PD157672, Pro7neurokinin B |
| EphA1 | ephrin-A1 (EFNA1) |
| EphA2 | ephrin-A2 (EFNA2) |
| EphA3 | ephrin-A3 (EFNA3) |
| EphA4 | ephrin-A4 (EFNA4) |
| EphB1 | ephrin-B1 (EFNB1) |
| EphB2 | ephrin-B2 (EFNB2) |
| EphB3 | ephrin-A1 (EFNB3) |
| GlyT1 | sarcosine, Org 24598, NFPS, SSR-103800, N-methyl-SSR504734, GSK931145, NPTS |
| CXCR4 | SDF-1alpha, SDF-1beta, CXCL12 1-17, CXCL 1-9, isothiourea-1t, AMD3100, ALX40-4C, T140 |
| VEGFR1 | VRGFRA, VGFRB, SU 4312, axitinib, sunitinib malate |
| VEGFR2 | VRGFRA, VGFRB, SU 4312, axitinib, sunitinib malate |
| VEGFR3 | VRGFRA, VGFRB, SU 4312, axitinib, sunitinib malate |

A.2. The Nucleic Acid of the Conjugates of the Invention

The second component of the conjugates according to the present invention is a nucleic acid which is capable of specifically binding to a target molecule which is expressed in the same cell as the receptor. Typically, the nucleic acid of the invention is capable of inhibiting the function of the target molecule. Thus, if the target molecule is an mRNA, then the nucleic acid (typically a siRNA, a shRNA or an antisense nucleic acid) acts by inhibiting the translation of the mRNA leading to a decrease in the levels of the protein encoded by the mRNA. If the target nucleic acid is protein, then the nucleic acid (typically an aptamer) acts by inhibiting the activity of the protein.

The term "nucleic acid", as used herein, refers to a polymer having two or more deoxyribonucleotide, ribonucleotide or nucleotide analog molecules as well as molecules that are structurally similar to a native nucleic acid, but differ from the native nucleic acid (e.g., through chemical modification) at one or more of the nucleic acid backbone (e.g., phosphate in native nucleic acids), nucleic acid sugar (e.g., deoxyribose for native DNA and ribose in native RNA), and nucleic acid base (e.g., adenosine, cytosine, guanine, thymidine, or purine in native nucleic acids)

The oligonucleotide can be a double stranded or single stranded oligonucleotide including, without limitation, small interference RNAs (siRNA), small hairpin RNAs (shRNA), microRNAs (miRNA), antisense oligonucleotides or ribozymes. If double stranded nucleic acids are used, these comprise a first sense strand which is complementary to the target nucleic acid and a second antisense strand which is complementary to the sense, which allows the formation of the double stranded DNA by base pairing between the first and second strand.

The term "antisense strand" refers to the strand of a double stranded nucleic acid which includes a region that is substantially complementary to a target sequence Where the region of complementarity is not fully complementary to the target sequence, the mismatches are most tolerated outside nucleotides 2-7 of the 5' terminus of the antisense strand The term "sense strand," as used herein, refers to the strand of a dsRNA that includes a region that is substantially complementary to a region of the antisense strand.

The term small interfering RNA ("siRNA") refers to small inhibitory RNA duplexes that induce the RNA interference pathway. These molecules may vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand The term "siRNA" includes duplexes of two separate strands. As used herein, siRNA molecules are not limited to RNA molecules but further encompass nucleic acids with one or more chemically modified nucleotides, such as morpholinos.

The term "shRNA" or "short hairpin RNA" as used herein refers to a dsRNA where the two strands are connected by an uninterrupted chain of nucleotides between the 3'-end of one strand and the 5' end of the respective other strand to form a duplex structure.

The term "micro RNA" or "miRNA" refers to short single-stranded RNA molecules, typically of about 21-23 nucleotides in length capable of regulating gene expression. miRNAs may be synthetic (i.e., recombinant) or natural. Natural miRNAs are encoded by genes that are transcribed from DNA and processed from primary transcripts ("pri-miRNA") to short stem-loop structures ("pre-miRNA"), and finally to mature miRNA. Mature miRNA molecules are partially complementary to one or more mRNA molecules, and downregulate gene expression via a process similar to RNA interference, or by inhibiting translation of mRNA.

An "antisense sequence," as used herein includes antisense or sense oligonucleotides comprising a single-stranded nucleic acid sequence (either RNA or DNA) capable of binding to target mRNA (sense) or DNA (antisense) sequences. The ability to derive an antisense or a sense oligonucleotide, based upon a cDNA sequence encoding a given protein is described in, for example, Stein and Cohen, Cancer Res. 48:2659, (1988) and van der Krol et al., BioTechniques 6:958, (1988).

As used herein, the term "ribozyme" or "RNA enzyme" or "catalytic RNA" refers to an RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome, the ligase activity of a DNA ligase, and a number of other chemical reactions performed by conventional protein enzymes.

An "aptamer" as used herein refers to a nucleic acid ligand that binds to more than one site on a target molecule where binding is not "complementary," i.e., is not due to base-pair formation between a nucleic acid ligand and a target nucleic acid sequence. An aptamer can be designed which binds to any envisionable target, including polypeptides. Aptamers offer the utility for biotechnological and therapeutic applications as they offer molecular recognition properties that rival that of the commonly used biomolecule, antibodies. In addition to their selective recognition, aptamers offer advantages over antibodies as they can be engineered completely in a test tube, are readily produced by chemical synthesis, possess desirable storage properties, and elicit little or no immunogenicity in therapeutic applications. Aptamers can be synthesized through repeated rounds of in vitro partition, selection and amplification, a methodology known in the state of the art as "SELEX", (Systematic Evolution of Ligands by Exponential Enrichment) (Shamah et al, Acc. Chem. Res. 2008, 41 pp. 130-8). Alternatively, they can be synthesized, for example, by step-wise solid phase.

The nucleic acid of the invention may contain one or more modifications in the nucleobases, in the sugars and/or in the internucleotide linkages.

Modifications to one or more backbone residues of the nucleic acids may comprise one or more of the following: 2' sugar modifications such as 2'-O-methyl (2'-OMe), 2'-O-methoxyethyl (2'-MOE), 2'-O-methoxyethoxy, 2'-Fluoro (2'-F), 2'-AIlyI, 2'-O-[2-(methylamino)-2-oxoethyl], 2'-O—(N-methylcarbamate); 4' sugar modifications including 4'-thio, 4'-$CH_2$—O-2'-bridge, 4-$(CH_2)_2$—O-2'-bridge; Locked Nucleic Acid (LNA); Peptide Nucleic Acid (PNA); Intercalating nucleic acid (INA); Twisted intercalating nucleic acid (TINA); Hexitol nucleic acids (HNA); arabinonucleic acid (ANA); cyclohexane nucleic acids (CNA); cyclohexenyl-nucleic acid (CeNA); threosyl nucleic acid (TNA); Morpholino oligonucleotides; Gap-mers; Mix-mers; Incorporation Arginine-rich peptides; addition of 5'-phosphate to synthetic RNAs; RNA Aptamers (Que-Gewirth N S, Gene Ther. 2007 February; 14(4):283-91.); RNA Aptamers regulated with antidotes on the subject of the specific RNA aptamer (ref. Oney S, Oligonucleotides. 2007 Fall; 17(3): 265-74.) or any combinations thereof.

Modifications to one or more internucleoside linkages of the nucleic acids may comprise one or more of the following: Phosphorothioate, phosphoramidate, phosphorodiamidate, phosphorodithioate, phosphoroselenoate, phosphorodiselenoate, phosphoroanilothioate and phosphoranilidate, or any combinations thereof.

A Locked Nucleic Acid (LNA), often referred to as inaccessible RNA, is a modified RNA nucleotide. The ribose moiety of an LNA nucleotide is modified with an extra bridge connecting the 2' and 4' carbons (O2',C4'-methylene bridge). The bridge "locks" the ribose in the 3'-endo structural conformation, which is often found in the A-form of DNA or RNA. LNA nucleotides can be mixed with DNA or RNA bases in the nucleic acid whenever desired. Such oligomers are commercially available. The locked ribose conformation enhances base stacking and backbone preorganization. This significantly increases the thermal stability (melting temperature) and hybridization affinity of LNA-modified nucleic acids, besides having improved mismatch discrimination abilities. These properties make them very useful for antisense-based techniques. Further, LNA antimiR oligonucleotides have been tested in primates with encouraging results and low toxicity.

Peptide Nucleic Acid (PNA) is an artificially synthesized polymer similar to DNA or RNA and is used in biological research and medical treatments. PNA is not known to occur naturally. DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right. Since the backbone of PNA contains no charged phosphate groups, the binding between PNA/DNA strands is stronger than between DNA/DNA strands due to the lack of electrostatic repulsion. Mixed base PNA molecules are true mimics of DNA molecules in terms of base-pair recognition. PNA/PNA binding is stronger than PNA/DNA binding.

Intercalating nucleic acid (INA) is a modified nucleic acid analogue comprised of normal deoxyribonucleotides covalently linked to hydrophobic insertions. INA has high affinity for complementary DNA with stabilization of up to 11 degrees for each modification. INA has a higher specificity for a fully matched target over mismatched targets than normal DNA. Utilizing that INAs have higher affinity for DNA makes it possible to use shorter probes and thereby enhance specificity even further. Further, INA is a DNA selective oligonucleotide analogue, with a unique ability to discriminate between DNA and RNA. Even though INAs have high affinities for complementary DNA, it has a lower affinity for a complementary sequence of complementary INAs. Twisted intercalating nucleic acids are denoted TINA.

Hexitol nucleic acids (HNA) are oligonucleotides built up from natural nucleobases and a phosphorylated 1,5-anhydrohexitol backbone. Molecular associations between HNA and RNA are more stable than between HNA and DNA and between natural nucleic acids (dsDNA, dsRNA, DNA/RNA). Other synthetically modified oligonucleotides comprise ANA (arabinonucleic acid), CNA (cyclohexane nucleic acids), CeNA (cyclohexenylnucleic acid) and TNA (threosyl nucleic acid).

Morpholinos are synthetic molecules which are the product of a redesign of the natural nucleic acid structure. Structurally, the difference between morpholinos and DNA or RNA is that while Morpholinos have standard nucleobases, those bases are bound to 6-membered morpholine rings instead of deoxyribose/ribose rings and non-ionic phosphorodiamidate intersubunit linkages replace anionic phosphodiester linkages. Morpholinos are sometimes referred to as PMO (phosphorodiamidate morpholino oligonucleotide). The 6-membered morpholine ring has the chemical formula $O-(CH_2-CH_2)_2-NH$.

Gapmers are RNA-DNA-RNA chimeric oligonucleotide probes, where windows or 'gaps' of DNA are inserted into an otherwise normal or modified RNA oligonucleotide. This modification increases oligonucleotide stability in vivo and the avidity of the interaction of the probe with the target, so that shorter probes can be used effectively.

The nucleic acid of the conjugates of the invention are capable of specifically binding to a target molecule which is expressed in the same cell as the neurotransmitter transporter. The binding of the nucleic acid to the target molecule can occur via Watson-Crick interactions wherein the target molecule is a nucleic acid which contains a sequence which is complementary to the sequence of the nucleic acid. Alternatively, when the target molecule is a polypeptide, the nucleic acid of the conjugates of the invention can also interact with said molecule, in which case the nucleic acid is acting as an aptamer.

Wherein the nucleic acid which forms part of the conjugates of the invention is complementary to the nucleic acid sequence of the target mRNA, different criteria are available to the skilled person for selecting the most adequate nucleic acid. By way of example, when the nucleic acid forming part of the conjugate is a siRNA, this can be selected by scanning the mRNA sequence of the target for AA dinucleotides and recording the 19 nucleotides immediately downstream of the AA. Other methods can also been used to select the nucleic acid targets. In one example, the selection of the siRNA target sequence is purely empirically determined (see, e.g., Sui G et al., Proc. Natl. Acad. Sci. USA 99:5515-20 (2002)), as long as the target sequence starts with GG and does not share significant sequence homology with other genes as analyzed by BLAST search. In another example, a more elaborate method is employed to select the siRNA target sequences. This procedure exploits an observation that any accessible site in endogenous mRNA can be targeted for degradation by synthetic oligodeoxyribonucleotide/RNase H method (see, e.g., Lee N S et al., Nature Biotechnol. 20:500-05 (2002)).

Alternatively, the hairpin siRNA expression cassette is constructed to contain the sense strand of the target, followed by a short spacer, the antisense strand of the target, and 5-6 Ts as transcription terminator. The order of the sense and antisense strands within the siRNA expression constructs can be altered without affecting the gene silencing activities of the hairpin siRNA. In certain instances, the reversal of the order may cause partial reduction in gene silencing activities.

The length of nucleotide sequence being used as the stem of siRNA expression cassette can range, for instance, from 19 to 29. The loop size can range from 3 to 23 nucleotides. Other lengths and/or loop sizes can also be used.

In yet another embodiment, a 5' overhang in the hairpin siRNA construct can be used, provided that the hairpin siRNA is functional in gene silencing. In one specific example, the 5' overhang includes about 6 nucleotide residues.

In still yet another embodiment, the target sequence for RNAi is a 21-mer sequence fragment. The 5 end of the target sequence has dinucleotide "NA", where "N" can be any base and "A" represents adenine. The remaining 19-mer sequence has a GC content of between 35% and 55%. In addition, the remaining 19-mer sequence does not include any four consecutive A or T (i.e., AAAA or TTTT), three consecutive G or C (i.e., GGG or CCC), or seven "GC" in a row.

Additional criteria can also be used for selecting RNAi target sequences. For instance, the GC content of the remaining 19-mer sequence can be limited to between 45% and 55%. Moreover, any 19-mer sequence having three consecutive identical bases (i.e., GGG, CCC, TTT, or AAA) or a palindrome sequence with 5 or more bases is excluded. Furthermore, the remaining 19-mer sequence can be selected to have low sequence homology to other genes. In one specific example, potential target sequences are searched by BLASTN against NCBI's human UniGene cluster sequence database. The human UniGene database contains non-redundant sets of gene-oriented clusters. Each UniGene cluster includes sequences that represent a unique gene. 19-mer sequences producing no hit to other human genes under the BLASTN search can be selected. During the search, the e-value may be set at a stringent value (such as "1").

The effectiveness of the siRNA sequences, as well as any other RNAi sequence derived according to the present invention in silencing expression of the target gene, can be evaluated using various methods known in the art.

The terms "silence" and "inhibit the expression of," "down-regulate the expression of," "suppress the expression of," and the like, in as far as they refer to a target gene, herein refer to the at least partial suppression of the expression of a target gene, as manifested by a reduction of the amount of target mRNA, which may be isolated from a first cell or group of cells in which a target gene is transcribed and which has or have been treated such that the expression of a target gene is inhibited, as compared to a second cell or group of cells substantially identical to the first cell or group of cells but which has or have not been so treated (control cells). The degree of inhibition is usually expressed in terms of:

$$\frac{(\text{mRNA in control cells}) - (\text{mRNA in treated cells})}{(\text{mRNA in control cells})} * 100 \text{ percent}$$

Alternatively, the degree of inhibition may be given in terms of a reduction of a parameter that is functionally linked to target gene expression, e.g., the amount of protein encoded by a target gene or the number of cells displaying a certain phenotype. In principle, target genome silencing may be determined in any cell expressing the target, either constitutively or by genomic engineering, and by any appropriate assay. However, when a reference is needed in order to determine whether a given nucleic inhibits the expression of a target gene by a certain degree and therefore is encompassed by the instant invention, the assay provided in the Examples below and those known in the art shall serve as such reference. For example, in certain instances, expression of a target gene is suppressed by at least about 5 percent, 10 percent, 15 percent, 20 percent, 25 percent, 30 percent, 35 percent, 40 percent, 45 percent, or 50 percent by administration of the double-stranded oligonucleotide. In some embodiments, a target gene is suppressed by at least about 60 percent, 70 percent, or 80 percent by administration of the double-stranded oligonucleotide. In some embodiments, the target gene is suppressed by at least about 85 percent, 90 percent, or 95 percent by administration of the double-stranded oligonucleotide.

For instance, the nucleic acid sequence according to the present invention can be introduced into a cell that expresses the target gene. The mRNA level of the target gene in the cell can be detected by using RT-PCR, Northern blot or any other standard methods). Alternatively, the level of the polypeptide encoded by the target mRNA can be measured using Western blot, ELISA or any other immunological or non-immunological method. A substantial change in the expression level of mRNA or of the protein encoded by the target gene after the introduction of the siRNA sequence is indicative of the effectiveness of the siRNA sequence in suppressing the expression of the target gene. In one specific example, the expression levels of other genes are also monitored before and after the introduction of the siRNA sequence. An siRNA sequence which has inhibitory effect on target gene expression but does not significantly affect the expression of other genes can be selected. In another specific example, multiple siRNA or other RNAi sequences can be introduced into the same target cell. These siRNA or RNAi sequences specifically inhibit target gene expression but not the expression of other genes. In yet another specific example, siRNA or other RNAi sequences that inhibit the expression of the target gene and other gene or genes can be used.

The skilled person will appreciate that the specific choice of nucleic acid molecule which is incorporated into the conjugates of the invention will depend on the type of selectivity agent present in the conjugate. Thus, the nucleic acid will be specific for a target molecule which is expressed in the cells which express the neurotransmitter transporter which is specifically bound by the selectivity agent. In those cases wherein the nucleic acid is an antisense, a siRNA, a shRNA, a miRNA or a ribozyme, the nucleic acid acts by base-pairing with the target molecule, in which case the target molecule is an mRNA. If the nucleic acid is an aptamer, the target molecule is the polypeptide encoded by said mRNA.

The skilled person will appreciate that the nucleic acid of the invention specific towards a target mRNA can be selected using any of the methods mentioned above and tested for its ability to induce a substantial decrease in the levels of the corresponding mRNA. These regions correspond to regions which are highly conserved among different species or regions corresponding to non-coding regions of the primary transcript in order to avoid potential interference with translation complexes inside the coding region.

Methods for pairwise alignment of two given nucleic acid sequences are widely known to the skilled person and can be carried out by standard algorithms of the type BLASTN [BLAST Manual, Altschul, S., et al., NCBI NLM NIH Bethesda, Md. 20894, Altschul, S., et al., J. Mol. Biol. 215: 403-410 (1990)] using the default parameters. Methods for the alignment of multiple nucleic acid sequences can be carried out using standard algorithms of the type CLUSTALW (Thompson J D et al, Nucleic Acids Res, 1994, 22:4673-4680) using the default parameters.

In a preferred embodiment, wherein the selectivity agent specifically binds a receptor which is expressed in the hypothalamus, then the nucleic acid is specific for the mRNA of the suppressor of cytokine signaling 3 (SOCS3), protein-tyrosine phosphatase 1B (PTP1B), CB1, interleukin beta 1 (IL1B), neuropeptide Y (NPY), neuropeptide Y1, neuropeptide Y5 and the ghrelin receptor.

The term "SOCS3" refers to naturally occurring or recombinant forms of the polypeptide "Suppressor of cytokine signaling-3", which is involved in transducing the signaling by leptin by means of its binding to the phosphorylated leptin receptor through its SH2 domain and inhibiting Jak tyrosine kinase activity through its N-terminal kinase inhibitory region, which functions as pseudosubstrate. Different orthologs of the SOSC3 polypeptide are shown in the NCBI database under accession numbers NP_003946, NP_031733, and NP_446017 for human, mouse and rat protein sequences, respectively, (Oct. 21, 2013). Different orthologs of the SOCS3 polypeptide are shown in the NCBI database under accession numbers NM_003955.2, NM_007707.2, and NM_053565.1 for human, mouse, and rat polynucleotide sequences (Oct. 21, 2013).

Suitable SOCS3-specific siRNA that can be used in the present invention are, e.g. those shown in WO2012082765. Suitable SOCS3-specific antisense nucleic acids that can be used in the present invention are, e.g. those shown in US2010135952, US2004087530, in Raghavendra Rao et al., (J Neurochem., 2002, 83, 1072-1086), Fox et al., (J. Immunol., 2003, 170, 3679-3687).

In another preferred embodiment, the nucleic acid specific for SOCS3 is a gapmer having the sequence GUGGCGCTGGTCCGAGCTGT (SEQ ID NO:1), wherein the underlined blocks correspond to 2'-O-methyl modified nucleotides.

In another preferred embodiment, the nucleic acid specific for SOCS3 is a siRNA having the a sense strand with the sequence cuuuucgcugcagagugacTT (SEQ ID NO:2) and an antisense strand having the sequence gucacucugcagcgaaaagTT (SEQ ID NO:3).

The term PTP1B, as used herein, refers to protein tyrosine phosphatase 1B which has been identified as a negative regulator of the insulin response. Isolated PTP-1B dephosphorylates the insulin receptor in vitro (Tonks, N. K., 1988, J. Biol. Chem., 263: 6731-6737). PTP-1B dephosphorylation of multiple phosphotyrosine residues of the insulin receptor proceeds sequentially and with specificity for the three tyrosine residues that are critical for receptor autoactivation (Ramachandran, C. 1992, Biochemistry, 31: 4232-4238). In addition to insulin receptor dephosphorylation, PTP-1B also dephosphorylates the insulin related subtrate 1 (IRS-1), a principal substrate of the insulin receptor (Lammers, R., 1993, J. Biol. Chem. 268: 22456-22462). The human ortholog of the PTP-1B polypeptide is shown in the NCBI database under Genbank Accession number NM_002827 (Oct. 21, 2013).

Suitable PTP-1B sequences that can be targeted by the nucleic acids according to the invention are shown in Table 2 of WO0200307088. Suitable PTP 1B-specific siRNAs are showin in Table 2 of WO200307088.

In another preferred embodiment, the nucleic acid specific for PTP-1B is a gapmer having the sequence GCUCCTTCCACTGATCCUGC (SEQ ID NO:4), wherein the underlined blocks correspond to 2'-O-methyl modified nucleotides and the bold block corresponds to a nucleotides connected by phosphorothioate.

In another preferred embodiment, the nucleic acid specific for PTP-1B is a siRNA having the a sense strand with the sequence ccgcaucauggagaaaggcTT (SEQ ID NO:5) and an antisense strand having the sequence gccuuucuccaugaugcggTT (SEQ ID NO: 6), wherein the capitalized sequences correspond to the overhangs in the duplex siRNA.

In another preferred embodiment, wherein the selectivity agent specifically binds a receptor which is expressed in the mesencephalon, then the nucleic acid is specific for dopamine D1, D2 or D3 receptor, for the dopamine transporter or for alpha-synuclein.

In another preferred embodiment, wherein the selectivity agent specifically binds a receptor which is expressed in the brainstem, then the nucleic acid is specific for the mRNA selected from the group consisting of the serotonine 5-HT1A receptor, the serotoine 5-HT2C receptor, the SERT (serotonine transporter), the alpha1A-adrenoceptor, the angiotensin converting enzyme, G protein β3, the 5-HT2C receptor, interleukin 1β, monoamine oxidase A, the cannabinoid CB1 receptor and α-synuclein.

In a more preferred embodiment, wherein the selectivity agent specifically binds a receptor which is expressed in the brainstem, then the nucleic acid is specific for the mRNA of serotonine 5-HT1A receptor.

The term "serotonine 5-HT1A receptor" refers to a subtype of 5-HT receptor that binds the endogenous neurotransmitter serotonin. The human sequence of serotonine 5-HT1A receptor is shown in the Uniprot database with the accession number P08908 (Oct. 21, 2013).

In a preferred embodiment, the nucleic acid specific for serotonine 5-HT1A receptor is a siRNA. In another preferred embodiment, the nucleic acid specific for serotonine 5-HT1A receptor is a siRNA having the sense strand with the sequence ggugcucaacaaguggacuTT (SEQ ID NO:11) and an antisense strand having the sequence aguccacuuguugagcaccTT (SEQ ID NO: 12).

In another preferred embodiment, wherein the selectivity agent specifically binds a receptor which is expressed in the cortex, then the nucleic acid is specific for a the mRNA selected from the group consisting of a gene product encoded in chromosome 21, for amyloid precursor protein, presenilin 1, presenilin 2, Apolipoprotein E, cyclin-dependent kinase 5, glycogen synthase kinase 3, the microtubule affinity-regulating kinase A2, dopamine D4 receptor, acetylcholinesterase, adenosine A2 receptor, CB1, catechol-O-methyl transferase, histamine N-methyltransferase, H3, 5-HT6, phosphodiesterase 10A, phosphodiesterase 1B, phosphodiesterase 1C, phosphodiesterase 2A, phosphodiesterase 4A, phosphodiesterase 4B, phosphodiesterase 4D, phosphodiesterase 7A, phosphodiesterase 7B, phosphodiesterase 8B, phosphodiesterase 9B, dopamine receptors D1, D2 or D3, the uncharacterized protein C9orf72, progranulin, Tau, Huntingtin, α-synuclein, kynuerine aminotransferase and miR-137.

In another preferred embodiment, wherein the selectivity agent specifically binds a receptor which is expressed in the cerebellum, then the nucleic acid is specific for a the mRNA selected from the group consisting of atrophin-1, Fragile X Mental retardation 1, G-protein coupled receptor 55, 1p36, ataxin 1, ataxin 10, tubulin kinase 2, PPP2R2B, Kv3.3 channel, Protein kinase C gamma, inositol receptor, Ataxin 17, interferon-related developmental regulator gene 1, Ataxin 19, Ataxin 2, Ataxin 20, Ataxin 21, Ataxin 22, dynorphin, Ataxin 25, Ataxin 26, Fibroblast growth factor14, mitochondrial metalloprotease complex, ataxin 29, ataxin 3, ataxin 30, Thymidine kinase 2 & Brain expressed associated with NEDD4, ataxin 32, ataxin 33, gene product encoded by 16p12.3-q16.2, transglutaminase, Nuclear Protein 56, Ataxin 4, Ataxin 5, alpha1A subunit of P/Q calcium channel, Ataxin 7 and Kelch-like protein 1.

In a more preferred embodiment, wherein the selectivity agent specifically binds a receptor which is expressed in the cerebellum, then the nucleic acid is specific for the mRNA of Ataxin 1.

The term "Ataxin 1" refers to Spinocerebellar ataxia type 1 protein, a chromatin-binding factor that repress Notch signaling in the absence of Notch intracellular domain by acting as a CBF1 corepressor. Different orthologs of the Ataxin 1 polypeptide are shown in the NCBI database under accession numbers NP_000323 and NP_001186233 for human and mouse respectively (Oct. 21, 2013).

In a preferred embodiment, the nucleic acid specific for Ataxin 1 is a siRNA. In another preferred embodiment, the nucleic acid specific for Ataxin 1 is a siRNA having the sense strand with the sequence gaucuaacgugggcaaguaTT (SEQ ID NO:9) and an antisense strand having the sequence uacuugcccacguuagaucTT (SEQ ID NO: 10).

In another preferred embodiment, wherein the selectivity agent specifically binds a receptor which is expressed in the striatum, then the nucleic acid is specific for a the mRNA selected from the group consisting of the dopamine D1, D2 or D3 receptors, the serotonine 5-HT2C receptor, the adenosine A2A receptor, Huntingtin, and the dopamine transporter.

In another preferred embodiment, wherein the selectivity agent specifically binds a receptor which is expressed in the hippocampus, then the nucleic acid is specific for a the mRNA selected from the group consisting of a gene product encoded in chromosome 21, the amyloid precursor protein, presenilin 1, presenilin 2, Apolipoprotein E, cyclin-dependent kinase 5, glycogen synthase kinase 3, the microtubule affinity-regulating kinase, the serotonine 5-HT1A receptor, the adenosine A1 receptor, acetylcholinesterase, cannabinoid CB1 receptor, catechol-O-methyl transferase, histamine N-methyltransferase, H3, 5-HT6, nitric oxide synthase, phosphodiesterase 10A, phosphodiesterase 1B, phosphodiesterase 1C, phosphodiesterase 2A, phosphodiesterase 4A, phosphodiesterase 4B, phosphodiesterase 4D, phosphodiesterase 7A, phosphodiesterase 7B, phosphodiesterase 8B and phosphodiesterase 9A.

In a more preferred embodiment, wherein the selectivity agent specifically binds a receptor which is expressed in the cerebellum, then the nucleic acid is specific for the mRNA of glycogen synthase kinase 3beta.

The term "glycogen synthase kinase 3beta" refers to a serine/threonine protein kinase that mediates the addition of phosphate molecules onto serine and threonine amino acid residues. The human sequence of glycogen synthase kinase 3 beta is shown in the Uniprot database with the accession number P49841 (Oct. 21, 2013).

In a preferred embodiment, the nucleic acid specific for glycogen synthase kinase 3beta is a siRNA. In another preferred embodiment, the nucleic acid specific for glycogen synthase kinase 3beta is a siRNA having the sense strand with the sequence ggcaccagaguugaucuuugTT (SEQ ID NO:13) and an antisense strand having the sequence caaagaucaacucuggugccTT (SEQ ID NO: 14).

In another preferred embodiment, wherein the selectivity agent specifically binds a receptor which is expressed in the spinal cord, then the nucleic acid is specific for a the mRNA selected from the group consisting of superoxide dismutase 1, Alsin, Probable helicase senataxin, RNA-binding protein FUS, cesicle-associated membrane protein-associated protein B/C, Angiogenin, TAR DNA-binding protein 43, Polyphosphoinositide phosphatase, Optineurin, Ataxin-2, valosin-containing protein, reticulon 4, Nav1.7, Nav1.8, Cav2.2, COX-2, kappa and Survival motor neuron protein.

A.3. Linker Regions of the Conjugates of the Invention

The nucleic acid and the selectivity agent may be directly coupled. However, it is preferred that both moieties are linked by a connecting group.

The terms "connecting group", "linker", "linking group" and grammatical equivalents thereof are used herein to refer to an organic moiety that connects two parts of a compound. The selectivity agent can be attached to any sense or antisense nucleotide within the nucleic acid, but it can be preferably coupled through the 3' terminal nucleotide and/or 5' terminal nucleotide. An internal conjugate may be attached directly or indirectly through a linker to a nucleotide at a 2' position of the ribose group, or to another suitable position.

In the case wherein the nucleic acid is a double-stranded nucleic acid, the conjugate can be attached to the sense 3' terminal nucleotide, the sense 5' terminal nucleotide, the antisense 3' terminal nucleotide, and/or the antisense 5' terminal nucleotide.

Though not wishing to be limited by definitions or conventions, in this application the length of the linker is described by counting the number atoms that represent the shortest distance between the atom that joins the conjugate moiety to the linker and the oxygen atom of the terminal phosphate moiety associated with the oligonucleotide through which the linker is attached to the oligonucleotide. In cases where the linker comprises one or more ring structures, counting the atoms around the ring that represent the shortest path is preferred.

Suitable linker groups for use in the present invention include, without limitation, modified or unmodified nucleotides, nucleosides, polymers, sugars, carbohydrates, polyalkylenes such as polyethylene glycols and polypropylene glycols, polyalcohols, polypropylenes, mixtures of ethylene and propylene glycols, polyalkylamines, polyamines such as polylysin and spermidine, polyesters such as poly(ethyl acrylate), polyphosphodiesters, aliphatics, and alkylenes. Moreover, linkers/linker chemistries that are based on omega-amino-1,3-diols, omega-amino-1,2-diols, hydroxyprolinols, omega-amino-alkanols, diethanolamines, omega-hydroxy-1,3-diols, omega-hydroxy-1,2-diols, omega-thio-1,3-diols, omega-thio-1,2-diols, omega-carboxy-1,3-diols, omega-carboxy-1,2-diols, co-hydroxy-alkanols, omega-thio-alkanols, omega-carboxy-alkanols, functionalized oligoethylene glycols, allyl amine, acrylic acid, allyl alcohol, propargyl amine, propargyl alcohol, and more, can be applied in this context to generate linkers of the appropriate length.

The linker may also confer other desirable properties on the oligonucleotide conjugate improved aqueous solubility, optimal distance of separation between the conjugate moiety and the oligonucleotide, flexibility (or lack thereof), specific orientation, branching, and others.

Preferably, said connecting group has the following structure

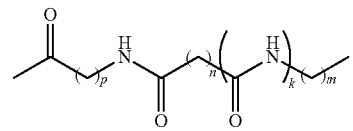

wherein
m, n and p are selected from 0, 1, 2, 3, 4, 5, 6, 7, 8, 9, 10, 11, 12 and 13,
wherein the sum of m+n+p is an integer number selected from 7, 8, 9, 10, 11, 12, 13, 14, 15, 16, 17 and 18 and
wherein k is 0 or 1.
In a preferred embodiment, p is 5, n is 2, k is 1 and m is 6 giving a linker having the structure:

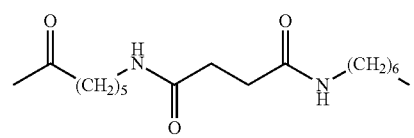

In another preferred embodiment, p is 5, n and k are 0 and m is 6 giving a linker having the structure:

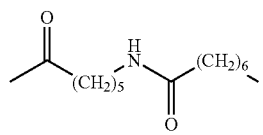

In a particular embodiment, the linker comprises more than one coupling for the selectivity agent. In a preferred embodiment, the linker is a bivalent or trivalent linker, i.e. 2 or 3 molecules of selectivity agent can be coupled, respectively.

In the case wherein more than one molecule of selectivity agent are coupled to the nucleic acid through a linker, said molecules can represent the same or different selectivity agents.

In a particular embodiment, the bivalent or trivalent linker has the following formula:

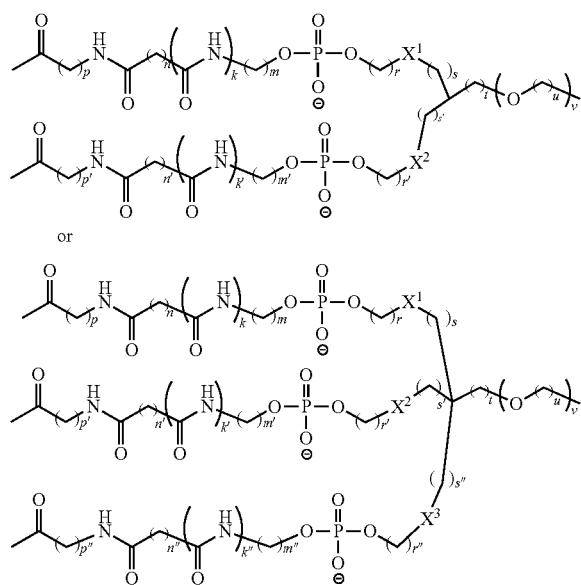

wherein
m, m', m", n, n', n", p, p', p", r, r', r", s, s', s", t and u are independently selected from 0, 1, 2, 3, 4, 5, 6, 7, 8, 9, 10, 11, 12 and 13;
k, k', k" and v are independently selected from 0 and 1; and $X^1$, $X^2$ and $X^3$ are independently selected from $CH_2$, O, S, NH, CO, C(O)O and C(O)NH.

Depending on the values of the above mentioned groups, branched linkers can be symmetrical or asymmetrical.

In a particular embodiment, the linker is a bivalent linker as shown above wherein p and p' are 5, n and n' are 2, k and k' are 1 and m and m' are 6. In a particular embodiment, the linker is a bivalente linker wherein p and p' are 5, n, n', k and k' are 0 and m and m' are 6.

In a particular embodiment, the linker is a bivalent linker as shown above wherein r and r' are 4, s and s' are 1, t and v are 0 and $X^1$ and $X^2$ represent C(O)NH. In another embodiment, the linker is a bivalent linker wherein r is 2, r' is 0, s is 1, s' is 0, t and v are 0 and $X^1$ and $X^2$ represent $CH_2$.

In a particular embodiment, the linker is a bivalente linker wherein p and p' are 5, n and n' are 2, k and k' are 1, m and m' are 6, r and r' are 4, s and s' are 1, t and v are 0 and $X^1$ and $X^2$ represent C(O)NH.

In another embodiment, the linker is a bivalente linker wherein p and p' are 5, n and n' are 2, k and k' are 1, m and m' are 6, r is 2, r' is 0, s is 1, s' is 0, t and v are 0 and $X^1$ and $X^2$ represent $CH_2$.

In another embodiment, the linker is a bivalente linker wherein p and p' are 5, n, n', k and k' are 0 and m and m' are 6, r and r' are 4, s and s' are 1, t and v are 0 and $X^1$ and $X^2$ represent C(O)NH.

In another embodiment, the linker is a bivalente linker wherein p and p' are 5, n, n', k and k' are 0 and m and m' are 6, r is 2, r' is 0, s is 1, s' is 0, t and v are 0 and $X^1$ and $X^2$ represent $CH_2$.

In a particular embodiment, the linker is a trivalent linker as shown above wherein p, p' and p" are 5, n, n' and n" are 2, k, k' and k" are 1 and m, m' and m" are 6. In a particular embodiment, the linker is a trivalent linker wherein p, p' and p" are 5, n, n', n", k, k' and k" are 0 and m, m' and m" are 6.

In a particular embodiment, the linker is a trivalent linker as shown above wherein r, r' and r" are 3, s, s' and s" are 1, t is 1, v is 0 and $X^1$, $X^2$ and $X^3$ represent O.

In another embodiment, the linker is a trivalent linker wherein r, r' and r" are 3, s, s' and s" are 1, t is 1, u is 3, v is 1 and $X^1$, $X^2$ and $X^3$ represent O.

In a particular embodiment, the linker is a trivalent linker wherein p, p' and p" are 5, n, n' and n" are 2, k, k' and k" are 1, m, m' and m" are 6, r, r' and r" are 3, s, s' and s" are 1, t is 1, v is 0 and $X^1$, $X^2$ and $X^3$ represent O.

In another embodiment, the linker is a trivalent linker wherein p, p' and p" are 5, n, n' and n" are 2, k, k' and k" are 1, m, m' and m" are 6, r, r' and r" are 3, s, s' and s" are 1, t is 1, u is 3, v is 1 and $X^1$, $X^2$ and $X^3$ represent O.

In another embodiment, the linker is a trivalent linker wherein p, p' and p" are 5, n, n', n", k, k' and k" are 0, m, m' and m" are 6, r, r' and r" are 3, s, s' and s" are 1, t is 1, v is 0 and $X^1$, $X^2$ and $X^3$ represent O.

In another embodiment, the linker is a trivalent linker wherein p, p' and p" are 5, n, n', n", k, k' and k" are 0, m, m' and m" are 6, r, r' and r" are 3, s, s' and s" are 1, t is 1, u is 3, v is 1 and $X^1$, $X^2$ and $X^3$ represent O.

A particular preferred linking group according to the present invention has the following structure:

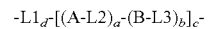

wherein:
A and B represent monomer units independently selected from the group consisting of a monosaccharide, an alkyl chain and a ($C_2$-$C_{20}$) alkylene glycol;
a and b are integers ranging from 0 to 50;
c is an integer ranging from 0 and 30;
L1, L2 and L3 are linking compounds independently selected from the group consisting of phosphodiester, phosphorothioate, carbamate, methylphosphonate, guanidinium, sulfamate, sulfamide, formacetal, thioformacetal, sulfone, amide and mixtures thereof; and
d is 0 or 1.

In a particular embodiment, the linking group has the structure:

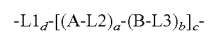

wherein b and d are 0, c is 1, A is an alkyl chain and L2 is a phosphodiester bond.

A.4. Further Modifications of the Conjugates of the Invention

Another modification of the conjugates of the invention involve chemically linking to the nucleic acid or to the protecting group one or more moieties or conjugates which enhance the activity, cellular distribution or cellular uptake of the nucleic acid. Such moieties include but are not limited to lipid moieties such as a cholesterol moiety (Letsinger et al, Proc. Natl. Acid. Sci. USA, 199, 86, 6553-6556), cholic acid (Manoharan et al, Biorg. Med. Chem. Let., 1994 4 1053-1060), a thioether, e.g., beryl-S-tritylthiol (Manoharan et al, Ann. N.Y. Acad. Sci., 1992, 660, 306-309; Manoharan et al, Biorg. Med. Chem. Let., 1993, 3, 2765-2770), a thiocholesterol (Oberhauser et al, Nucl. Acids Res., 1992, 20, 533-538), an aliphatic chain, e.g., dodecandiol or undecyl residues (Saison-Behmoaras et al, EMBO J, 1991, 10, 1111-1118; Kabanov et al, FEBS Lett., 1990, 259, 327-330; Svinarchuk et a/., Biochimie, 1993, 75, 49-54), a phospholipid, e.g., di-hexadecyl-rac-glycerol or triethyl-ammonium 1,2-di-O-hexadecyl-rac-glycero-3-Hphosphonate (Manoharan et al, Tetrahedron Lett., 1995, 36, 3651-3654; Shea et al, Nucl. Acids Res., 1990, 18, 3777-3783), a polyamine or a polyethylene glycol chain (Manoharan et al., Nucleosides and Nucleotides, 1995, 14, 969-973), or adamantane acetic acid (Manoharan et al., Tetrahedron Lett., 1995, 36, 3651-3654), a palmityl moiety (Mishra et ai, Biochim Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Alternatively, the moiety capable of enhancing cellular distribution may be a low molecular weight compound or polypeptide which is capable of being specifically translocated across biological barriers by the use of receptor-mediated endocytosis using specific transporters present in said biological barriers. A wide array of uptake receptors and carriers, with a even wider number of receptor-specific ligands, are known in the art. Preferred ligands for receptors that mediates endocytosis and/or transcytosis for use in accordance with present invention include e.g. ligands for, or that specifically bind to the thiamine transporter, folate receptor, vitamin B 12 receptors, asialoglycoprotein receptors, alpha(2,3)-sialoglycoprotein receptor (with e.g., the FC5 and FC44 nanobodies consisting of llama single-domain antibodies (sdAbs) as receptor-specific ligands), transferrin-1 and -2 receptors, scavenger receptors (class A or B, types I, II or III, or CD36 or CD163), low-density lipoprotein (LDL) receptor, LDL-related protein 1 receptor (LRP1, type B), the LRP2 receptor (also known as megalin or glycoprotein 330), diphtheria toxin receptor (DTR, which is the membrane-bound precursor of heparin-binding epidermal growth factor-like growth factor (HB-EGF)), insulin receptor, insulin-like growth factors (IGF) receptors, leptin receptors, substance P receptor, glutathione receptor, glutamate receptors and mannose 6-phosphate receptor.

Preferred ligands that bind to these receptors, for use in accordance with the present invention include e.g. ligands selected from the group consisting of: lipoprotein lipase (LPL), alpha2-macroglobulin (alpha2M), receptor associated protein (RAP), lactoferrin, desmoteplase, tissue- and urokinase-type plasminogen activator (tPA/uPA), plasminogen activator inhibitor (PAI-I), tPA/uPA:PAI-1 complexes, melanotransferrin (or P97), thrombospondin 1 and 2, hepatic lipase, factor Vila/tissue-factor pathway inhibitor (TFPI), factor Villa, factor IXa, Abeta1-40, amyloid-beta precursor protein (APP), C1 inhibitor, complement C3, apolipoproteinE (apoE), *pseudomonas* exotoxin A, CRM66, HIV-I Tat protein, rhinovirus, matrix metalloproteinase 9 (MMP-9), MMP-13 (collagenase-3), spingolipid activator protein (SAP), pregnancy zone protein, antithrombin III, heparin cofactor II, alpha1-antitrypsin, heat shock protein 96 (HSP-96), platelet-derived growth factor (PDGF), apolipoproteinJ (apoJ, or clusterin), ABETA bound to apoJ and apoE, aprotinin, angio-pepl, very-low-density lipoprotein (VLDL), transferrin, insulin, leptin, an insulin-like growth factor, epidermal growth factors, lectins, peptidomimetic and/or humanized monoclonal antibodies or peptides specific for said receptors (e.g., sequences HAIYPRH (SEQ ID NO: 7) and THRPPMWSPVWP (SEQ ID NO: 8) that bind to the human transferrin receptor, or anti-human transferrin receptor (TfR) monoclonal antibody A24), hemoglobin, non-toxic portion of a diphtheria toxin polypeptide chain, all or a portion of the diphtheria toxin B chain (including DTB-His (as described by Spilsberg et al., 2005, Toxicon., 46(8):900-6)), all or a portion of a non-toxic mutant of diphtheria toxin CRM197, apolipoprotein B, apolipoprotein E (e.g., after binding to polysorb-80 coating on nanoparticles), vitamin D-binding protein, vitamin A/retinol-binding protein, vitamin B12/cobalamin plasma carrier protein, glutathione and transcobalamin-B 12.

In a particular embodiment, the conjugate of the invention further comprises a group that facilitates the transport across biological membranes of the conjugate. Preferably, the group is amphipathic. An exemplary agents include, without limitation, penetratin, the fragment of the Tat protein comprising amino acids 48-60, the signal sequence based peptide, PVEC, transportan, amphiphilic model peptide, Arg9, bacterial cell wall permeating peptide, LL-37, cecropin P1, α-defensin, β-defensin, bactenectin, PR-39 and indolicidin. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long (see Table 4, for example).

In another particular embodiment of the invention, the conjugate of the invention further comprises an endosomolytic ligand. Endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In certain embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GAL4 peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68), the INF-7 peptide, the Inf HA-2 peptide, the diINF-7 peptide, the diINF3 peptide, the GLF peptide, the GALA-INF3 peptide and the INF-5 peptide. In certain embodiments, the endosomolytic component may contain a chemical group (e.g., an amino acid) which will undergo a change in charge or protonation in response to a change in pH. The endosomolytic component may be linear or branched.

A.5. Protecting Groups

The nucleic acids forming part of the conjugates of the invention have to be preserved from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Preferably, the nucleic acids are chemically modified by the presence of a group which prevents nuclease-mediated degradation.

For purposes of the present invention, "cap structure" or "protecting group" shall be understood to mean chemical modifications, which have been incorporated at either terminus of the oligonucleotide. Non-limiting examples of the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Details are described in WO97/26270, incorporated by reference herein. The 3'-cap includes, for example, 4',5'-methylene nucleotide; 1-(beta-D-erythrofuranosyl) nucleotide: 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inveiled abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties. See also Beaucage and Iyer, 1993, Tetrahedron 49, 1925; the contents of which are incorporated by reference herein.

In a preferred embodiment, the cap structure which is attached to the nucleic acid sequence of the conjugates of the invention has the following general structure:

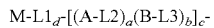

wherein:
M is H. a lipid moiety or a targeting group as defined above;
A and B represent monomer units independently selected from the group consisting of a monosaccharide and a $(C_2-C_{20})$ alkylene glycol;
L1, L2 and L3 are linking compounds independently selected from the group consisting of phosphodiester, phosphorothioate, carbamate, methylphosphonate, guanidinium, sulfamate, sulfamide, formacetal, thioformacetal, sulfone, amide and mixtures thereof;
a and b are integers ranging from 0 to 50;
c is an integer ranging from 0 and 30;
d is an integer which is at least 1.

A lipid moiety, as used herein, refers to a group of organic compounds that has lipophilic or amphipathic properties, including, but not limited to, fats, fatty oils, essential oils, waxes, steroids, sterols, phospholipids, glycolipids, sulpholipids, aminolipids, chromolipids (lipochromes), and fatty acids, The term "lipid" encompasses both naturally occurring and synthetically produced lipids. Lipid moieties usually increase lipophilic properties of the oligonucleotide and facilitate the intracellular uptake in vivo of the oligonucleotide construction. Suitable lipids that can be used include fatty acids; fats; oils; waxes; cholesterol; sterols; fat-soluble vitamins, such as vitamins A, D, E and K; monoglycerides; diglycerides, and phospholipids. Preferred fatty acids are those selected from the group consisting of lauroic acid (C12), myristic acid (C14), palmitic acid (C16), stearic acid (C18), docosanoic acid (C22), and hybrid of lithocholic acid and oleylamine (lithocholic-oleyamine, C43). The lipid may be selected by the skilled person according to the circumstances by taking into consideration the target tissue, the target cell, the administration route, the pathway that the oligonucleotide is expected to follow, etc.

The term "monosaccharide", as used herein and is well known in the art, refers to a simple form of a sugar that consists of a single saccharide unit which cannot be further decomposed to smaller saccharide building blocks or moieties. Preferred sugar moieties for this conjugation group are selected from the group consisting of furanose, fructose, glucose, galactose, mannose, a modified monosaccharide, sialic acid and eritrose and mixtures thereof. The monosaccharides may be in its lineal or cyclic forms (hemiacetalic cyclic isomers). The furanose is any simple sugar containing a five-membered furan-based ring, such as a D-ribose or a fructose residue (D-(−)-fructofuranose). With the combination of the monosaccharides, multiple sugar structures can be attained. The fructooligosaccharides (FOS) and the galactooligosaccharides (GOS) are combinations of special interest, as well as the disaccharides sacarose or lactose; or the polysaccharides inulin, dextrin, starch or glycogen.

The terms "alkylene glycol", "poly(alkylene glycol)" an "alkylene oxide", as used herein, encompasses a family of polyether polymers which share the general formula

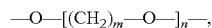

wherein m represents the number of methylene groups present in each alkylene glycol unit, and n represents the number of repeating units, and therefore represents the size or length of the polymer. The term includes. without limitation, ethylene glycol, propylene glycol, dialkylene glycol (for example, diethylene glycol), trialkylene glycol (for example, triethylene glycol), and glycols such as corresponding mono- and di-alkyl ethers of the aforementioned glycols, wherein the alkyl ethers are lower alkyl ethers having 1 to 6 carbon atoms (for example, methyl, ethyl, propyl ether and the like)

In another embodiment, the group of formula (I) has a $(C_2-C_{20})$alkylene glycol monomer unit, which may be any linear or branched molecules from 2 to 20 carbon atoms, or, depending on the values of a and b, a polyalkylene glycol polymer with several $(C_2-C_{20})$ alkylene glycol monomer units. Preferably, the alkylene glycol group is selected from $C_{16}-C_{20}$ alkylene glycol. Still more preferably, the alkylene glycol group is a $C_{18}$ alkylene glycol.

Protecting groups adequate for the conjugates of the present invention include, without limitation:

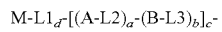

PEG+Sugar, corresponding to the above formula wherein M is H, d is 0, A is PEG, B is a sugar, a and b are each 1 and L1 and L2 are phosphodiester bonds;

PEG+(Sugar)2, corresponding to the above formula wherein A is PEG, B is a sugar, a is 1, b is 2, M is H and d is 0 and L1 and L2 are phosphodiester bonds;

(PEG)2+Sugar, corresponding to the above formula wherein A is PEG, B is a sugar, a is 2, b is 1, M is H and d is 0 and L1 and L2 are phosphodiester bonds;

(PEG)3+Sugar, corresponding to the above formula wherein A is PEG, B is a sugar, a is 3, b is 1, M is H and d is 0 and L1 and L2 are phosphodiester bonds;

(PEG)5+Sugar corresponding to the above formula wherein A is PEG, B is a sugar, a is 5, b is 1, M is H and d is 0 and L1 and L2 are phosphodiester bonds The terms "PEG" and "sugar" are used essentially as described above and include furanose as sugar and a PEG selected from the group of C3, C9 and C18 spacers.

The present invention also contemplates that the conjugate further comprises a protecting group attached to one end or to both ends of the polynucleotide which is not attached to the selectivity agent.

B. Structure of the Conjugates of the Invention

The different elements of the conjugates according to the present invention may be arranged in different manners, which form part of the present invention. Thus, the selectivity agent may be coupled to the 5' end and/or to the 3' end of the nucleic acid. Preferably, the selectivity agent is coupled to the 5' end of the nucleic acid. Moreover, the nucleic acid and the selectivity agent may be directly linked or may be connected by a linker. Similarly, the linker may be coupled to the 5' end and/or to the 3' end of the nucleic acid. Preferably, the linker is coupled to the 5' end of the nucleic acid. Thus, wherein the nucleic acid of the invention contains a single nucleic acid chain, the possible arrangements are:

- a nucleic acid comprising a selectivity agent attached to the 5' end,
- a nucleic acid comprising a selectivity agent attached to the 3' end,
- a nucleic acid comprising a selectivity agent attached to the 5' and a protecting group attached to the 3' end and
- a nucleic acid comprising a protecting group attached to the 5' end and a selectivity agent attached to the 3' end.
- a nucleic acid modified comprising a first and a second selectivity agent, being said first and second selectivity agents the same or different, being said selectivity agents connected to the 5' and 3' ends of the nucleic acid,
- a nucleic acid modified comprising a first and a second selectivity agent, being said first and second selectivity agents the same or different, both selectivity agents connected to the two ends of a bifunctional linker which is connected to the 5' end of the nucleic acid,
- a nucleic acid modified comprising a first and a second selectivity agent, being said first and second selectivity agents the same or different, both selectivity agents connected to the two ends of a bifunctional linker which is connected to the 3' end of the nucleic acid,
- a nucleic acid modified comprising four selectivity agents, being said selectivity agents the same or different, wherein two of the selectivity agents are connected to both ends of a first to bifunctional linker which is connected to the 5' of the nucleic acid end and wherein two of the selectivity agents are connected to both ends of a second bifunctional linker which is connected to the 3' of the nucleic acid.
- a nucleic acid modified comprising three selectivity agents, being said selectivity agents the same or different, wherein the three selectivity agents are connected to one end of the nucleic acid by means of a trifunctional linker.

In addition, the conjugate of the invention may contain more than one nucleic acid chain that modulates the expression of the target molecule. For example, a construction of this invention can contain up to five different nucleic acids joined in tandem through phosphodiester bonds targeted at different regions of a given target molecule.

Moreover, in those cases wherein the nucleic acid is a double stranded nucleic acid, the selectivity agent may be coupled to the sense and/or to the antisense strand and may be directly coupled or connected by a linker group. Thus, wherein the nucleic acid of the invention contains a single nucleic acid chain, the possible arrangements are:

- a nucleic acid comprising a single selectivity agent attached to the 5' end of the sense or of the antisense strand
- a nucleic acid comprising a single selectivity agent attached to the 3' end of the sense or of the antisense strand,
- a nucleic acid comprising a single selectivity agent attached to the 5' of the sense strand or of the antisense strand and a protecting group attached to the 5' end of the opposite strand,
- a nucleic acid modified comprising a first and a second selectivity agent, being said first and second selectivity agents the same or different, being said selectivity agents connected to the 5' and 3' ends of the sense or of the antisense strand of the nucleic acid,
- a nucleic acid modified comprising a first and a second selectivity agent, being said first and second selectivity agents the same or different, wherein the first selectivity agents is connected to the 5' end of the sense strand and the second selectivity agent is connected to the 5' end of the antisense strand,
- a nucleic acid modified comprising a first and a second selectivity agent, being said first and second selectivity agents the same or different, both selectivity agents connected to the 5' end of the sense strand or to the 5' end of the antisense strand by means of a bifunctional linker which is connected to the 5' end of one of the strands of the nucleic acid,
- a nucleic acid modified comprising a first and a second selectivity agent, being said first and second selectivity agents the same or different, both selectivity agents connected to the 3' end of the sense strand or to the 3' end of the antisense strand by means of a bifunctional linker which is connected to the 3' end of one of the strands of the nucleic acid,
- a nucleic acid modified comprising four selectivity agents, being said selectivity agents the same or different, wherein two of the selectivity agents are connected to the 5' end of the sense strand by means of a first bifunctional linker which is connected to the 5' of the sense strand and wherein two of the selectivity agents are connected to 5' end of the antisense strand by means of a second bifunctional linker which is connected to the 5' of the antisense strand.
- a nucleic acid modified comprising three selectivity agents, being said selectivity agents the same or different, wherein the three selectivity agents are connected to 5' end of the sense strand or to the 5' end of the antisense strand by means of a trifunctional linker.

a nucleic acid modified comprising six selectivity agents, being said selectivity agents the same or different, wherein three selectivity agents are connected to 5' end of the sense strand by means of a trifunctional linker and three selectivity agents are connected to 5' end of the antisense strand by means of a trifunctional linker, wherein both trifunctional linkers may be the same or different.

In a preferred embodiment, wherein the conjugate contains two or more selectivity agents, the different selectivity agents may be the same or different. Wherein the selectivity agents are different, they may bind the same or different receptors. Wherein the different selectivity agents bind different receptors, the receptors may be expressed either at the same cell or in different cell types. Wherein the receptors are expressed in different cell types, the receptors may be located at the same or at different locations of the central nervous system. In a preferred embodiment, the selectivity agents found within a single conjugate can bind to the following locations:
(i) mesencephalon and striatum,
(ii) cortex and hippocampus,
(iii) brainstem and hippocampus,
(iv) cortex, hippocampus and striatum,
(v) cortex, glia and hippocampus,
(vi) hippocampus and striatum,
(vii) brainstem and hypothalamus
(viii) cortex and striatum
(ix) glia and medulla
(x) brainstem, cortex and mesencephalon,
(xi) brainstem, mesencephalon and striatum,
(xii) brainstem, cortex and hippocampus and
(xiii) cortex, mesencephalon and striatum.

In a preferred embodiment, the selectivity agent of the conjugate according to the invention is a ligand of a growth hormone secretagogue receptor and the nucleic acid is specific for the SOCS3 or PTP 1B mRNAs or for the corresponding polypeptides. In a preferred embodiment, the selectivity agent is tabimorelin. In another embodiment, the nucleic acid is a single stranded nucleic and the conjugate contains two tabimorelin groups attached to the 5' end of the nucleic acid by the use of a bifunctional linker. In another embodiment, the nucleic acid is a single stranded nucleic acid and the conjugate contains two tabimorelin groups attached to the 3' end of the nucleic acid by the use of a bifunctional linker attached to the 3' end of the nucleic acid. In another embodiment, the nucleic acid is a single stranded nucleic acid and the conjugate contains two tabimorelin groups attached, respectively, to the 5' and 3' ends of the nucleic acid.

In another embodiment, the nucleic acid is a double stranded nucleic acid and the conjugate contains two tabimorelin groups attached to the 5' end of the sense strand or to the 5' end of the antisense strand by the use of a bifunctional linker. In another embodiment, the nucleic acid is a double stranded nucleic acid and the conjugate contains two tabimorelin groups, the first one attached to the 5' end of the sense strand and the second one attached to the 5' end of the antisense strand.

In another embodiment, the conjugates according to the invention contain different selectivity agents which are targeted to different receptors expressed in the same area of the central nervous system. In the case of conjugates comprising nucleic acids specific for SOCS3 or PTP-1B, the selectivity ligands may be directed to different receptors expressed in the hypothalamus, Thus, in another embodiment, the first and second selectivity agent are directed to any pairwise combination of receptors expressed in the hypothalamus selected from the group consisting of growth hormone secretagogue receptor, the galanin GAL1 receptor, the calcitonin receptor-like, the neuropeptide FF/B NPBW2 receptor, the neuropeptide FF/B NPFF2 receptor, the neuropeptide Y Y2 receptor, the bombesin BB2 receptor, the bombesin BB3 receptor, the calcitonin AM1 receptor, the calcitonin AMY1 receptor, the calcitonin CGRP receptor the calcitonin receptor, the frizzled FZD2 receptor, the frizzled FZD5 receptor, the melanocortin MC2 receptor, the melanocortin MC3 receptor, the melanocortin MC4 receptor, the neuropeptide S receptor, the neuropeptide FF/B NPFF1 receptor, the neuropeptide Y Y4 receptor, the neurotensin NTSR1 receptor, the orexin OX1 receptor, the orexin OX2 receptor, the somatostatin sst1 receptor, the somatostatin sst5 receptor, the oxytocin receptor, the vassopressin VIA receptor, the vasopressin V1B receptor, the vassopresin V2 receptor, the kisspeptin receptor, the neuropeptide FF/B NPBW1 receptor, the peptide P518 receptor, the tachykinin NK1 receptor, the tachykinin NK2 receptor and the tachykinin NK3 receptor.

The nucleic acids forming part of the conjugates of the invention have to be preserved from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Cellular exonucleases use free 5' ends as targets. Thus, in the case of single stranded nucleic acids, the selectivity agent may act as a stabilizing moiety when coupled to the 5' of the nucleic acid. However, in the case of conjugates comprising a double stranded nucleic acids or a single stranded nucleic acid in which the selectivity agent is linked to the 3' end, the conjugate may further comprise an stabilising moiety or cap structure which is usually a group which prevents degradation of the nucleic acid by the activity of exonucleases. In the case of double stranded nucleic acids, the following possible arrangements exist:

In a preferred embodiment, the nucleic acid is a double stranded RNA wherein the selectivity agent is linked to the 5' end of the antisense strand and the protecting group is linked to the 5' end of the sense strand. In a still more preferred embodiment, the protecting group has the structure

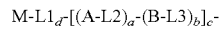

M-L1$_d$-[(A-L2)$_a$-(B-L3)$_b$]$_c$- wherein M is H, d is 0, A is a C18 spacer of polyethylene glycol, B is a furanose, a is 2, b and c are 1 and L2 and L3 are phosphodiester bonds The nucleic acids forming part of the conjugates of the invention have to be protected from degrading factors, such as nucleases (endo/exonucleases), during their transport through the different fluids and compartments of the organism. With this aim, the oligonucleotides are designed to resist the enzymatic digestion, and to improve the in vivo stability and bioavailability of the oligonucleotide. Cellular exonucleases use free 5' ends as targets. Thus, in the case of single stranded nucleic acids, the selectivity agent may act as a stabilizing moiety when coupled to the 5' of the nucleic acid. However, in the case of conjugates comprising a double stranded nucleic acids or a single stranded nucleic acid in which the selectivity agent is linked to the 3' end, the conjugate may further comprise an stabilising moiety or cap structure which is usually a group which prevents degradation of the nucleic acid by the activity of exonucleases. In the case of double stranded nucleic acids, the following possible arrangements exist:

In a still more preferred embodiment, the conjugate of the invention has the structure (I)

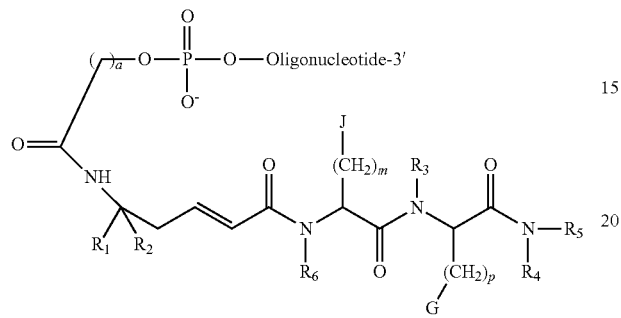

wherein $R_1$ and $R_2$ independently of each other are hydrogen or C1-C6 alkyl or R1 and $R_2$ taken together form a C2-C5 alkylene group;

J is a group

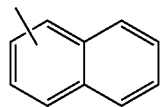

optionally substituted with one or more $C_1$-$C_6$ alkyl or halogen, m is 1, 2 or 3, $R_3$ is $C_1$-$C_6$ alkyl, p is 1, 2 or 3, a is 1 to 20

G is a group

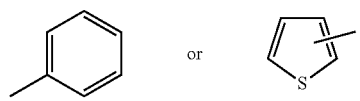

optionally substituted with one or more C1-C6 alkyl or halogen, $R_4$ and $R_5$ independently of each other are hydrogen or C1-C6 alkyl and $R_6$ is hydrogen or C1-C6 alkyl, preferably hydrogen, and wherein the oligonucleotide comprises a sequence specific for the SOCS3 mRNA or for the PTP-1B mRNA.

In another embodiment, the conjugate has the structure:

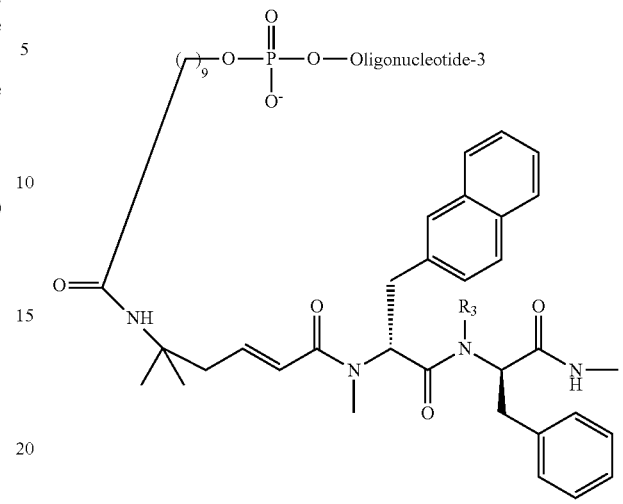

C. Pharmaceutical Compositions of the Invention

The inventors have found that the conjugates of the invention have the ability of modulating the expression of the nucleic acid which is targeted by the nucleic acid sequences of the conjugates. For instance, in the case of conjugates comprising a nucleic acid specific for the SOCS3 or PTP1B and a ligand for the growth hormone secretagogue receptor, when the construction is administered to a subject, it can effectively induce a specific knock-down of SOCS3 and PTP1B in the subjects midbrain raphe nuclei.

Thus, the skilled person will appreciate that the conjugates of the invention are adequate for the treatment of diseases which may benefit from the reduction in the expression levels of the genes which are targeted by the nucleic acids present in the conjugates of the invention. Thus, in another aspect, the invention relates to a conjugate according to the invention for use in medicine. Additionally, the invention also relates to a pharmaceutical composition comprising a conjugate according to the invention and a pharmaceutically-acceptable excipient.

Appropriate amounts of oligonucleotide constructions of the invention can be formulated with pharmaceutically acceptable excipients and/or carriers to obtain a pharmaceutical composition. A composition that includes a conjugate according to the invention can be delivered to a subject by a variety of routes. Exemplary routes include intrastriatal, intracerebroventricular, intrathecal, intraparenchymal (e.g., in the striatum), intranasal, and ocular delivery. The composition can also be delivered systemically, e.g., by intravenous, subcutaneous or intramuscular injection, which is particularly useful for delivery of the conjugates to peripheral neurons. Additionally, it is also possible to administer the conjugates of the invention intranasally which allows systemic administration by a non-aggressive mode of administration. Also, intraventricular administration may also be adequate. A preferred route of delivery is directly to the brain, e.g., into the ventricles or the hypothalamus of the brain, or into the lateral or dorsal areas of the brain.

Those of skill in the art are familiar with the principles and procedures discussed in widely known and available sources as Remington's Pharmaceutical Science (17th Ed., Mack Publishing Co., Easton, Pa., 1985) and Goodman and Gilman's The Pharmaceutical Basis of Therapeutics (8th Ed., Pergamon Press, Elmsford, N.Y., 1990) both of which are incorporated herein by reference.

In a preferred embodiment of the present invention, the conjugates are formulated in accordance with standard procedure as a pharmaceutical composition adapted for delivered administration to human beings and other mammals. Typically, compositions for intravenous or intraventricular administration are solutions in sterile isotonic aqueous buffer.

Where necessary, the composition may also include a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

In yet another preferred embodiment, therapeutics containing the conjugates of the invention can be formulated as neutral or salt forms. Pharmaceutically acceptable salts include those formed with free amino groups such as those derived from hydrochloric, phosphoric, acetic, oxalic, tartaric acids and the like, and those formed with free carboxyl groups such as those derived from sodium, potassium, ammonium, calcium, ferric hydroxides, isopropylamine, thriethylamine, 2-ethylamino ethanol, histidine, procaine or similar.

D. Therapeutic Uses of the Conjugates of the Invention

It will be appreciated that the clinical condition that can be treated with the conjugates of the invention will depend on the specificity of the nucleic acid which forms part of the conjugates. Thus, the conjugates of the invention can be used for the treatment of any disease which can be improved by knocking down a gene of interest in a cell that expresses a neurotransmitter transporter. The skilled person will understand that the conjugates are useful for the treatment of diseases characterized by abnormal expression of a protein in a cell or for diseases wherein the target protein is expressed at normal levels but which can be improved by decreasing the expression of said target protein. Thus, in another embodiment, the invention relates to a method for the treatment of a diseases in a subject in need thereof comprising administering to said subject a conjugate according to the invention wherein the conjugate contains a nucleic acid which is capable of silencing the expression of a target gene involved in said disease and a ligand which is specific for a receptor which is expressed in the cells wherein said target gene is expressed.

In one embodiment, wherein the selectivity agent is specific for a receptor expressed in the hypothalamus, the invention relates to the use of a conjugate for the treatment of the diseases shown in Table 3 (right-hand column) wherein the nucleic acid is specific for the target polypeptide shown in Table 3 (left hand-column).

TABLE 3

Target polypeptides expressed in the hypothalamus and diseases which can be treated by silencing said polypeptides

| Target polypeptide | Disease |
| --- | --- |
| Suppressor of cytokine signaling 3 (SOCS3), protein-tyrosine phosphatase 1B (PTP1B), CB1, interleukin beta 1 (IL1B), neuropeptide Y (NPY), ghrelin receptor, Y1, Y5 | Eating disorders, obesity |

In one embodiment, wherein the selectivity agent is specific for a receptor expressed in the mesencephalon, the invention relates to the use of a conjugate for the treatment of the diseases shown in Table 4 (right-hand column) wherein the nucleic acid is specific for the target polypeptide shown in Table 4 (left hand-column).

TABLE 4

Target polypeptides expressed in the mesencephalon and diseases which can be treated by silencing said polypeptides

| Target polypeptide | Disease |
| --- | --- |
| D1, D2, D3, DAT | Addiction |
| alpha-synuclein | Synucleinopathies |
| D1, D2, D3, DAT | Schizophrenia |
| D2, DAT | Post-traumatic stress disorder |

In one embodiment, wherein the selectivity agent is specific for a receptor expressed in the brainstem, the invention relates to the use of a conjugate for the treatment of the diseases shown in Table 5 (right-hand column) wherein the nucleic acid is specific for the target polypeptide shown in Table 5 (left hand-column).

TABLE 5

Target polypeptides expressed in the brainstem and diseases which can be treated by silencing said polypeptides.

| Target polypeptide | Disease |
| --- | --- |
| 5-HT1A, 5-HT2C, SERT | Anxiety |
| alpha1A-adrenoceptor, angiotensin converting enzyme, G protein β3, 5-HT2C, interleukin 1β, monoamine oxidase A, SERT | Depression |
| CB1 | Eating disorders. |
| 5-HT1A | Migraine |
| alpha-synuclein | Synucleinopathies |
| SERT | Phobias, post-traumatic stress disorder. |
| 5-HT1A, 5-HT1A2C | Psychotic disorders |
| 5-HT1A | Sleep disorders |

In one embodiment, wherein the selectivity agent is specific for a receptor expressed in the cortex, the invention relates to the use of a conjugate for the treatment of the diseases shown in Table 6 (right-hand column) wherein the nucleic acid is specific for the target polypeptide shown in Table 6 (left hand-column).

TABLE 6

Target polypeptides expressed in the cortex and diseases which can be treated by silencing said polypeptides

| Target polypeptide | Disease |
|---|---|
| gene product encoded in chromosome 21 | Alzheimer's disease associated with Down syndrome |
| amyloid precursor protein, presenilin 1, presenilin 2 | Early onset Alzheimer's disease |
| Apolipoprotein E, cyclin-dependent kinase 5, glycogen synthase kinase 3, the microtubule affinity-regulating kinase | Late onset, early onset or sporadic Alzheimer's disease. |
| A2, D4 | Attention deficit hyperactivity disorder. |
| acetylcholinesterase, A2, CB1, catechol-O-methyl transferase, histamine N-methyltransferase, H3, 5-HT6, phosphodiesterase 10A, phosphodiesterase 1B, phosphodiesterase 1C, phosphodiesterase 2A, phosphodiesterase 4A, phosphodiesterase 4B, phosphodiesterase 4D, phosphodiesterase 7A, phosphodiesterase 7B, phosphodiesterase 8B, phosphodiesterase 9B | Cognitive impairment. |
| D1, D2, D3 | Disinhibition |
| uncharacterized protein C9orf72, progranulin, Tau | Frontotemporal dementia. |
| Huntingtin | Huntington's disease |
| alpha-synuclein | Synucleinopathies |
| D1, D2, D3 | Parkinson's Disease |
| D1, D2, D3, kynuerine aminotransferase | Schizophrenia |
| 5-HT2C, kynuerine aminotransferase, miR-137 | Psychotic disorders |

In one embodiment, wherein the selectivity agent is specific for a receptor expressed in the cerebellum, the invention relates to the use of a conjugate for the treatment of the diseases shown in Table 7 (right-hand column) wherein the nucleic acid is specific for the target polypeptide shown in Table 7 (left hand-column).

TABLE 7

Target polypeptides expressed in the cerebellum and diseases which can be treated by silencing said polypeptides

| Target polypeptide | Disease |
|---|---|
| Atrophin-1 | Dentatorubral Atrophy |
| Fragile X Mental retardation 1 | Fragile X-associated Tremor/Ataxia Syndrome (FXTAS) |
| G-protein coupled receptor 55 | Movement disorders. |
| 1p36 | Spinocerebellar Ataxia Autosomal Recesive Type 4, SCAR4 (Old SCA24) or Spinocerebellar Ataxia with Saccadic Intrusions |
| ataxin 1 | Spinocerebellar Ataxia Type 1 |
| ataxin 10 | Spinocerebellar Ataxia Type 10 |
| tubulin kinase 2 | Spinocerebellar Ataxia Type 11 |
| PPP2R2B | Spinocerebellar Ataxia Type 12 |
| Kv3.3 channel | Spinocerebellar Ataxia Type 13 |
| Protein kinase C gamma | Spinocerebellar Ataxia Type 14 |
| inositol receptor | Spinocerebellar Ataxia Type 15/16 |
| Ataxin 17 | Spinocerebellar Ataxia Type 17 |
| interferon-related developmental regulator gene 1 | Spinocerebellar Ataxia Type 18 |
| Ataxin 19 | Spinocerebellar Ataxia Type 19 |
| Ataxin 2 | Spinocerebellar Ataxia Type 2 |
| Ataxin 20 | Spinocerebellar Ataxia Type 20 |
| Ataxin 21 | Spinocerebellar Ataxia Type 21 |
| Ataxin 22 | Spinocerebellar Ataxia Type 22 |
| dynorphin | Spinocerebellar Ataxia Type 23 |
| Ataxin 25 | Spinocerebellar Ataxia Type 25 |
| Ataxin 26 | Spinocerebellar Ataxia Type 26 |
| Fibroblast growth factor14 | Spinocerebellar ataxia type 27 |
| mitochondrial metalloprotease complex | Spinocerebellar Ataxia Type 28 |
| ataxin 29 | Spinocerebellar Ataxia Type 29 |
| ataxin 3 | Spinocerebellar Ataxia Type 3 |
| ataxin 30 | Spinocerebellar Ataxia Type 30 |
| Thymidine kinase 2 & Brain expressed associated with NEDD4 | Spinocerebellar Ataxia Type 31 |
| ataxin 32 | Spinocerebellar Ataxia Type 32 |
| ataxin 33 | Spinocerebellar Ataxia Type 33 |
| gene product encoded by 16p12.3-q16.2 | Spinocerebellar Ataxia Type 34 |
| transglutaminase | Spinocerebellar Ataxia Type 35 |
| Nuclear Protein 56 | Spinocerebellar Ataxia Type 36. |
| Ataxin 4 | Spinocerebellar Ataxia Type 4 |
| Ataxin 5 | Spinocerebellar Ataxia Type 5 |
| alpha1A subunit of P/Q calcium channel | Spinocerebellar Ataxia Type 6 |
| Ataxin 7 | Spinocerebellar Ataxia Type 7 |
| Kelch-like protein 1 | Spinocerebellar Ataxia Type 8 |

In one embodiment, wherein the selectivity agent is specific for a receptor expressed in the striatum, the invention relates to the use of a conjugate for the treatment of the diseases shown in Table 8 (right-hand column) wherein the nucleic acid is specific for the target polypeptide shown in Table 8 (left hand-column).

TABLE 8

Target polypeptides expressed in the striatum and diseases which can be treated by silencing said polypeptides

| Target polypeptide | Disease |
|---|---|
| D1, D2, D3, 5-HT2C | Addiction |
| A2A | Attention Deficit Hyperactivity Disorder (ADHD) |
| A2A | Cognitive impairment |
| D2 | Disinhibition |
| Huntingtin | Huntington's disease |
| D2, DAT | Post-tratumatic stress disorder |
| D1, D2, D3 | Schizophrenia |

In one embodiment, wherein the selectivity agent is specific for a receptor expressed in the hippocampus, the invention relates to the use of a conjugate for the treatment of the diseases shown in Table 9 (right-hand column) wherein the nucleic acid is specific for the target polypeptide shown in Table 9 (left hand-column).

TABLE 9

Target polypeptides expressed in the hippocampus and diseases which can be treated by silencing said polypeptides.

| Target polypeptide | Disease |
|---|---|
| gene product encoded in chromosome 21 | Alzheimer's disease associated with Down syndrome |
| amyloid precursor protein, presenilin 1, presenilin 2 | Early onset Alzheimer's disease |
| Apolipoprotein E, cyclin- | Late onset, early onset or sporadic |

TABLE 9-continued

Target polypeptides expressed in the hippocampus and diseases which can be treated by silencing said polypeptides.

| Target polypeptide | Disease |
|---|---|
| dependent kinase 5, glycogen synthase kinase 3, the microtubule affinity-regulating kinase | Alzheimer's disease |
| 5-HT1A | Anxiety |
| A1 | Attention Deficit Hyperactivity Disorder (ADHD) |
| 5-HT1A | Bipolar disorder |
| acetylcholinesterase, A1, CB1, catechol-O-methyl transferase, histamine N-methyltransferase, H3, 5-HT6, nitric oxide synthase, phosphodiesterase 10A, phosphodiesterase 1B, phosphodiesterase 1C, phosphodiesterase 2A, phosphodiesterase 4A, phosphodiesterase 4B, phosphodiesterase 4D, phosphodiesterase 7A, phosphodiesterase 7B, phosphodiesterase 8B, phosphodiesterase 9A | Cognitive impairment |
| 5-HT1A | Migraine, psychotic disorders or sleep disorders |

In one embodiment, wherein the selectivity agent is specific for a receptor expressed in the spinal cord, the invention relates to the use of a conjugate for the treatment of the diseases shown in Table 10 (right-hand column) wherein the nucleic acid is specific for the target polypeptide shown in Table 10 (left hand-column)

TABLE 10

Target polypeptides expressed in the spinal cord and diseases which can be treated by silencing said polypeptides

| Target polypeptide | Disease |
|---|---|
| Superoxide dismutase 1, Alsin, Probable helicase senataxin, RNA-binding protein FUS, Vesicle-associated membrane protein-associated protein B/C, Angiogenin, TAR DNA-binding protein 43, Polyphosphoinositide phosphatase, Optineurin, Ataxin-2, valosin-containing protein | Amyotrophic lateral sclerosis (ALS)/Lou Gehrig's disease |
| reticulon 4 | Ataxia, Brown-Séquard sindrome and Neuropathy, Pain, Paralysis, Sipanl Cord injury |
| Nav1.7, Nav1.8, Cav2.2, COX-2, kappa | Neuropathy, Pain |
| Survival motor neuron protein | Spinal cord injury, spinal cord atrophy (SMA) |

The amount of the conjugate of the present invention which will be effective in the treatment of a particular disorder or condition will depend on the nature of the disorder or condition, and can be determined by standard clinical techniques, well established in the administration of therapeutics. The precise dose to be employed in the formulation will also depend on the route of administration, and the seriousness of the disease or disorder, and should be decided according to the judgment of the practitioner and the patient's needs. Suitable dose ranges for intracranial administration are generally about 10 3 to 10 15 infectious units of viral vector per microliter delivered in 1 to 3000 microliters of single injection volume. Addition amounts of infections units of vector per micro liter would generally contain about 10 4, 10 5, 10 6, 10 7, 10 8, 10 9, 10 10, 10 11, 10 12, 10 13, 10 14 infectious units of viral vector delivered in about 10, 50, 100, 200, 500, 1000, or 2000 microliters. Effective doses may be extrapolated from dose-responsive curves derived from in vitro or in vivo test systems.

For the intraventricular administration of the conjugates of the invention, multiple catheters having access ports can be implanted in a given patient for a complete therapy. In a preferred embodiment, there is one port and catheter system per cerebral or cerebellar hemisphere, and perhaps several. Once the implantations are performed by a neurosurgeon, the patient's neurologist can perform a course of therapy consisting of repeated bolus injections of the conjugates over a period of weeks to months, along with monitoring for therapeutic effect over time. The devices can remain implanted for several months or years for a full course of therapy. After confirmation of therapeutic efficacy, the access ports might optionally be explanted, and the catheters can be sealed and abandoned, or explanted as well. The device material should not interfere with magnetic resonance imaging, and, of course, the small interfering RNA preparations must be compatible with the access port and catheter materials and any surface coatings.

E. Synthesis of the Conjugates of the Invention

The conjugates of the invention are typically synthesized using standard procedures in organic synthesis. The skilled person will appreciate that the exact steps of the synthesis will depend on the exact structure of the conjugate which has to be synthesized. For instance, if the conjugate comprises a single nucleic acid strand conjugated to the selectivity agent through its 5' end, then the synthesis is usually carried out as explained below by contacting an activated oligonucleotide and a reactive activated selectivity reagent.

Wherein the conjugate comprises a double stranded nucleic acid, then the sense and antisense strands are synthesized separately and annealed in vitro using standard molecular biology procedures. In a typical conjugate, the first the nucleic acid strands carries the selectivity agent and the second nucleic acid strands carries a protecting group. In a still more preferred embodiment, the selectivity agent is coupled to the 5' end of the first nucleic acid strand and/or the protecting group is attached to the 5' end of the second nucleic acid strand, although the attachment of the selectivity agent or of the protecting group can also be carried out at the 3' ends of the nucleic acid strands.

Synthesis of the conjugates can be carried out as follows:

[1] Conjugates having the structure

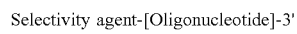

Selectivity agent-[Oligonucleotide]-3' are typically synthesized using the following steps:
(i) Activating the selectivity agent. Preferably, the activation group in the selectivity agent is a succinimide group. Wherein the selectivity agent carried a primary or secondary amino group, this step may not be necessary since this group may react directly with the activated oligonucleotide.
(ii) Activating the oligonucleotide on its 5' end. Preferably, the activation group in the oligonucleotide is amino group or a caboxy group and
(iii) contacting the activated selectivity agent with the activated oligonucleotide under conditions adequate for the reaction between the two activation groups.

[2] Conjugates having the structure

---
Protecting group - [Sense strand]-3'
3' - [Antisense strand] - Selectivity agent
--- are typically synthesized using the following steps:
(i) Activating the selectivity agent. Preferably, the activation group in the selectivity agent is a succinimide. Wherein the selectivity agent carried a primary or secondary amino group, this step may not be necessary since this group may react directly with the activated oligonucleotide.
(ii) Activating the sense strand on its 5' end. Preferably, the activation group in the oligonucleotide is amino group,
(iii) contacting the activated selectivity agent with the activated sense strand under conditions adequate for the reaction between the two activation groups,
(iv) Adding the protecting group to the immobilised antisense strand. This step is preferably carried out using an oligonucleotide which reactive groups are blocked by acetylation or benzylation (the furanose groups), 2-cyanoethylation (the phosphodiester linkages) and FMOC (the exocyclic amino groups).
(v) Annealing the sense and antisense strands E.1. Synthesis of Conjugates Comprising a Nucleic Acid and a Ligand for a Growth-Hormone Secretagogue Ligand Attached to the 5' End.

The conjugates of the invention can be prepared using techniques known by those skilled in the art. The synthesis of conjugates may involve the selective protection and deprotection of functional groups. Suitable protecting groups are well known for the skilled person in the art. For example, a general review of protecting groups in organic chemistry is provided by Wuts, P. G. M. and Greene T. W. in *Protecting Groups in Organic Synthesis* (4$^{th}$ Ed. Wiley-Interscience), and by Kocienski P. J. in *Protecting Groups* (3$^{rd}$ Ed. Georg Thieme Verlag).

In the context of the present invention, the following terms have the meaning detailed below:

The term "$C_1$-$C_6$ alkyl" relates to a linear or branched hydrocarbon radical consisting of carbon and hydrogen atoms, which does not contain unsaturation, having one to six, preferably one to three ($C_1$-$C_3$ alkyl), carbon atoms and which is joined to the rest of the molecule by a single bond. Examples of alkyl groups include but are not limited to alkyl groups such as methyl, ethyl, propyl, isopropyl, butyl, isobutyl, t-butyl, pentyl and hexyl. Preferably alkyl refers to methyl.

The term "halogen" refers to bromo, chloro, iodo or fluoro.

The term "haloalkyl" refers to an alkyl group as defined above wherein at least one hydrogen atom has been replaced by halogen. Examples of haloalkyl groups include but are not limited to $CF_3$, $CCl_3$, $CHF_2$, $CF_2CF_3$. Preferably haloalkyl refers to $CF_3$.

The term "$C_6$-$C_{10}$ aryl" refers to an aromatic group having between 6 and 10 carbon atoms, comprising 1 or 2 aromatic nuclei, bound by means of a carbon-carbon bond or fused, including for example phenyl, naphthyl and diphenyl. Preferably "aryl" refers to phenyl.

The compounds of the present invention represented by the above described formula (I) may include stereoisomers depending on the presence of chiral centres. The single isomers, enantiomers or diastereoisomers and mixtures thereof fall within the scope of the present invention.

Unless otherwise indicated, the compounds used in the invention are intended to include compounds that only differ in the presence of one or more isotopically enriched atoms. For example, compounds having the present structures except for the substitution of a hydrogen with deuterium or tritium, or the substitution of a carbon with a $^{13}$C- or $^{14}$C-enriched carbon or a $^{15}$N-enriched nitrogen are within the scope of this invention.

Synthesis Using an Carboxy-Derivatized Nucleic Acid and an Activated Triple Uptake Inhibitor In an embodiment, the conjugate of the invention is obtained by the conjugation of an amino-derivatized selectivity agent and a carboxyl-derivatized oligonucleotide. In particular, the conjugate of the invention has the structure (I):

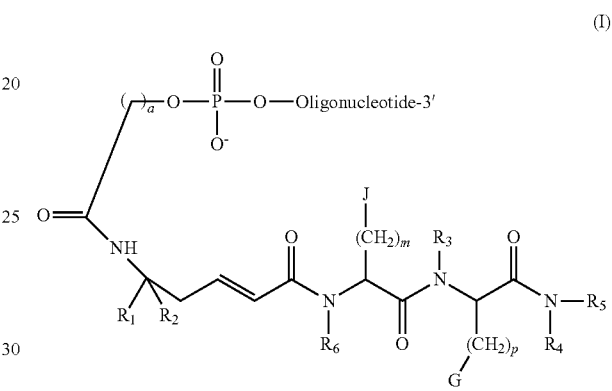

wherein $R_1$ and $R_2$ independently of each other are hydrogen or C1-C6 alkyl or R1 and $R_2$ taken together form a C2-C5 alkylene group;
J is a group

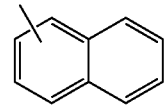

optionally substituted with one or more C1-C6 alkyl or halogen,
m is 1, 2 or 3,
$R_3$ is C1-C6 alkyl,
p is 1, 2 or 3,
a is 1 to 20
G is a group

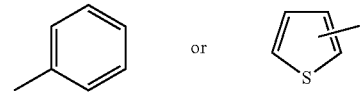

optionally substituted with one or more C1-C6 alkyl or halogen,
$R_4$ and $R_5$ independently of each other are hydrogen or C1-C6 alkyl and
$R_6$ is hydrogen or C1-C6 alkyl, preferably hydrogen
and wherein the oligonucleotide is a nucleic acid which is capable of specifically binding to a target molecule wherein said target molecule is the mRNA of a polypeptide as defined in Table 3 (left-hand column).

The process of synthesis of a conjugate having the structure of (III) comprises reacting a compound having the structure of (V):

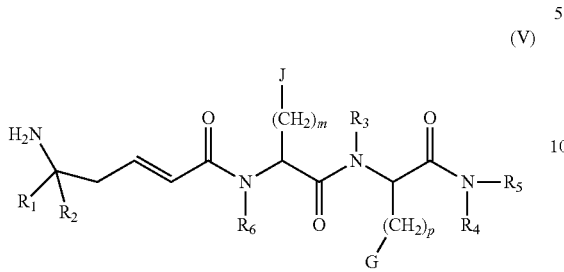

with a carboxymodified oligonucleotide having the formula (VI):

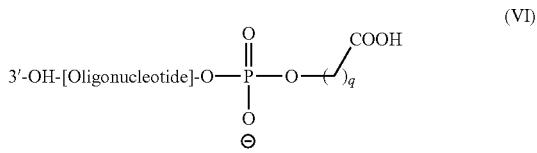

Thus, the invention is also related to a compound having the structure (VI) wherein the oligonucleotide is a nucleic acid which is capable of specifically binding to a target molecule wherein said target molecule is the mRNA of a polypeptide as defined in Table 3 (left-hand column). In a particular embodiment, the oligonucleotide in the compound having the structure (VI) is an antisense gapmer. In particular, said gapmer comprises a central block of 10 deoxynucleotides flanked by blocks of 5 2'-Omethyl modified ribonucleotides. In another embodiment, the nucleic acid is the sense or antisense strand of a siRNA.

The general procedure for activating an oligonucleotide using a carboxyl linker a modifier will typically be according to the scheme below:

enable the linker/modifier molecule from Y reservoir to couple at the end of the oligonucleotide sequence.

(iii) start the synthesis using the appropriate coupling cycle. The same coupling cycle will be used to carry out the linker/modifier molecule coupling.

(iv) at the end of the oligonucleotide synthesis, wash the support and finally dry the support with gas (v) remove the solid support from the column and transfer it into a screw capped vial and complete the 2 step de-protection.

The carboxymodified oligonucleotide should be deprotected for further conjugation with the selectivity agent. For this purpose all the remaining protecting groups in the oligonucleotide are removed as follows. 500 μl of a mixture containing 20% v/v of methylamine (aqueous solution 40% w/v) and 80% v/v of a saturated ammonia solution, (containing 30-32% w/v of $NH_3$) were added to an Eppendorf tube with the oligonucleotide (200 nmole scale). The tube was hermetically closed and heated for 45 minutes to a temperature of 65° C. This procedure eliminates the protecting groups in the phosphorous atom of the nucleotides (acetylation or benzoylation of the furanose and the 2-cyanoethylation of the phosphodiester linkages), and the protecting groups of the exocyclic amino groups (Bz, Ac, IBu). The mixture was then cooled and filtered and the supernatant was dried. The residual pellet was reacted with 1M triethylamine-HF for 3 hours at 65° C. to cleave the protecting groups at 2' of the nucleotides (2'-t-butyl dimethyl silyl-TBDMS). Finally, the resultant solution was desalted in a Sephadex column, leaving a carboxymodified-5'-oligonucleotide.

In a particular embodiment, the oligonucleotide comprised by the conjugate synthesized by the method of the invention is an antisense gapmer. In particular, the gapmer comprises a central block of 10 deoxynucleotides flanked by blocks of 5 2'-Omethyl modified ribonucleotides.

The carboxyl-activated oligonucleotide is then reacted with the activated derivative of a selectivity agent of formula (V) as defined above. A compound is obtained having the general formula (I) as shown above.

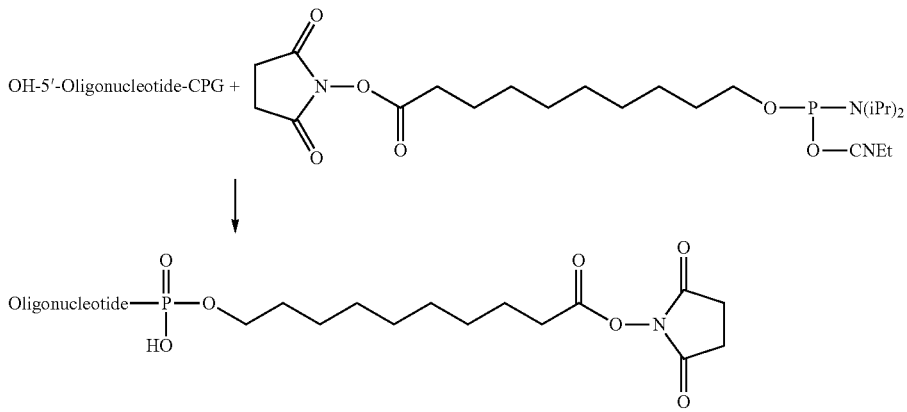

General Method of Synthesis of the Carboxymodified Oligonucleotide:

(i) prepare a solution of modifier molecule in anhydrous acetonitrile and place it into an extra reservoir in your synthesizer (Y)

(ii) at the start of the synthesis of the required oligonucleotide sequence, add the Y base at the 5' end. This will In particular, this compound (I) comprises an oligonucleotide which is capable of specifically binding to a target molecule wherein said target molecule is a polypeptide as defined in Table 3 or the mRNA encoding said polypeptide. In a particular embodiment, the oligonucleotide in the compound having the structure (III) is an antisense gapmer. In particular, said gapmer comprises a central block of 10 deoxynucleotides flanked by blocks of 5 2'-Omethyl modified ribonucleotides. In another embodiment, the nucleic acid is the sense or antisense strand of a siRNA.

F. Diagnostic Conjugates and Uses Thereof

The possibility of achieving delivery of therapeutic compounds in a target-cell specific manner by using selectivity agents capable of binding with high affinity to neurotransmitter transporters can also be applied for the delivery of compounds that can be used for diagnostic purposes. Thus, in another embodiment, the invention provides a conjugate comprising a
(i) at least one selectivity agent which binds specifically to a receptor which can be internalized by the cell upon binding of said selectivity agent and
(ii) an imaging agent.

The term "selectivity agent" and "receptor" have been described in detail above and can be understood equally for the diagnostic conjugates of the invention. Any of the selectivity agents mentioned above can be used in the conjugates for imaging according to the invention.

The terms "imaging agent" and "contrast agent", are used herein interchangeably and refer to a biocompatible compound, the use of which facilitates the differentiation of different parts of the image, by increasing the "contrast" between those different regions of the image. The term "contrast agents" thus encompasses agents that are used to enhance the quality of an image that may nonetheless be generated in the absence of such an agent (as is the case, for instance, in MRI), as well as agents that are prerequisites for the generation of an image (as is the case, for instance, in nuclear imaging). Suitable contrast agent include, without limitation, contrast agents for Radionuclide imaging, for computerized tomography, for Raman spectroscopy, for Magnetic resonance imaging (MRI) and for optical imaging.

Contrast agents for radionuclide imaging include radiopharmaceuticals are commonly labeled with positron-emitters such as $^{11}C$, $^{13}N$, $^{15}O$, $^{18}F$, $^{82}Rb$, $^{62}Cu$ and $^{68}Ga$. SPECT radiopharmaceuticals are commonly labeled with positron emitters such as $^{94m}Tc$, $^{201}Tl$ and $^{67}Ga$. Radionuclide imaging modalities (positron emission tomography, (PET); single photon emission computed tomography (SPECT)) are diagnostic cross-sectional imaging techniques that map the location and concentration of radionuclide-labeled radiotracers. PET and SPECT can be used to localize and characterize a radionuclide by measuring metabolic activity. PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high. In certain embodiments of the invention, a cell is labeled ex vivo for PET or SPECT imaging in vivo. Closely related to PET is single-photon emission computed tomography, or SPECT. The major difference between the two is that instead of a positron-emitting substance, SPECT uses a radioactive tracer that emits low-energy photons.

Contrast agents for CT imaging include, for example, iodinated or brominated contrast media. Examples of these agents include iothalamate, iohexyl, diatrizoate, iopamidol, ethiodol and iopanoate. Gadolinium agents have also been reported to be of use as a CT contrast agent (see, e.g., Henson et al., 2004). For example, gadopentate agents has been used as a CT contrast agent (discussed in Strunk and Schild, 2004). Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth. In CT, intravenous injection of a radiopaque contrast agent such as those described herein can assist in the identification and delineation of soft tissue masses when initial CT scans are not diagnostic.

Contrast agents for optical imaging include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye and the various other fluorescent compounds disclosed herein.

In a preferred embodiment, the contrast agent is a compound that is able to be imaged by a magnetic resonance imaging apparatus. Contrast agents which can be imaged by a magnetic resonance imaging apparatus differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles. In one particular embodiment, the MRI contrast agent is $^{19}F$. Both CT and MRI provide anatomical information that aid in distinguishing tissue boundaries. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability. Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

MRI contrast agents include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III). In a preferred embodiment, the compound that is able to be imaged by a magnetic resonance imaging apparatus is a gadolinium-based compound.

The term "gadolinium-based compound", as used herein, shall mean, where used with respect to brain imaging, any gadolinium-containing substance administrable to a subject which results in an intravascular enhancement. In another embodiment, the gadolinium-containing contrast agent is selected from the group consisting of gadolinium, gadolinium pentate, and gadodiamide.

The amount of the gadolinium-containing contrast agent to be administered varies in an amount of about 10 mg per kg body weight. In another embodiment, the second magnetic resonance image is acquired about 45 minutes after administering the gadolinium-containing contrast agent. This invention also provides the above-described method further comprising the step of intraperitoneally administering a saline solution (e.g. Ringer's solution) to the subject, which administering follows either step (c) or step (d).

The invention also provides the use of a conjugate as defined above as diagnostic agent and methods for the detection of cells expressing the neurotransmitter transporter on their surface.

The invention also provides multimodal imaging methods. Certain embodiments of the present invention pertain to methods of imaging a subject, or a site within a subject using multiple imaging modalities that involve measuring multiple signals. In certain embodiments, the multiple signals result from a single label on, or in a cell. As set forth above, any imaging modality known to those of ordinary skill in the art can be applied in these embodiments of the present imaging methods.

The imaging modalities are performed at any time during or after administration of the labeled composition, e.g., labeled cell. For example, the imaging studies may be performed during administration of the labeled cell of the present invention, i.e., to aid in guiding the delivery to a specific location, or at any time thereafter.

Additional imaging modalities may be performed concurrently with the first imaging modality, or at any time following the first imaging modality. For example, additional imaging modalities may be performed about 1 sec, about 1 hour, about 1 day, or any longer period of time following completion of the first imaging modality, or at any time in between any of these stated times. In certain embodiments of the present invention, multiple imaging modalities are performed concurrently such that they begin at the same time following administration of the labeled cell or agent. One of ordinary skill in the art would be familiar with performance of the various imaging modalities contemplated by the present invention.

In some embodiments of the present methods of imaging, the same imaging device is used to perform a first imaging modality and a second imaging modality. In other embodiments, different imaging devices are used to perform the different imaging modalities. One of ordinary skill in the art would be familiar with the imaging devices that are available for performance of the imaging modalities described herein.

The instant invention provides methods for imaging cells using one or more imaging modalities. In some embodiments the cells are labeled with multiple imaging agents, and in other aspects the cells are labeled with a single labeling agent. In certain embodiments, the single labeling agent is a multimode-detectable agent.

G. Conjugates Comprising Liposomes and Dendrimers

In another embodiment, the invention provides conjugates comprising a liposome and a selectivity agent which binds specifically to a receptor which can be internalized by the cell upon binding of said selectivity agent.

In another embodiment, the invention provides conjugates comprising a dendrimer and a selectivity agent which binds specifically to a receptor which can be internalized by the cell upon binding of said selectivity agent.

By encapsulating a therapeutical compound within the dendrimer or liposome, the conjugates allows the selective delivery of said compound to cells which express said neurotransmitter transporter.

In a preferred embodiment, the selectivity agent is specific for a receptor as defined in Table 1 (left-hand column). In another embodiment, the selectivity agent is specific for a receptor as defined in Table 1 (right-hand column). In another embodiment, the selectivity agent is any agent as defined in Table 2. In a more preferred embodiment, the selectivity agent is growth-hormone secretagogue receptor. In a still more preferred embodiment, the selectivity agent has the structure

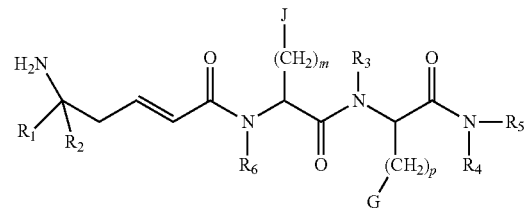

wherein m, p, $R_1$, $R_2$, $R_3$, $R_4$, $R_5$ and $R_6$ are as defined above.

Liposomes and nanoparticles are exemplary forms of nanocontainers that are commonly used for encapsulation of drugs. The liposomes preferably have diameters of less than 200 nanometers. Liposomes having diameters of between 50 and 150 nanometers are preferred. Especially preferred are liposomes or other nanocontainers having external diameters of about 80 nanometers. Suitable types of liposomes are made with neutral phospholipids such as 1-palmitoyl-2-oleoyl-sn-glycerol-3-phosphocholine (POPC), diphosphatidyl phosphocholine, distearoylphosphatidylethanolamine (DSPE), or cholesterol, along with a small amount (1 percent) of cationic lipid, such as didodecyldimethylammonium bromide (DDAB) to stabilize the DNA within the liposome.

The liposome can be replaced with a nanoparticle or any other molecular nanocontainer with a diameter less than 200 nm that can encapsulate the DNA and protect the nucleic acid from nucleases while the formulation is still in the blood or in transit from the blood to the intracellular compartment of the target cell. Also, instead of using conjugation agents such as PEG strands, one or more other polymeric substances, such as sphingomylein, can be attached to the surface of the liposome or nanocontainer and serve the dual purpose of providing a scaffold for conjugation of the "transportable peptide" and for delaying the removal of the formulation from blood and optimizing the plasma pharmacokinetics. Further, the present invention contemplates delivery of DNA to any group of cells or organs which have specific target receptors. The liposomes may be used to deliver DNA to organs, such as liver, lung and spleen.

Other suitable containers for the delivery of the conjugates of the invention include dendrimers. The term "dendrimer" refers to a macromolecule having a core and having multiple shells of branching structures emanating from the core. The shape and size of a dendritic carrier can vary. In some instances, the dendritic carrier can be approximately spherical or globular in shape. Furthermore, the dendritic carrier can have a diameter in the range of about 15 angstroms (A) to about 250 A, with a corresponding range of molecular weights, e.g., from about 500 Daltons to about 2 million Daltons. Dendrimers can be obtained commercially from various sources (e.g., Dendritech, Midland, Mich.) or synthesized by methods known to those skilled in the art. Dendritic molecules can roughly be divided into the low-molecular weight and the high-molecular weight species. The first category includes dendrimers and dendrons whereas the second encompasses dendronized polymers, hyperbranched polymers, and brush-polymers (also called bottle-brushes). Dendrimers and dendrons are repeatedly branched, monodisperse, and usually highly symmetric compounds. There is no apparent difference in defining dendrimer and dendron. A dendron usually contains a single chemically addressable group that is called the focal point. Because of the lack of the molar mass distribution high-molar-mass dendrimers and dendrons are macromolecules but not polymers. The properties of dendrimers are dominated by the functional groups on the molecular surface. Dendritic encapsulation of functional molecules allows for the isolation of the active site, a structure that mimics the structure of active sites in biomaterials because dendritic scaffolds separate internal and external functions. For example, a dendrimer can be water-soluble when its end-group is a hydrophilic group, like a carboxyl group.

Dendrimers may be generally characterised by the following features: (i) an initiator core (I) which may have one or more reactive sites and be point-like or of significant size so as to effect the final topology of the dendrimer; (ii) one or more layers of branched repeating units attached to the initiator core; (iii) functional terminal groups, such as anionic or cationic groups, attached, optionally through linking groups, to the surface of the dendrimer.

Dendrimers contemplated herein may comprise lysine, or lysine analogue building units. The term "lysine analogue" refers to a molecule which has a single apex carboxyl group for attachment to the previous layer of building units, and two or three primary amine groups to which can be attached further building units, blocking groups, linkers or aryl acid groups. Examples of "lysine analogues" contemplated herein are described in PCT/AU2007/000352, for example glycyl-lys. In some particular examples, the dendrimer comprises only lysine or one type of lysine analogue as the building unit.

Other dendrimers contemplated herein include those comprising polyamidoamine (PAMAM), poly(etherhydroxylamine) (PEHAM) or polypropyleneimine building units. In particular examples thereof, the dendrimer has only polyamidoamine (PAMAM), poly(etherhydroxylamine) (PEHAM) or polypropyleneimine as the building unit.

The core moiety may contain only 1 point of attachment for a building unit or may contain 2, 3 or more points, which may or may not be further utilized for the attachment of building units. Typically, the point of attachment is a free amino group. Core moieties may consist of comprise or be derived from a building unit or may be a molecule different to the building units. Exemplary core moieties are illustrated herein and described in PCT/AU2007/000352.

The liposomes and dendrimers may be combined with any suitable pharmaceutical carrier for intravenous administration. Intravenous administration of the composition is the preferred route since it is the least invasive. Other routes of administration are possible, if desired. Suitable pharmaceutically acceptable carriers include saline, Tris buffer, phosphate buffer, or any other aqueous solution. An appropriate dosage can be established by procedures well known to those of ordinary skill in the art.

The invention is described herein by way of the following examples that are to be understood as merely illustrative and not limitative of the scope of the invention

EXAMPLES

The following molecules were tested for their ability to silence target genes in brain areas expressing the growth hormone secretagogue receptor (hypothalamus)

TAB-NS-Cy3: A duplex 21-mer siRNA with 3' overhang TT wherein the sense strand is conjugated with tabimorelin at the 5' end with a C16 linker and the antisense strand 3'-labeled with Cy3

A 20-mer antisense sequence with a core of 10 DNA nucleotides and 5 nucleotides in each extreme of 2'-o-methyl nucleotide (for non-sense and SOCS3)

A 20-mer antisense sequence with a core of 10 phosphorothioate nt and 5 nt at each extreme of 2'-o-methoxyethyl nt (for PTP1B) which has been conjugated with tabimorelin with a C10 linker through its 5' end Example 1

In Vivo Targeting Validation of a siRNA Labeled with Cy3 and Directed with Tabimorelin to Hypothalamic Centers Animals were treated with a single dose of 30 μg of a non-coding siRNA sequence conjugated to tabimorelin and labeled with Cy3 (long linker) (TAB-NS-Cy3). Unconjugated molecule was used as control (NS-Cy3). Molecules were administered at the lateral ventricle. 1 h later animals were sacrificed, brains removed and processed for visualizing under fluorescent microscopy.

Cy3 labeling was detected in the specific brain regions, in the hypothalamic area, only in mice treated with the conjugated molecule (TAB-NS-Cy3) compared with the unconjugated control (NS-Cy3), demonstrating that tabimorelin can direct nucleic acid molecules to specific brain areas.

Example 2

In Vivo Targeting Validation by Assessing the Physiological Effect of a Tabimorelin Conjugated Antisense Oligonucleotide Directed Against SOCS3 mRNA or PTP1B mRNA in a High-Fat Diet Model of Obesity Animals were fed a high fat diet (HFD) (TD.06414, 60% fat, Harlan) or a standard diet (Control diet: 2014, Harlan) for 12 weeks. Those obese animals that weighted more than the mean body weight of the lean animals plus 2 times the lean standard deviation were selected:

Obese BW>lean BW mean+2×lean SD

Where
BW=Body Weight
SD=Standard Deviation

Figure 2:
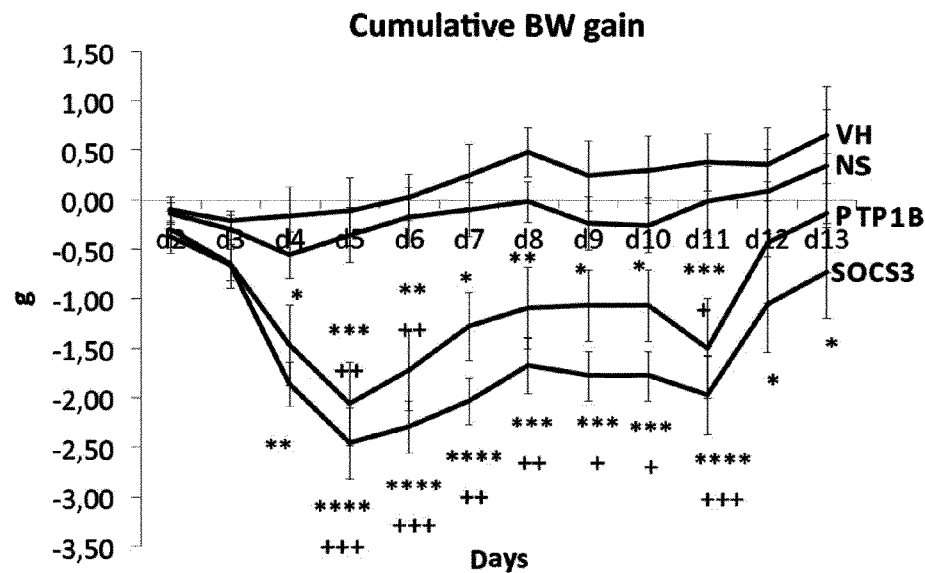
FIG. 2. Cumulative body weight (BW) gain of obese animals after 12 days of treatment with different molecules. A) Cumulative body weight gain (g) of animals treated with vehicle (VH), TAB-NS-ASO4 (NS), TAB-SOCS3-ASO4 (SOCS3) or TAB-PTP1B-ASO4 (PTP1B) for 12 days. *p<0.05; p<0.01; *p<0.001; ****p<0.0001 vs. VH. +p<0.05; ++p<0.01; +++p<0.001; ++++p<0.0001 vs. NS. B) ANOVA table showing the statistically significance of the analysis, where TT means treatment. Data represent mean+ESD FIG. 3. Cumulative food intake (FI) of obese animals after 12 days of treatment with different molecules. A) Cumulative FI gain (g) of animals treated with vehicle (VH), TAB-NS-ASO4 (NS), TAB-SOCS3-ASO4 (SOCS3) or TAB-PTP1B-ASO4 (PTP1B) for 12 days. *p<0.05; p<0.01; *p<0.001; **p<0.0001 vs. VH. +p<0.05; ++p<0.01; +++p<0.001; ++++p<0.0001 vs. NS. B) ANOVA table showing the statistically significance of the analysis, where TT means treatment. Data represent mean+ESD FIG. 4. Daily body weight (BW) gain and food intake (FI) of obese. A) Daily BW gain was the mean of changes in daily body weight. Despite not being significantly different between groups, a tendency to decreased was observed in TAB-SOCS3-ASO4 (SOCS3) and TAB-PTP1B-ASO4 (PTP1B) treated animals. B) Daily FI measured as the mean of daily food ingestion was decreased in TAB-SOCS3-ASO4 (SOCS3) and TAB-PTP1B-ASO4 (PTP1B) treated animals. One-way ANOVA denoted significant differences between treatments (p<0.0001). p<0.01; ***p<0.001 vs. VH. ++p<0.01; +++p<0.001 vs. NS. Data represent mean+ESD.

The day of administration animals were fasted for 8 hours. Under isofluorane anesthesia, 10 doses in 12 days of 30 microg of the following molecules were intranasally administered (5 microl per nostril):

Vehicle (VH) (1×PBS)
TAB-NS-ASO4 (NS)(Non-sense sequence directed with tabimorelin)
TAB-SOCS3-ASO4 (SOCS3)(antisense sequence against socs3 mRNA directed with tabimorelin)
TAB-PTP1B-ASO4 (PTP1B)(antisense sequence against ptp1b mRNA directed with tabimorelin Body weight and food intake were daily monitored. 48 h after the last administration animals were sacrificed and tissues collected for further analysis. FIG. 2 shows cumulative body weight gain during treatment. As shown, animals treated with either TAB-SOCS3-ASO4 or TAB-PTP1B-ASO4 gained significantly less weight than control animals (VH and NS).

Figure 3:
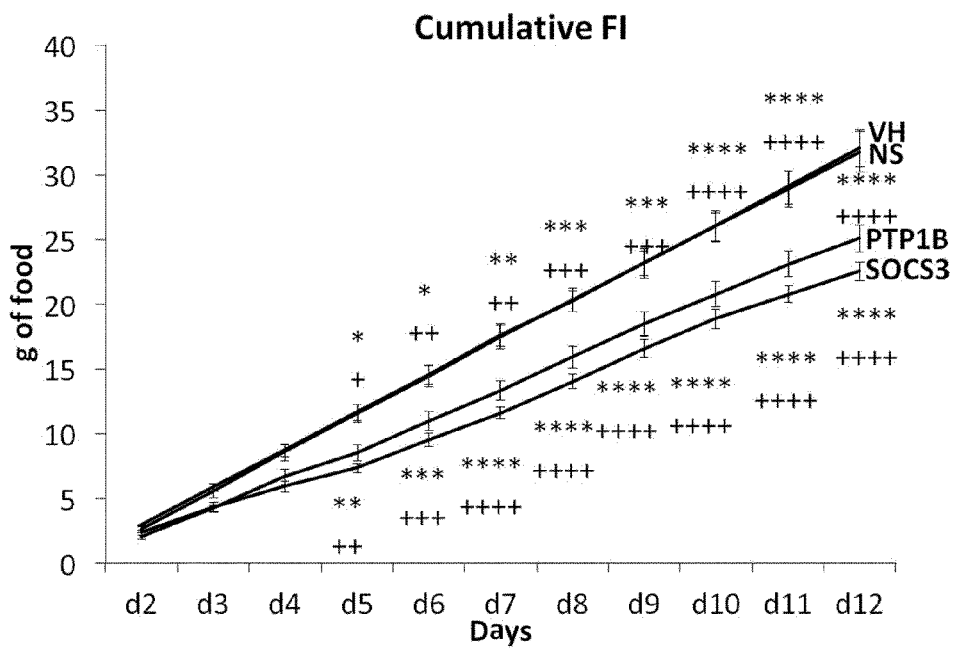

Cumulative food intake (FI) was also significantly decreased in animals treated with TAB-SOCS3-ASO4 or TAB-PTP1B-ASO4 (FIG. 3). These results suggested that both molecules were effective in reaching the targeted hypothalamic areas to produce a reduction in BW and FI.

Figure 4:
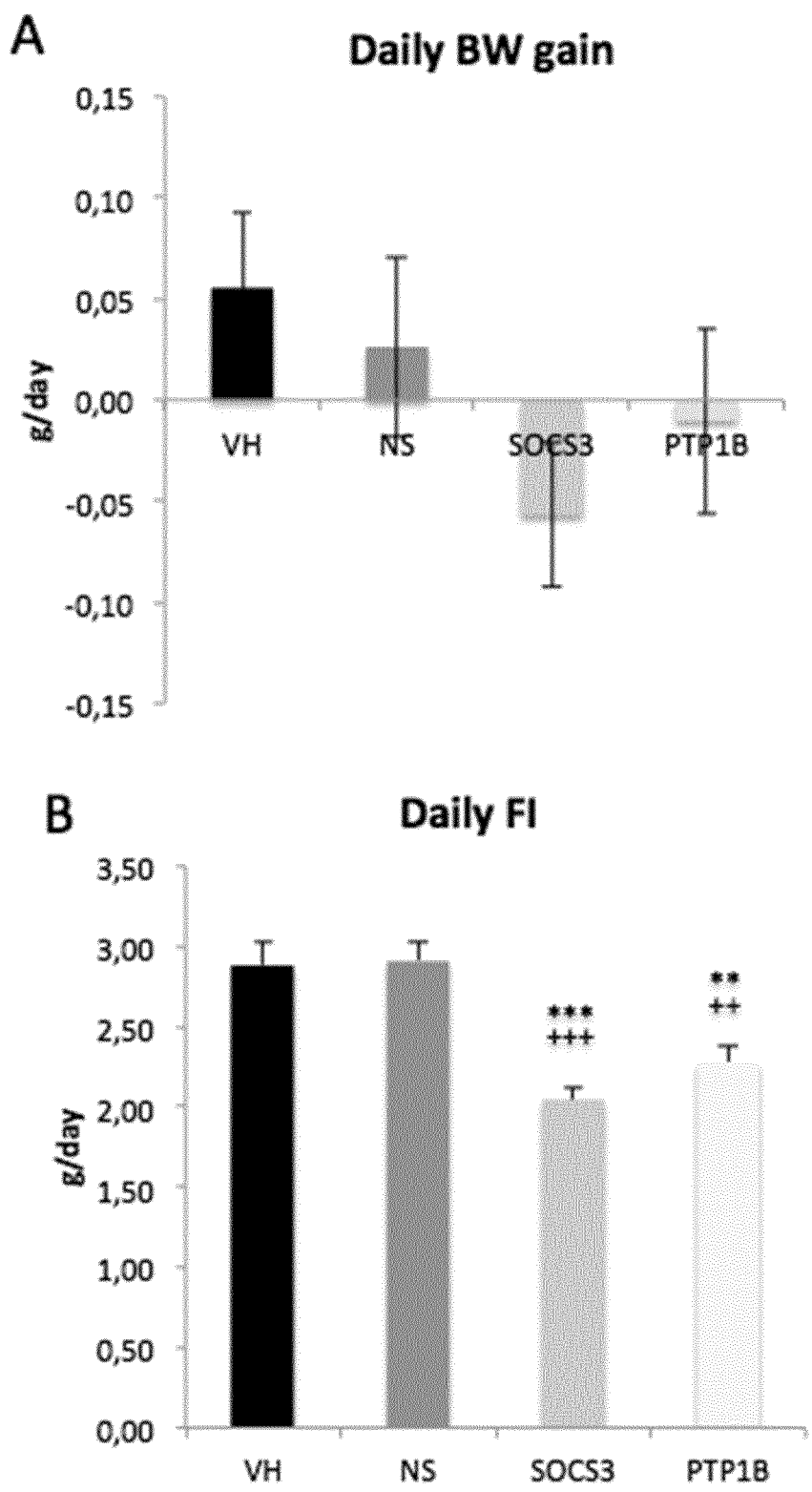

When daily changes were analyzed (FIG. 4), only FI per day was significantly decreased. Despite that daily BW change was not statistically significant, minor daily changes were reflected when BW was monitored all along the period treatment (cumulative BW gain FIG. 2).

Example 3

In Vivo Validation of Targeting (Cellular Specificity) and Knockdown of Ataxin I in Purkinje Cells of the Cerebellum To demonstrate the ability of a conjugated oligonucleotide to be able to reach the targeted area and knockdown a specific gene we selected a ligand for 5-HT1B receptors and conjugated this molecule to a siRNA corresponding to the Ataxin-I mRNA. 5-HT1B receptors are expressed in the Purkinje cells of the cerebellum and using the agonist 5-nonyloxytryptamine oxalate for these receptors, conjugated to a siRNA against mRNA for Ataxin-I, we knockdown this protein only in Purkinje cells. Ataxin-1-siRNA sequence (Lee et al., Nat Neurosci 11, 1137-1139 (2008))

Figure 5:
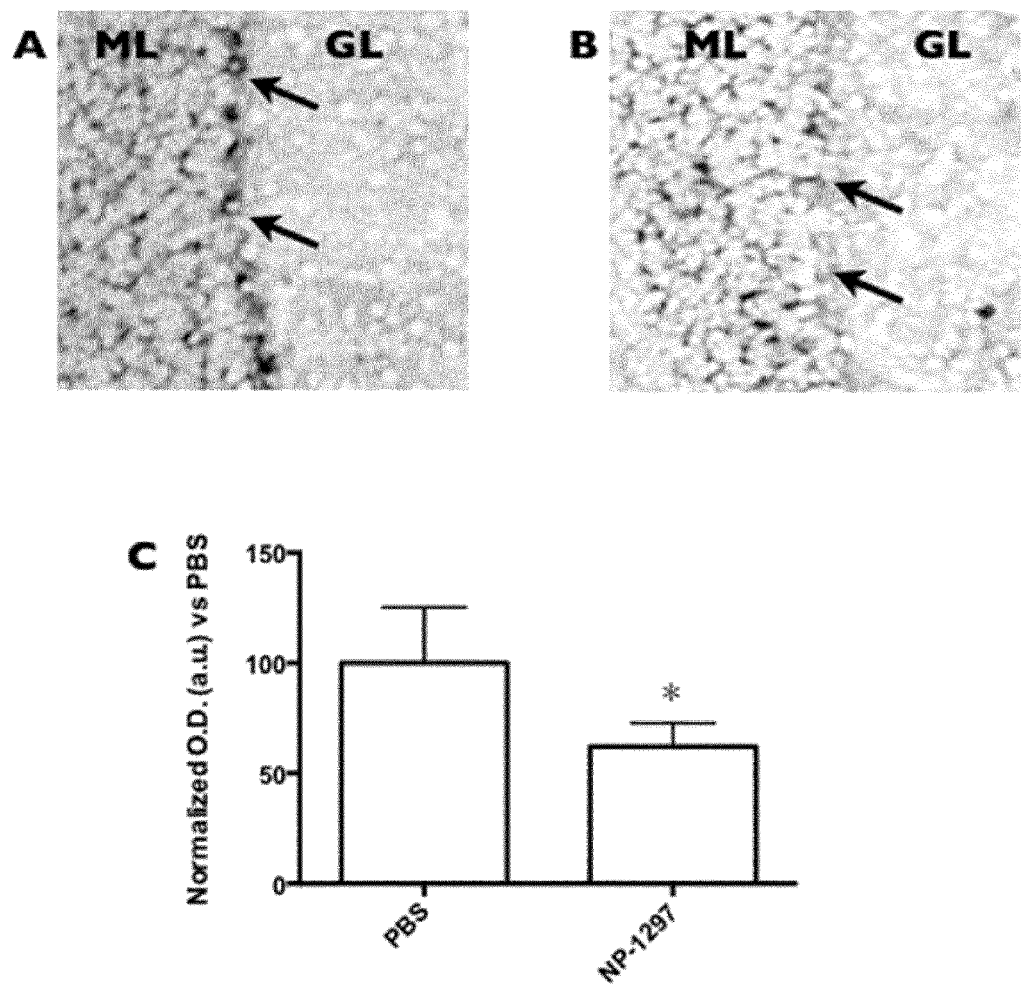
FIG. 5. Microphotographs of sagittal cerebellum sections labeled with a probe for Ataxin-1. A) and B) Arrows indicate the Purkinje cells layer, ML: molecular layer, GL: granular layer. A: example of animal treated with PBS, B: example of animal treated with 5-nonyloxytryptamine oxalate conjugated to a siRNA against mRNA for Ataxin-I (NP-1297). C: Quantification of optical density (ImageJ) in the Purkinje cells layer in arbitrary units (O.D. (a.u.)) normalized against PBS showing a significant decrease (48%±5 s.e.m.) in animals treated with NP-1297 (t test, *p<0.02).
Figure 6:
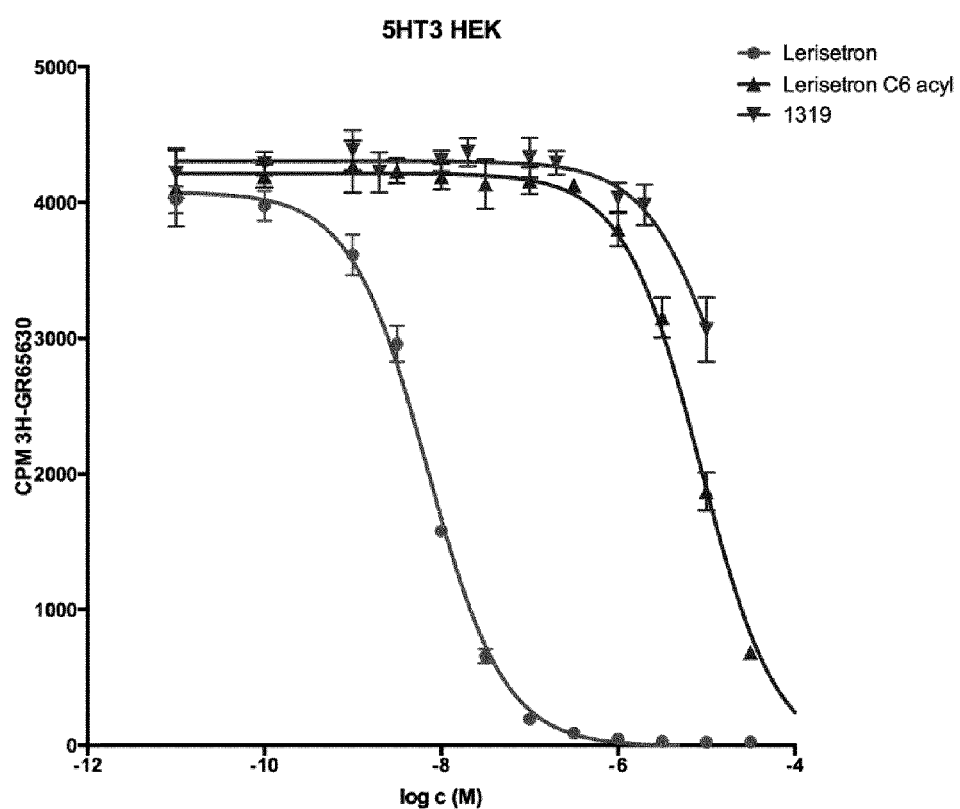
FIG. 6. Binding of 1319 to 5HT3. Displacement of 3H-GR65630 (0.5 nM). Data are presented as mean±SD, n=4 from one experiment. Kd of GR65630 was determined from a saturation assay.
Figure 7:
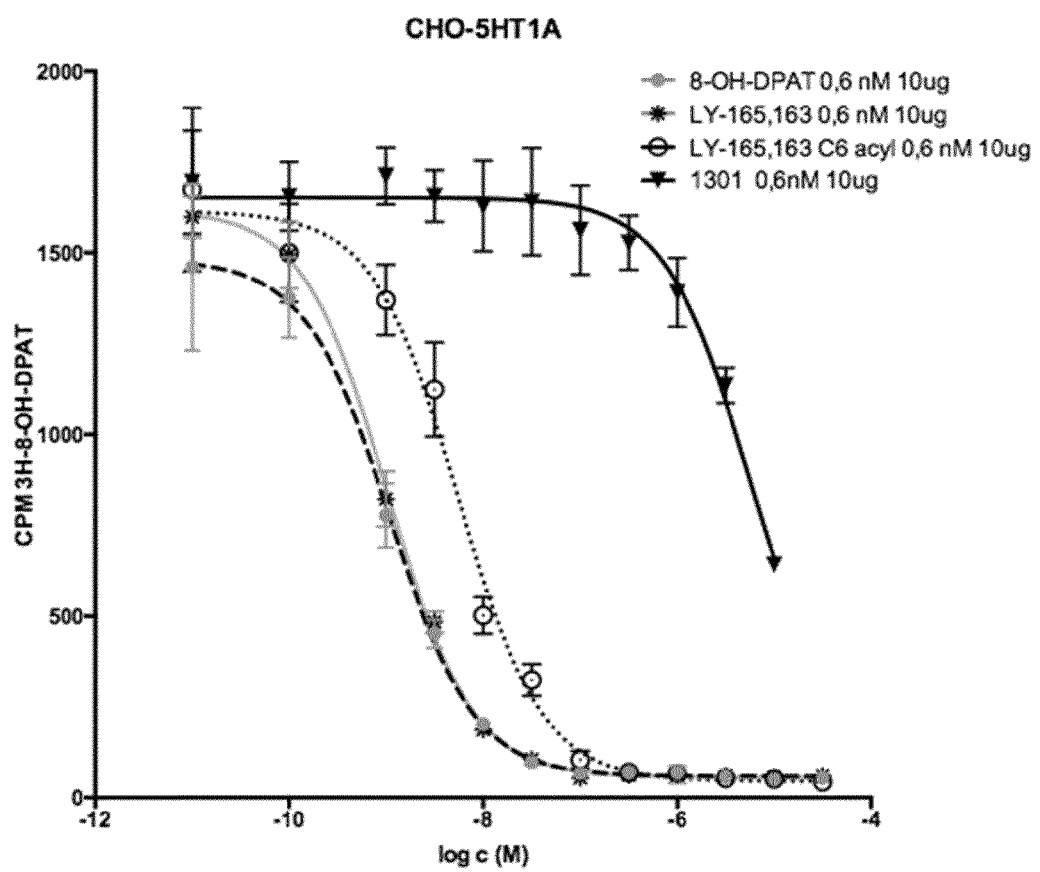
FIG. 7. Binding of 1301 to 5HT1A. Displacement of 3H-8-OH-DPAT (0.6 nM). Data are presented as mean±SD, n=4 from one experiment.

(SEQ ID NO: 9)
Sense Strand gaucuaacgugggcaaguaTT (SEQ ID NO: 10)
Antisense Strand uacuugcccacguuagaucTT For this, five C57/B16 wild type mice were intranasally administered with the conjugated molecule at a concentration of 4 mg/kg/day for four consecutive days and five animals of the same strain were treated with PBS as a control; 24 hours after last administration animals were sacrificed and the brain was processed for in situ hybridization with colorimetric detection. A probe 45 nucleotides long complementary to mouse Ataxin-I mRNA and labeled with digoxigenin at both ends (5' and 3') was used. Sagittal brain cryosections were incubated with this probe to detect if mRNA levels were decreased compared to animals treated with vehicle. Colorimetric signal was obtained incubating with antibody anti-digoxigenin conjugated to alkaline phosphatase and the substrate BCIP/NBT (FIG. 5).

Example 4

Binding Assays of Ligands, Derivatized Ligands and Derivatized Ligands with Oligonucleotide for 5-HT3 and 5-HT1A Candidate conjugate 1319 was synthesized. The conjugate 1319 corresponds to Lerisetron (ligand of the serotonine 5-HT3 receptor) conjugated to a siRNA specific for 5-HT1A (Bortolozzi, A. et al. Mol Psychiatry 17, 612-623 (2012) having the following sequence.

(SEQ ID NO: 11)
Sense strand ggugcucaacaaguggacuTT (SEQ ID NO: 12)
Antisense strand aguccacuuguugagcaccTT Displacement of 3H-GR65630 (0.5 nM) with increasing concentrations of 1319 (from 0.1 nM to 10 uM), Lerisetron-C6-acyl and not derivatized Lerisetron (from 0.1 nM to 30 uM), in HEK-5HT3: 3 ug of protein per well is shown in Table 11.

TABLE 11

| Binding of 1319 to 5HT3 | |
|---|---|
| | IC50 (nM) |
| Lerisetron | 7.0 |
| Lerisetron-C6-acyl | 8.500 |
| 1319 | 14.900 |

Candidate conjugate 1301 was synthesized. The conjugate 1301 corresponds to LY-165,163 (ligand of the serotonine 5HT1A receptor) conjugated to a glycogen synthase kinase 3 beta siRNA sequence (Wang J. et al., J Biol Chem 281, 33842-33848 (2006))

(SEQ ID NO: 13)
sense strand ggcaccagaguugaucuuugTT (SEQ ID NO: 14)
antisense strand caaagaucaacucggugccTT Displacement of 3H-8-OH-DPAT (0.6 nM) with growing concentrations of 1301 (from 0.1 nM to 10 uM), LY-165, 163-C6-acyl and not derivatized LY-165,163 and 8-OH-DPAT as controls (from 0.1 nM to 30 uM), in CHO cells overexpressing human 5HT1A receptor: (Table 12). 10 ug of protein per well preincubated 15 min and incubated 60 min RT.

TABLE 12

| Binding of 1301 to 5HT1A | |
|---|---|
| | IC50 (nM) |
| 8-OH-DPAT | 1.1 |
| LY-165,163 | 1.1 |
| LY-165,163-C6-acyl | 5.5 |
| 1301 | 5.500 |

The invention claimed is:

1. A conjugate comprising:

(i) at least one selectivity agent which binds specifically to a receptor which is internalized by the cell upon binding of said selectivity agent, wherein the selectivity agent is a compound having the structure

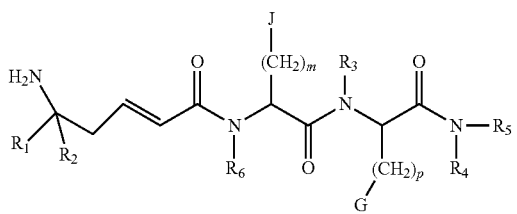

wherein $R_1$ and $R_2$ independently of each other are hydrogen or $C_1$-$C_6$ alkyl or $R_1$ and $R_2$ taken together form a $C_2$-$C_5$ alkylene group;

J is a group

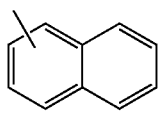

optionally substituted with one or more $C_1$-$C_6$ alkyl or halogen, m is 1, 2 or 3, $R_3$ is $C_1$-$C_6$ alkyl, p is 1, 2 or 3, G is a group

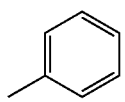 or 

optionally substituted with one or more $C_1$-$C_6$ alkyl or halogen, $R_4$ and $R_5$ independently of each other are hydrogen or $C_1$-$C_6$ alkyl and $R_6$ is hydrogen or $C_1$-$C_6$ alkyl or a pharmaceutically acceptable salt thereof; and (ii) at least one nucleic acid which is capable of specifically inhibiting a target molecule which is expressed in the same cell as the receptor; wherein the receptor is expressed in the mesencephalon, the brainstem, the cortex, the cerebellum, the striatum, the hippocampus, the glia or the medulla.

2. The conjugate according to claim 1 wherein the target molecule is a polypeptide or a mRNA.

3. The conjugate according to claim 2 wherein the inhibition of the target molecule is an inhibition of the activity of the polypeptide if the target polypeptide is a polypeptide or is the silencing of the mRNA if the target polypeptide is a mRNA.

4. The conjugate according to claim 1 wherein the target molecule is a polypeptide selected from the group consisting of the polypeptides defined in the left-hand column of Table 3 or its corresponding mRNAs.

5. The conjugate according to claim 4 wherein the target molecule is the growth hormone secretagogue receptor.

6. A method of treating a disease selected from the group consisting of the diseases shown in the right-hand column of Table 3, wherein the disease is to be treated with the conjugate according to claim 4 directed to a target polypeptide shown in the left-hand column of the same row as the diseases in Table 3.

7. A conjugate according to claim 1 wherein the receptor which is expressed in the mesencephalon is selected from the group consisting of the growth hormone secretagogue receptor, the bombesin BB1 receptor, the bradykinin B2 receptor, the galanin GAL2 receptor, neuropeptide FF/B NPBW2 receptor, the neuropeptide FF/B NPFF2 receptor, the neuropeptide Y Y1 receptor, the neurotensin NTSR1 receptor, the neurotensin NTSR2 receptor, the neuropeptide S receptor, the orexin OX2 receptor, the 5-HT1D receptor, the angiotensin AT2a receptor, the angiotensin AT2b receptor, the calcitonin AM2 receptor, the calcitonin AMY3 receptor, the frizzled FZD6 receptor, the kisspeptin receptor, the melatonin MT1 receptor, the neuropeptide FF/B NPBW1 receptor and the opioid mu receptor.

8. The conjugate according to claim 7 wherein the target molecule is a polypeptide selected from the group consisting of the polypeptides defined in the left-hand column of Table 4 or its corresponding mRNAs.

9. A method of treating a disease selected from the group consisting of the diseases shown in the right-hand column of Table 4, wherein the disease is to be treated with the conjugate of claim 8 directed to a target polypeptide shown in the left-hand column of the same row as the diseases in Table 4.

10. The conjugate according to claim 1 wherein the receptor which is expressed in the brainstem is selected from the group consisting of the 5-HT$_3$ receptor, the galanin receptor 1, the melanocortin MC1 receptor, the melanocortin MC2 receptor, the melanocortin MC3 receptor, the melanocortin MC4 receptor, the calcitonin receptor-like, the CRF2 receptor, the neuropeptide FF/B NPBW2 receptor, the 5-HT1$_A$ receptor, the neuropeptide Y Y2 receptor, the neurotensin NTSR1 receptor, the opioid mu receptor, the orexin OX1 receptor, the orexin OX2 receptor and the dopamine D2 receptor.

11. The conjugate according to claim 10 wherein the target molecule is a polypeptide selected from the group consisting of the polypeptides defined in the left-hand column of Table 5 or its corresponding mRNAs.

12. A method of treating a disease selected from the group consisting of the diseases shown in the right-hand column of Table 5, wherein the disease is to be treated with the conjugate of claim 11 directed to a target polypeptide shown in the left-hand column of the same row as the disease in Table 5.

13. The conjugate according to claim 1 wherein the receptor which is expressed in the cortex is selected from the group consisting of the 5-HT$_3$ receptor, the melanocortin MC1 receptor, the CRF1 receptor, the 5-HT2$_A$ receptor, the alpha1 adrenergic receptor, the bombesin BB1 receptor, the frizzled FZD3 receptor, the bombesin BB3 receptor, the bradykinin B2 receptor, the calcitonin receptor-like receptor, the cholecystokinin CCK2 receptor, the CRF1 receptor, the CRF2 receptor, the galanin GAL2 receptor, the galanin GAL3 receptor, the neuropeptide FF/B NPBW2 receptor, the neuropeptide FF/B NPFF2 receptor, the neuropeptide Y Y1 receptor, the neuropeptide Y Y5 receptor, the neuropeptide Y Y2 receptor, the neurotensin NTSR2 receptor, the opioid kappa receptor, the opioid delta receptor, the somatostatin sst2 receptor, the somatostatin sst3 receptor, the somatostatin sst4 receptor, the 5-HT1A receptor, the endothelin ETa receptor, the endothelin ETb receptor, the melanocortin MC3 receptor, the neuropeptide S NPS receptor, the neurotensin NTSR1 receptor, the orexin OX1 receptor, the orexin OX2 receptor, the vasopressin V1B receptor, the kisspeptin receptor, the melatonin MT1 receptor, the tachykinin NK1 receptor, the tachykinin NK2 receptor and the tachykinin NK3 receptor.

14. The conjugate according to claim 13 wherein the target molecule is a polypeptide selected from the group consisting of the polypeptides defined in the left-hand column of Table 6 or its corresponding mRNAs.

15. A method of treating a disease selected from the group consisting of the diseases shown in the right-hand column of Table 6, wherein the disease is to be treated with the conjugate of claim 14 directed to a target polypeptide shown in the left-hand column of the same row as the disease in Table 6.

16. A conjugate according to claim 1 wherein the receptor which is expressed in the cerebellum is selected from the group consisting of the CRF1 receptor, the 5-HT$_{1B}$ receptor, the frizzled FZD4 receptor, the frizzled FZD10 receptor, the frizzled FZD7 receptor, the bradikinin B2 receptor, the galanin GAL3 receptor, the neurotensin NTSR2 receptor, the endothelin ETb receptor, the formylpeptide FPR1 receptor, the formylpeptide FPR2 receptor, the melatonin MT2 receptor, the vasopressin V1A receptor, the angiotensin AT2a receptor, the angiotensin AT2b receptor, the kisspeptin receptor and the melatonin MT1 receptor.

17. The conjugate according to claim 16 wherein the target molecule is a polypeptide selected from the group consisting of the polypeptides defined in the left-hand column of Table 7 or its corresponding mRNAs.

18. A method of treating a disease selected from the group consisting of the diseases shown in the right-hand column of Table 7, wherein the disease is to be treated with the conjugate of claim 17 directed to a target polypeptide shown in the left-hand column of the same row as the diseases in Table 7.

19. A conjugate according to claim 1 wherein the receptor which is expressed in the striatum is selected from the group consisting of the 5-HT2A receptor, the cholecystokinin CCK2 receptor, the CRF1 receptor, the neuropeptide FF/B NPBW2 receptor, the neuropeptide FF/B NPFF2 receptor, the somatostatin sst5 receptor, the vasopressin V1B receptor, the 5-HT6 receptor, the adenosine A2 receptor, the adenosine A2A receptor, the dopamine D1 receptor, the dopamine D2 receptor, the peptide P518 receptor, the tachykinin NK1 receptor, the tachykinin NK2 receptor and the tachykinin NK3 receptor.

20. The conjugate according to claim 19 wherein the target molecule is a polypeptide selected from the group consisting of the polypeptides defined in the left-hand column of Table 8 or its corresponding mRNAs.

21. A method of treating a disease selected from the group consisting of the diseases shown in the right-hand column of Table 8, wherein the disease is to be treated with the conjugate of claim 20 directed to a target polypeptide shown in the left-hand column of the same row as the diseases in Table 8.

22. A conjugate according to claim 1 wherein the receptor which is expressed in the hippocampus is selected from the group consisting of the 5-HT$_3$ receptor, the bradykinin B2 receptor, the CRF2 receptor, the frizzled FZD3 receptor, the galanin GAL3 receptor, the neuropeptide FF/B NPBW2 receptor, the neuropeptide Y Y1 receptor, the neuropeptide Y Y5 receptor, the neurotensin NTSR2 receptor, the opioid delta receptor, the somatostatin sst3 receptor, the somatostatin sst5 receptor, the 5-HT1A receptor, the adenosine A1 receptor, the endothelin ETa receptor, the endothelin ETb receptor, the formylpeptide FPR1 receptor, the formylpeptide FPR3 receptor, the frizzled FZD8 receptor, the frizzled FZD9 receptor, the melatonin MT2 receptor, the neuropeptide FF/B NPBW2 receptor, the neuropeptide Y Y2 receptor, the neuropeptide FF/B NPFF1 receptor, the neuropeptide Y Y4 receptor, the neurotensin NTSR1 receptor, the orexin OX1 receptor, the orexin OX2 receptor, the somatostatin sst1 receptor, the somatostatin sst5 receptor, the vasopressin V1A receptor and the vasopressin V1B receptor.

23. The conjugate according to claim 22 wherein the target molecule is a polypeptide selected from the group consisting of the polypeptides defined in the left-hand column of Table 9 or its corresponding mRNAs.

24. A method of treating a disease selected from the group consisting of the diseases shown in the right-hand column of Table 9, wherein the disease is to be treated with the conjugate of claim 23 directed to a target polypeptide shown in the left-hand column of the same row as the diseases in Table 9.

25. The conjugate according to claim 1 wherein the receptor which is expressed in the glia is selected from the group consisting of the formylpeptide FPR1 receptor, the formylpeptide FPR2 receptor, the formylpeptide FPR3 receptor and TLR7.

26. The conjugate according to claim 1 wherein the receptor which is expressed in the medulla is selected from the group consisting of EphA1, EphA2, EphA3, EphA4, EphAB1, EphAB2, EphAB3, the opioid mu receptor, the GlyT1 transported, the DP1 receptor, the neurokinin NK1 receptor, the neurokinin NK2 receptor, the neurokinin NK3 receptor, the CXCR4 chemokine receptor, VEGFR1, VEGFR2 and VEGFR3.

27. The conjugate according to claim 26 wherein the target molecule is a polypeptide selected from the group consisting of the polypeptides defined in the left-hand column of Table 10 or its corresponding mRNAs.

28. A method of treating a disease selected from the group consisting of the diseases shown in the right-hand column of Table 10, wherein the disease is to be treated with the conjugate of claim 27 directed to a target polypeptide shown in the left-hand column of the same row as the diseases in Table 10.

29. The conjugate according to claim 1 further comprising at least one additional selectivity agent.

30. The conjugate according to claim 29 wherein the first and said at least one additional selectivity agent are different.

31. The conjugate according to claim 30 wherein both selectivity agents are specific for receptors which are expressed in the same location of the central nervous system.

32. The conjugate according to claim 31 wherein the locations in the central nervous systems to which the first and the at least one additional selectivity agents bind are selected from the group consisting of:
(i) mesencephalon and striatum,
(ii) cortex and hippocampus,
(iii) brainstem and hippocampus,
(iv) cortex, hippocampus and striatum,
(v) cortex, glia and hippocampus,
(vi) hippocampus and striatum,
(vii) brainstem and hypothalamus,
(viii) cortex and striatum
(ix) glia and medulla
(x) brainstem, cortex and mesencephalon,
(xi) brainstem, mesencephalon and striatum,
(xii) brainstem, cortex and hippocampus and
(xiii) cortex, mesencephalon and striatum.

33. The conjugate according to claim 1 wherein the nucleic acid which is capable of specifically binding to a target molecule which is expressed in the same cell as the target molecule is selected from the group consisting of a gapmer, double stranded RNA interference oligonucleotide, double stranded RNA with microRNA activity, an antisense oligonucleotide, an antiMicro RNA oligonucleotide, pre-miRNA, a mRNA coding for microRNAs, or shRNAs, a PNA, a LNA, a ribozyme and an aptamer.

34. The conjugate as defined in claim 1 wherein the selectivity agent is attached to the 5' end of the nucleic acid or to the 3' end of the nucleic acid.

35. The conjugate of claim 1 further comprising a nucleic acid which is complementary to the first nucleic acid.

36. A conjugate as defined in claim 35 wherein the nucleic acid is an interfering RNA.

37. The conjugate according to claim 1 wherein, if the conjugate comprises a second selectivity agent, then
(xiv) if the nucleic acid is a single stranded polynucleotide, the second selectivity agent is attached to the opposite end of the nucleic acid to which the first selectivity agent is attached or to the same end to which the first selectivity agent is attached by means of a bifunctional linker or
(xv) if the nucleic acid is a double stranded polynucleotide, the second selectivity agent is attached either to the opposite end of the strand wherein the first selectivity agent is attached, to either end of the strand which is complementary to the strand wherein the first selectivity agent is attached or to the same end as the end which is attached to the first selectivity agent via a bifunctional linker.

38. The conjugate of claim 1 wherein at least one of the selectivity agents is connected to the nucleic acid by a linking group.

39. A conjugate according to claim 38 wherein the linking group has the structure

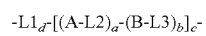

wherein:
A and B represent monomer units independently selected from the group consisting of a monosaccharide, an $C_1$-$C_{50}$ alkyl chain and a ($C_2$-$C_{20}$) alkylene glycol;
a and b are integers ranging from 0 to 50;
c is an integer ranging from 0 and 30;
L1, L2 and L3 are linking compounds independently selected from the group consisting of phosphodiester, phosphorothioate, carbonyl, carbamate, methylphosphonate, carbonyl, guanidinium, sulfamate, sulfamide, formacetal, thioformacetal, sulfone, amide and mixtures thereof;
d is 0 or 1.

40. The conjugate according to claim 39 wherein b and d are 0, c is 1, A is an alkyl chain and L2 is a phosphodiester bond.

41. The conjugate according to claim 1 further comprising a protecting group attached to the end or ends of the polynucleotide which is not attached to the selectivity agent.

42. The conjugate according to claim 1 further comprising a group which facilitates transport across biological membranes.

43. The conjugate according to claim 1 further comprising an endosomolytic peptide.

44. A conjugate comprising
(xvi) at least one selectivity agent which binds specifically to a receptor which is internalized by the cell upon binding of said selectivity agent wherein the selectivity agent is a compound having the structure

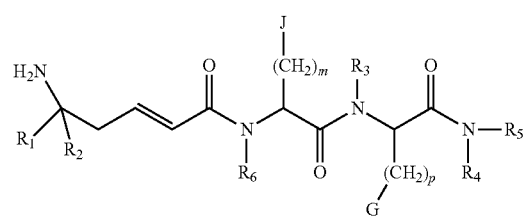

wherein $R_1$ and $R_2$ independently of each other are hydrogen or $C_1$-$C_6$ alkyl or $R_1$ and $R_2$ taken together form a $C_2$-$C_5$ alkylene group;

J is a group

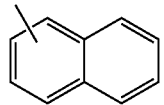

optionally substituted with one or more $C_1$-$C_6$ alkyl or halogen, m is 1, 2 or 3, $R_3$ is $C_1$-$C_6$ alkyl, p is 1, 2 or 3, G is a group

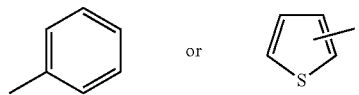

optionally substituted with one or more $C_1$-$C_6$ alkyl or halogen, $R_4$ and $R_5$ independently of each other are hydrogen or $C_1$-$C_6$ alkyl and $R_6$ is hydrogen or $C_1$-$C_6$ alkyl or a pharmaceutically acceptable salt thereof; and (xvii) a nanotransporter comprising a nucleic acid which is capable of specifically binding to a target molecule which is expressed in the same cell as the neurotransmitter transporter, wherein said nanotransporter is a liposome or a dendrimer.

45. The conjugate of claim 1, wherein the selectivity agent is tabimorelin or tabimorelin hemifumarate.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Gapmer for SOCS3
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: um
<220> FEATURE:
<221> NAME/KEY: modified_base
<222> LOCATION: (3)..(4)
<223> OTHER INFORMATION: gm
<220> FEATURE:
<221> NAME/KEY: modified_base
<222> LOCATION: (5)..(5)
<223> OTHER INFORMATION: cm
<220> FEATURE:
<221> NAME/KEY: modified_base
<222> LOCATION: (6)..(6)
<223> OTHER INFORMATION: gm
<220> FEATURE:
<221> NAME/KEY: modified_base
<222> LOCATION: (15)..(15)
<223> OTHER INFORMATION: 2'-O-methyl adenosine
<220> FEATURE:
<221> NAME/KEY: modified_base
<222> LOCATION: (16)..(16)
<223> OTHER INFORMATION: gm
<220> FEATURE:
<221> NAME/KEY: modified_base
<222> LOCATION: (17)..(17)
<223> OTHER INFORMATION: cm
<220> FEATURE:
<221> NAME/KEY: modified_base
<222> LOCATION: (18)..(18)
<223> OTHER INFORMATION: tm
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: tm

<400> SEQUENCE: 1
guggcgctgg tccgagctgt                                              20

<210> SEQ ID NO 2
<211> LENGTH: 21
<212> TYPE: DNA
<213> ORGANISM: Artificial Sequence
<220> FEATURE:
<223> OTHER INFORMATION: siRNA for SOCS3, sense strand

<400> SEQUENCE: 2
cuuuucgcug cagagugact t                                            21

<210> SEQ ID NO 3
<211> LENGTH: 21
<212> TYPE: DNA
<213> ORGANISM: Artificial Sequence
<220> FEATURE:
<223> OTHER INFORMATION: siRNA for SOCS3, antisense strand

<400> SEQUENCE: 3

```
gucacucugc agcgaaaagt t                                              21

<210> SEQ ID NO 4
<211> LENGTH: 20
<212> TYPE: DNA
<213> ORGANISM: Artificial Sequence
<220> FEATURE:
<223> OTHER INFORMATION: gapmer for PTP-1B
<220> FEATURE:
<221> NAME/KEY: modified_base
<222> LOCATION: (1)..(1)
<223> OTHER INFORMATION: gm
<220> FEATURE:
<221> NAME/KEY: modified_base
<222> LOCATION: (2)..(2)
<223> OTHER INFORMATION: cm
<220> FEATURE:
<221> NAME/KEY: modified_base
<222> LOCATION: (3)..(3)
<223> OTHER INFORMATION: um
<220> FEATURE:
<221> NAME/KEY: modified_base
<222> LOCATION: (4)..(5)
<223> OTHER INFORMATION: cm
<220> FEATURE:
<221> NAME/KEY: misc_difference
<222> LOCATION: (6)..(15)
<223> OTHER INFORMATION: Nucleotides conected by phosphorothioate
<220> FEATURE:
<221> NAME/KEY: misc_difference
<222> LOCATION: (6)..(15)
<223> OTHER INFORMATION: Nucleotides connected by phosphorothioate
<220> FEATURE:
<221> NAME/KEY: modified_base
<222> LOCATION: (16)..(17)
<223> OTHER INFORMATION: cm
<220> FEATURE:
<221> NAME/KEY: modified_base
<222> LOCATION: (18)..(18)
<223> OTHER INFORMATION: um
<220> FEATURE:
<221> NAME/KEY: modified_base
<222> LOCATION: (19)..(19)
<223> OTHER INFORMATION: gm
<220> FEATURE:
<221> NAME/KEY: modified_base
<222> LOCATION: (20)..(20)
<223> OTHER INFORMATION: cm

<400> SEQUENCE: 4
gcuccuucca ctgatccugc                                                20

<210> SEQ ID NO 5
<211> LENGTH: 21
<212> TYPE: DNA
<213> ORGANISM: Artificial Sequence
<220> FEATURE:
<223> OTHER INFORMATION: siRNA for PTP-1B, sense strand

<400> SEQUENCE: 5
ccgcaucaug gagaaaggct t                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA for PTP-1B, antisense strand

<400> SEQUENCE: 6
gccuuucucc augaugcggt t                                              21
```

```
<210> SEQ ID NO 7
<211> LENGTH: 7
<212> TYPE: PRT
<213> ORGANISM: Artificial Sequence
<220> FEATURE:
<223> OTHER INFORMATION: sequence that bind to the human transferrin
      receptor

<400> SEQUENCE: 7

His Ala Ile Tyr Pro Arg His
1               5

<210> SEQ ID NO 8
<211> LENGTH: 12
<212> TYPE: PRT
<213> ORGANISM: Artificial Sequence
<220> FEATURE:
<223> OTHER INFORMATION: sequence that bind to the human transferrin
      receptor

<400> SEQUENCE: 8

Thr His Arg Pro Pro Met Trp Ser Pro Val Trp Pro
1               5                   10

<210> SEQ ID NO 9
<211> LENGTH: 21
<212> TYPE: DNA
<213> ORGANISM: Artificial Sequence
<220> FEATURE:
<223> OTHER INFORMATION: Sense Strand Ataxin-1-siRNA sequence

<400> SEQUENCE: 9
gaucuaacgu gggcaaguat t                                               21

<210> SEQ ID NO 10
<211> LENGTH: 21
<212> TYPE: DNA
<213> ORGANISM: Artificial Sequence
<220> FEATURE:
<223> OTHER INFORMATION: Antisense Strand Ataxin-1-siRNA sequence

<400> SEQUENCE: 10
uacuugccca cguuagauct t                                               21

<210> SEQ ID NO 11
<211> LENGTH: 21
<212> TYPE: DNA
<213> ORGANISM: Artificial Sequence
<220> FEATURE:
<223> OTHER INFORMATION: siRNA for serotonine 5-HT1A receptor, sense
      strand

<400> SEQUENCE: 11
ggugcucaac aaguggacut t                                               21

<210> SEQ ID NO 12
<211> LENGTH: 21
<212> TYPE: DNA
<213> ORGANISM: Artificial Sequence
<220> FEATURE:
<223> OTHER INFORMATION: siRNA for serotonine 5-HT1A receptor, antisense
      strand

<400> SEQUENCE: 12
aguccacuug uugagcacct t                                               21
```

```
<210> SEQ ID NO 13
<211> LENGTH: 22
<212> TYPE: DNA
<213> ORGANISM: Artificial Sequence
<220> FEATURE:
<223> OTHER INFORMATION: siRNA for GSK3b, sense strand

<400> SEQUENCE: 13
ggcaccagag uugaucuuug tt                                            22

<210> SEQ ID NO 14
<211> LENGTH: 22
<212> TYPE: DNA
<213> ORGANISM: Artificial Sequence
<220> FEATURE:
<223> OTHER INFORMATION: siRNA for GSK3b, antisense strand

<400> SEQUENCE: 14
caaagaucaa cucuggugcc tt                                            22
```